US00RE44747E

(19) United States
(12) Reissued Patent
Gershoni et al.

(10) Patent Number: US RE44,747 E
(45) Date of Reissued Patent: Feb. 4, 2014

(54) MAPPING AND RECONSTITUTION OF A CONFORMATIONAL DISCONTINUOUS BINDING SURFACE

(75) Inventors: Jonathan Gershoni, Herzylia (IL); Erez Moshe Bublil, Holon (IL); Dimitri Denisov, Hamilton (CA); Galina Denisova, Hamilton (CA)

(73) Assignee: Ramot at Tel-Aviv University Ltd., Tel Aviv (IL)

(21) Appl. No.: 12/718,786

(22) Filed: Mar. 5, 2010

Related U.S. Patent Documents

Reissue of:
(64) Patent No.: 7,587,281
Issued: Sep. 8, 2009
Appl. No.: 11/370,237
Filed: Mar. 8, 2006

U.S. Applications:
(63) Continuation-in-part of application No. PCT/US2004/029290, filed on Sep. 8, 2004.

(60) Provisional application No. 60/500,689, filed on Sep. 8, 2003.

(51) Int. Cl.
*G06F 19/00* (2011.01)
*G01N 33/53* (2006.01)

(52) U.S. Cl.
USPC ..... 702/19; 435/7.1

(58) Field of Classification Search
None
See application file for complete search history.

(56) References Cited

PUBLICATIONS

Barouch et al. Eventual AIDS vaccine failure in a rhesus monkey by viral escape from cytotoxic T lymphocytes. Nature vol. 415, pp. 335-339 (2002).*
The rgp120 HIV Vaccine Study Group Placebo-Controlled Phase 3 Trial of a Recombinant Glycoprotein 120 Vaccine to Prevent HIV-1 Infection. Journal of Infectious Diseases vol. 191, pp. 654-655 (2005).*
Pitisuttithum et all. Randomized, Double-Blind, Placebo-Controlled Efficacy Trial of a Bivalent Recombinant Glycoprotein 120 HIV-1 Vaccine among Injection Drug Users in Bangkok, Thailand. Journal of Infectious Diseases vol. 194, pp. 1661-1671 (2006).*
McCormick et al. Immunization with an Interferon-gamma-gp120 Fusion Protein Induces Enhanced Immune Responses to Human Immunodeficiency Virus gp120. Journal of Infectious Diseases vol. 184, pp. 1423-1430 (2001).*
Pollard et al. Truncated variants of gp120 bind CD4 with high affinity and suggest a minimum CD4 binding region. EMBO Journal vol. 11, pp. 585-591 (1992).*
Burton et al., "Why do we not have an HIV vaccine and how can we make one?" Nature Medicine vol. 4 pp. 495-498 (1998).
Chen et al., Protection of rhesus macaques against disease progression from pathogenic SHIV-89.6PD by vaccination with phage-displayed HIV-1 epitopes Nature Medicine vol. 7 pp. 1225-1231 (2001).
Howie et al., "Synthetic peptides representing discontinuous CD4 binding epitopes of HIV-1 gp120 that induce T cell apoptosis and block cell death induced by gp120" FASEB Journal vol. 12, pp. 991-998 (1998).
Scala et al., "Selection of HIV-Specific Immunogenic Epitopes by Screening Random Peptide Libraries with HIV-1-Positive Sera" Journal of Immunology vol. 162 pp. 6155-6161 (1999).
Villen et al., "Synthetic Peptides as Functional Mimics of a Viral Discontinuous Antigenic Site Biologicals" vol. 29 pp. 265-269 (2001 ).
Azoitei et al. "Computation-Guided Backbone Grafting of a Discontinuous Motif onto a Protein Scaffold" Science 334:373-376 (2011).
Barouch et al "Vaccine protection against acquisition of neutralizationresistant SIV challenges in rhesus monkeys" Nature, 482:89-94 (2012).
Correia et al. "Computational Design of Epitope-Scaffolds Allows Induction of Antibodies Specific for a Poorly Immunogenic HIV Vaccine Epitope" Structure 18, 1116-1126, (2010).
Drakopoulou et al., "Changing the Structural Context of a Functional b-Hairpin, Synthesis and Characterization of a Chimera Containing the Curaremimetic Loop of a Snake Toxin in the Scorpion a/b Scaffold" The Journal of Biological Chemistry 271(20):11979-11987 (1996).
Karasavvas et al., "The Thai Phase III HIV Type 1 Vaccine Trial (RV144) Regimen Induces Antibodies That Target Conserved Regions Within the V2 Loop of gp120" Aids Research and Human Retroviruses 28:1444-1457 (2012).
Larsson et al "Crystal Structure of Thermobifida fusca Endoglucanase Cel6A in Complex with Substrate and Inhibitor: The Role of Tyrosine Y73 in Substrate Ring Distortion" Biochemistry vol. 44,39 (2005).
Lu et al "A de Novo Designed Template for Generating Conformation-specific Antibodies That Recognize alpha-Helices in Proteins" The Journal of Biological Chemistry, 277(26):23515-23524 (2002).

(Continued)

*Primary Examiner* — John S Brusca
(74) *Attorney, Agent, or Firm* — Browdy and Neimark, PLLC

(57) ABSTRACT

The structure of conformational, discontinuous binding surfaces that associate with a binding molecule, preferably the epitopes of monoclonal antibodies (mAbs) may be discovered. The binding molecule is used to select specific peptides from a peptide library that, in turn, are used as a binding surface (epitope) defining database that is applied via a novel computer algorithm to analyze the crystalline-structure of the original binding surface (antigen). An antigenic epitope-mimetic that is recognized by its original mAb may be reconstituted based on the segments of the epitope identified in the prediction. The basic elements of the binding domain on gp120 that is recognized by broadly neutralizing antibody b12 are disclosed, as in their use in making vaccines for preventing or treating HIV.

23 Claims, 32 Drawing Sheets
(5 of 32 Drawing Sheet(s) Filed in Color)

(56) References Cited

PUBLICATIONS

Martin et al. "Rational design of a CD4 mimic that inhibits HIV-1 entry and exposes cryptic neutralization epitopes" http://www.nature.com/naturebiotechnology, 21: 71-76 (2003).

McLellan et al., "Design and Characterization of Epitope-Scaffold Immunogens That Present the Motavizumab Epitope from Respiratory Syncytial Virus" J. Mol. Biol. 409:853-866 (2011).

McLellan et al., "Structure of HIV-1 gp120 V1/V2 domain with broadly neutralizing antibody PG9" Nature vol. 480 pp. 336-343 (2011).

Ofek et al., "Elicitation of structure-specific antibodies by epitope scaffolds" Proceedings of the National Academy of Sciences USA vol. 107, pp. 17880-17887 (2010).

Stricher et al., "Design of Miniproteins by the Transfer of Active Sites Onto Small-Size Scaffolds" Methods in Molecular Biology, 340:113-149 (2006).

Zhou et al., "Structural definition of a conserved neutralization epitope on HIV-1 gp120" Nature, 445:732-737 (2007).

Zhou et al., "Structural definition of a conserved neutralization epitope on HIV-1 gp120" www.nature.com/nature, pp. 1-25 (2007).

* cited by examiner

FIGURE 2A

| | | | | | | | | | | | | | |
|---|---|---|---|---|---|---|---|---|---|---|---|---|---|
| C | S | G | L | R | N | E | T | F | L | R | C | | |
| C | E | F | F | Q | Q | H | M | L | R | V | P | R | C |
| C | N | M | K | L | K | L | R | E | M | T | Q | R | C |
| C | M | T | R | P | T | S | L | T | Q | L | T | G | C |
| C | L | H | I | R | V | N | E | T | A | Y | R | V | C |
| C | D | F | L | R | E | H | G | M | K | N | P | R | C |
| C | R | S | R | P | T | N | M | T | T | L | R | D | C |
| C | A | A | Y | N | A | T | R | G | T | V | S | A | C |
| C | Q | L | L | H | T | W | E | D | K | M | R | K | C |
| C | R | N | G | E | L | W | L | R | R | P | G | L | C |
| C | M | V | R | P | S | N | W | D | A | L | T | R | C |

FIGURE 2B

| | | | | | | | | | | | | |
|---|---|---|---|---|---|---|---|---|---|---|---|---|
| CO | OG | GU | UB | BX | XJ | JO | OZ | ZU | UB | BC | | |
| CJ | JZ | ZZ | ZX | XX | XH | HM | MU | UB | BU | UP | PB | BC |
| CX | XM | MB | BU | UB | BU | UB | BJ | JM | MO | OX | XB | BC |
| CM | MO | OB | BP | PO | OO | OU | UO | OX | XU | UO | OG | GC |
| CM | MU | UB | BP | PO | OX | XZ | ZJ | JA | AU | UO | OB | BC |
| CU | UH | HU | UB | BU | UX | XJ | JO | OA | AY | YB | BU | UC |
| CJ | JZ | ZU | UB | BJ | JH | HG | GM | MB | BX | XP | PB | BC |
| CB | BO | OB | BP | PO | OX | XM | MO | OO | OU | UB | BJ | JC |
| CA | AA | AY | YX | XA | AO | OB | BG | GO | OU | UO | OA | AC |
| CX | XU | UU | UH | HO | OZ | ZJ | JJ | JB | BM | MB | BB | BC |
| CB | BX | XG | GJ | JU | UZ | ZU | UB | BB | BP | PG | GU | UC |

FIGURE 2C

| | | | |
|---|---|---|---|
| UB | 10 | YB | 1 |
| BC | 6 | CO | 1 |
| BU | 5 | OG | 1 |
| BP | 4 | CU | 1 |
| OX | 4 | UP | 1 |
| OB | 4 | HM | 1 |
| UO | 4 | XH | 1 |
| OU | 3 | BO | 1 |
| BJ | 3 | XX | 1 |
| ZU | 3 | ZX | 1 |
| BX | 3 | ZZ | 1 |
| MO | 3 | JC | 1 |
| MB | 3 | JH | 1 |
| JZ | 2 | HG | 1 |
| CX | 2 | GM | 1 |
| CB | 2 | XP | 1 |
| CM | 2 | CA | 1 |
| MU | 2 | AA | 1 |
| CJ | 2 | YX | 1 |
| PB | 2 | XA | 1 |
| XU | 2 | XB | 1 |
| GU | 2 | BG | 1 |
| UH | 2 | AC | 1 |
| UC | 2 | JM | 1 |
| ZJ | 2 | XZ | 1 |
| AY | 2 | JA | 1 |
| XJ | 2 | AU | 1 |
| BB | 2 | PG | 1 |
| XM | 2 | GC | 1 |
| OA | 2 | XG | 1 |
| PO | 2 | GJ | 1 |
| HU | 1 | JU | 1 |
| UX | 1 | UZ | 1 |
| BM | 1 | UU | 1 |
| JB | 1 | JJ | 1 |

FIGURE 3A

| | A(6.2) | B(12.5) | C(3.1) | G(6.2) | H(3.1) | J(9.3) | M(3.1) | O(15.6) | P(6.2) | U(18.7) | X(6.2) | Y(3.1) | Z(6.3) |
|---|---|---|---|---|---|---|---|---|---|---|---|---|---|
| A | 0.38 | 0.78 | 0.19 | 0.38 | 0.19 | 0.58 | 0.19 | 0.97 | 0.38 | 1.16 | 0.38 | 0.19 | 0.39 |
| B | 0.78 | 1.56 | 0.39 | 0.78 | 0.39 | 1.16 | 0.39 | 1.95 | 0.78 | 2.34 | 0.78 | 0.39 | 0.79 |
| C | 0.19 | 0.39 | 0.10 | 0.19 | 0.10 | 0.29 | 0.10 | 0.48 | 0.19 | 0.58 | 0.19 | 0.10 | 0.20 |
| G | 0.38 | 0.78 | 0.19 | 0.38 | 0.19 | 0.86 | 0.29 | 1.45 | 0.58 | 1.74 | 0.58 | 0.29 | 0.59 |
| H | 0.19 | 0.39 | 0.10 | 0.19 | 0.10 | 0.29 | 0.10 | 0.48 | 0.19 | 0.58 | 0.19 | 0.10 | 0.20 |
| J | 0.58 | 1.16 | 0.29 | 0.58 | 0.29 | 0.86 | 0.29 | 1.45 | 0.58 | 1.74 | 0.58 | 0.29 | 0.59 |
| M | 0.19 | 0.39 | 0.10 | 0.19 | 0.10 | 0.29 | 0.10 | 0.48 | 0.19 | 0.58 | 0.19 | 0.10 | 0.20 |
| O | 0.97 | 1.95 | 0.48 | 0.97 | 0.48 | 1.45 | 1.48 | 2.43 | 0.97 | 2.92 | 0.97 | 0.48 | 0.98 |
| P | 0.38 | 0.78 | 0.19 | 0.38 | 0.19 | 0.58 | 0.19 | 0.97 | 0.38 | 1.16 | 0.38 | 0.19 | 0.39 |
| U | 1.16 | 2.34 | 0.58 | 1.16 | 0.58 | 1.74 | 0.58 | 2.92 | 1.16 | 3.50 | 1.16 | 0.58 | 1.18 |
| X | 0.38 | 0.78 | 0.19 | 0.38 | 0.19 | 0.58 | 0.19 | 0.97 | 0.38 | 1.16 | 0.38 | 0.19 | 0.39 |
| Y | 0.19 | 0.39 | 0.10 | 0.19 | 0.10 | 0.29 | 0.10 | 0.48 | 0.19 | 0.58 | 0.19 | 0.10 | 0.20 |
| Z | 0.39 | 0.79 | 0.20 | 0.39 | 0.20 | 0.59 | 0.39 | 0.98 | 0.39 | 1.18 | 0.39 | 0.20 | 0.40 |

FIGURE 4A

| | Pair | aa | | D |
|---|---|---|---|---|
| A (5,24) | UB | L111 | K117 | 7.8 |
| | UB | L116 | K117 | 3.2 |
| | BP | K117 | P118 | 3.5 |
| | BC | K117 | C119 | 6.8 |
| | BC | K117 | C205 | 7.2 |
| | BP | K117 | P206 | 6.5 |
| | BU | K117 | V120 | 6.8 |
| | BU | K117 | V208 | 6.9 |
| | UB | V120 | K121 | 3.5 |
| | UB | V120 | K432 | 7.5 |
| | BP | K121 | P124 | 7.7 |
| | BU | K121 | V200 | 5.6 |
| | BU | K121 | I201 | 4.8 |
| | BU | K121 | I424 | 7.6 |
| | UB | L122 | K432 | 4.2 |
| | UB | I201 | K432 | 7.8 |
| | OX | T202 | Q203 | 3.3 |
| | BU | K207 | V208 | 3.1 |
| | BU | R419 | I420 | 3.6 |
| | BU | K421 | I423 | 6.0 |
| | UB | I423 | K432 | 7.9 |
| | UB | I424 | K432 | 7.1 |
| | BP | K207 | P437 | 7.5 |
| | UB | I420 | K421 | 3.4 |
| | BP | K421 | P437 | 7.6 |
| | BP | K421 | P438 | 7.9 |
| B (3,8) | UB | V270 | K348 | 7.8 |
| | UB | V271 | K348 | 7.7 |
| | UB | I272 | K348 | 7.1 |
| | UB | L349 | R350 | 2.9 |
| | OX | S347 | Q352 | 7.9 |
| | OX | S347 | N355 | 7.8 |
| | BU | K348 | l349 | 2.8 |
| | UB | L349 | K357 | 7.8 |

| | Pair | aa | | D |
|---|---|---|---|---|
| C (3,7) | UB | I333 | R335 | 5.9 |
| | UB | I333 | K337 | 6.7 |
| | OX | S334 | N339 | 7.9 |
| | OX | S334 | N340 | 7.9 |
| | BU | R335 | I414 | 4.0 |
| D (3,7) | UB | V 87 | K227 | 7.6 |
| | UB | L226 | K227 | 3.5 |
| | UB | L226 | K485 | 7.2 |
| | BC | K227 | C239 | 7.9 |
| | BU | K227 | V242 | 7.3 |
| | BU | K227 | V245 | 4.9 |
| | BC | K227 | C247 | 7.8 |
| E (2,7) | BU | K357 | I360 | 7.1 |
| | UB | I360 | K362 | 6.4 |
| | UB | I360 | R469 | 6.5 |
| | BU | K367 | I467 | 7.1 |
| | UB | I371 | R469 | 7.8 |
| | UB | I467 | R469 | 6.9 |
| F (2,5) | OX | S440 | Q442 | 5.6 |
| | UB | I443 | R444 | 3.4 |
| | BC | R444 | C445 | 3.6 |
| G (1,4) | UB | I213 | R252 | 7.4 |
| | UB | I215 | R252 | 5.0 |
| | UB | I251 | R252 | 3.6 |

FIGURE 5A

```
CAHFPPRSQMIADC
CAHFAPGTAMYSDC
CRQFPHSSSMYTDC
CRESRAALERGWWC
CEARTHNEARRRRC
CAAARSTGETSAHY
CYYRMGANYTVGEC
CSVSPLYAYDDPLC
CTQMHEMDPNFPPC
CVTALGPNYTGQEC
CYVQQPWWVLEREC
CADVMGPLVTAAEC
CADVMGPLVTAGEC
CVVFLDVSEAFRDC
VWRCNWF
AASWNGR
```

FIGURE 5B

```
CA AH HZ ZP PP PB BO OX XM MU UA AJ JC
CA AH HZ ZA AP PG GO OA AM MY YO OJ JC
CB BX XZ ZP PH HO OO OO OM MY YO OJ JC
CB BJ JO OB BA AA AU UJ JB BG GZ ZZ ZC
CJ JA AB BO OH HX XJ JA AB BB BB BB BC
CA AA AA AB BO OO OG GJ JO OO OA AH HY
CY YY YB BM MG GA AX XY YO OU UG GJ JC
CO OU UO OP PU UY YA AY YJ JJ JP PU UC
CO OX XM MH HJ JM MJ JP PX XZ ZP PP PC
CU UO OA AU UG GP PX XY YO OG GX XJ JC
CY YU UX XX XP PZ ZZ ZU UU UJ JB BJ JC
CA AJ JU UM MG GP PU UU UO OA AA AJ JC
CA AJ JU UM MG GP PU UU UO OA AG GJ JC
CU UU UZ ZU UJ JU UO OJ JA AZ ZB BJ JC
UZ ZB BC CX XZ ZZ Z
AA AO OZ ZX XG GB B
```

FIGURE 5C

| | Pair | aa | | D |
|---|---|---|---|---|
| A(4,12) | JA | E187 | A209 | 7.7 |
| | JA | E187 | A208 | 7.8 |
| | JA | D197 | A217 | 7.7 |
| | JA | D197 | A204 | 8.0 |
| | AA | A204 | A209 | 8.0 |
| | GP | G206 | P207 | 3.8 |
| | AA | A208 | A209 | 3.8 |
| | AJ | A209 | E213 | 8.0 |
| | AJ | A209 | E212 | 6.4 |
| | JA | E212 | A217 | 6.0 |
| | JA | E213 | A217 | 6.1 |
| B(3,6) | OA | S 16 | A 22 | 7.8 |
| | AJ | A 22 | E 28 | 7.5 |
| | AJ | A 22 | E 29 | 7.5 |
| | JA | E 28 | A 31 | 4.7 |
| | JA | E 29 | A 31 | 4.2 |
| | AJ | A 31 | E 35 | 8.0 |
| C(2,6) | AJ | A 64 | E 71 | 8.0 |
| | JA | E 71 | A 78 | 7.6 |
| | JA | E 75 | A 78 | 4.8 |
| | JA | E 76 | A 78 | 4.4 |
| | AJ | A 78 | E 79 | 3.8 |
| | AJ | A 78 | D 81 | 5.0 |
| D(4,5) | OA | S149 | A174 | 7.8 |
| | AJ | A174 | E175 | 3.8 |
| | AA | A174 | A177 | 7.3 |
| | JA | E175 | A177 | 6.1 |
| | AJ | A177 | E180 | 8.0 |

FIGURE 6

| Light Chains | | SEQ ID NO: | |
|---|---|---|---|
| CG10 | QSVDYDGDSYMNWY | 29 | CDR1 |
| 17b | ESVSSDLAWYQQKP | 30 | |
| CG10 | AASNLES | 31 | CDR2 |
| 17b | GASTRAT | 31 | |
| CG10 | SHEDP | 33 | CDR3 |
| 17b | YNNWPR | 34 | |

| Heavy Chains | | SEQ ID NO: | |
|---|---|---|---|
| CG10 | AGYTFTDYWIG | 35 | CDR1 |
| 17b | SGDTFIRYSFT | 36 | |
| CG10 | PGGDYTLY | 37 | CDR2 |
| 17b | TILDVAHH | 38 | |
| CG10 | YYGYSYAWFAYW | 39 | CDR3 |
| 17b | EGEADEGEYRNN | 40 | |

FIGURE 7A

CAKEGDLNKYKPWC
CMRLPIDNRYRPWC
CRYAVTVAQKNRYC
CQFDPEIDWIPPKC
CRSDTTVGWRPPRC
CVWETGSRWRMPKC
CKGVHVEDQYRPWC
CQWETNGGWTRPKC
CWSPDSAWEKPKCC
CWEGPVSPAGLPRC
CEYDNQSHWARPKC
CGMTLRGWRDPRMC
CRVAQAEGWAPPRC
CIRNYHVFPPGKVC
CAKNYLLYPPIRQC
CRTGTVSWGQYKGC
CKLDYRIGENFAQC
CKYEVSQEARERWC
CGTHPYGSPQFMTC
CLVGETRLGIWLGC
CSSSCAKWAWSHCC
CRGGGTDAQGWYTC
CRRPVVDAGWNMSC
CSGASAWRGEMQHC
CKDLAEGGPAIGSC
CYKPLYAQGWGWYC
CSPRTRTGTARSRC
CDPKRNPDRIMHPC

FIGURE 7B

| | | | | | | | | | | | | |
|---|---|---|---|---|---|---|---|---|---|---|---|---|
| CA | AB | BJ | JG | GJ | JU | UX | XB | BY | YB | BP | PZ | ZC |
| CM | MB | BU | UP | PU | UJ | JX | XB | BY | YB | BP | PZ | ZC |
| CB | BY | YA | AU | UO | OU | UA | AX | XB | BX | XB | BY | YC |
| CX | XZ | ZJ | JP | PJ | JU | UJ | JZ | ZU | UP | PP | PB | BC |
| CB | BO | OJ | JO | OO | OU | UG | GZ | ZB | BP | PP | PB | BC |
| CU | UZ | ZJ | JO | OG | GO | OB | BZ | ZB | BM | MP | PB | BC |
| CB | BG | GU | UH | HU | UJ | JJ | JX | XY | YB | BP | PZ | ZC |
| CX | XZ | ZJ | JO | OX | XG | GG | GZ | ZO | OB | BP | PB | BC |
| CZ | ZO | OP | PJ | JO | OA | AZ | ZJ | JB | BP | PB | BC | CC |
| CZ | ZJ | JG | GP | PU | UO | OP | PA | AG | GU | UP | PB | BC |
| CJ | JY | YJ | JX | XX | XO | OH | HZ | ZA | AB | BP | PB | BC |
| CG | GM | MO | OU | UB | BG | GZ | ZB | BJ | JP | PB | BM | MC |
| CB | BU | UA | AX | XA | AJ | JG | GZ | ZA | AP | PP | PB | BC |
| CU | UB | BX | XY | YH | HU | UZ | ZP | PP | PG | GB | BU | UC |
| CA | AB | BX | XY | YU | UU | UY | YP | PP | PU | UB | BX | XC |
| CB | BO | OG | GO | OU | UO | OZ | ZG | GX | XY | YB | BG | GC |
| CB | BU | UJ | JY | YB | BU | UG | GJ | JX | XZ | ZA | AX | XC |
| CB | BY | YJ | JU | UO | OX | XJ | JA | AB | BJ | JB | BZ | ZC |
| CG | GO | OH | HP | PY | YG | GO | OP | PX | XZ | ZM | MO | OC |
| CU | UU | UG | GJ | JO | OB | BU | UG | GU | UZ | ZU | UG | GC |
| CO | OO | OO | OC | CA | AB | BZ | ZA | AZ | ZO | OH | HC | CC |
| CB | BG | GG | GG | GO | OJ | JA | AX | XG | GZ | ZY | YO | OC |
| CB | BB | BP | PU | UU | UJ | JA | AG | GZ | ZX | XM | MO | OC |
| CO | OG | GA | AO | OA | AZ | ZB | BG | GJ | JM | MX | XH | HC |
| CB | BJ | JU | UA | AJ | JG | GG | GP | PA | AU | UG | GO | OC |
| CY | YB | BP | PU | UY | YA | AX | XG | GZ | ZG | GZ | ZY | YC |
| CO | OP | PB | BO | OB | BO | OG | GO | OA | AB | BO | OB | BC |
| CJ | JP | PB | BB | BX | XP | PJ | JB | BU | UM | MH | HP | PC |

FIGURE 7C

| | | | | | | | | | |
|---|---|---|---|---|---|---|---|---|---|
| PB | 11 | GJ | 4 | OA | 3 | ZU | 2 | JJ | 1 |
| CB | 10 | OP | 4 | OH | 3 | AJ | 2 | UH | 1 |
| BC | 9 | XB | 4 | MO | 3 | OJ | 2 | YO | 1 |
| BP | 9 | ZA | 4 | OO | 3 | MC | 1 | XA | 1 |
| GZ | 8 | JU | 4 | ZY | 2 | HZ | 1 | ZX | 1 |
| BU | 7 | XZ | 4 | HU | 2 | MP | 1 | XM | 1 |
| GO | 7 | XY | 4 | HC | 2 | AP | 1 | GA | 1 |
| YB | 6 | ZB | 4 | HP | 2 | YH | 1 | AO | 1 |
| AB | 6 | UO | 4 | GC | 2 | ZP | 1 | JM | 1 |
| UG | 6 | OG | 4 | CZ | 2 | PG | 1 | MX | 1 |
| ZJ | 5 | AZ | 3 | ZG | 2 | GB | 1 | XH | 1 |
| PP | 5 | JB | 3 | YA | 2 | UC | 1 | CY | 1 |
| AX | 5 | PZ | 3 | BM | 2 | YU | 1 | XP | 1 |
| UJ | 5 | UA | 3 | XC | 2 | XO | 1 | UM | 1 |
| PU | 5 | PJ | 3 | CC | 2 | XX | 1 | MH | 1 |
| BX | 5 | UB | 3 | GP | 2 | YP | 1 | GM | 1 |
| BY | 5 | UU | 3 | CX | 2 | JZ | 1 | | |
| BG | 5 | XG | 3 | PA | 2 | PC | 1 | | |
| JO | 5 | CO | 3 | AG | 2 | OZ | 1 | | |
| OC | 5 | UP | 3 | CJ | 2 | GX | 1 | | |
| OB | 5 | UZ | 3 | JY | 2 | XJ | 1 | | |
| BO | 5 | JP | 3 | YJ | 2 | MB | 1 | | |
| BJ | 4 | BZ | 3 | UY | 2 | PY | 1 | | |
| XC | 4 | GU | 3 | AU | 2 | YG | 1 | | |
| JX | 4 | CA | 3 | BB | 2 | PX | 1 | | |
| JG | 4 | CU | 3 | YC | 2 | ZM | 1 | | |
| GG | 4 | JA | 3 | CG | 2 | CM | 1 | | |
| OU | 4 | ZO | 3 | OX | 2 | UX | 1 | | |

FIGURE 8

| | pair | aa | | D* |
|---|---|---|---|---|
| A (7,18) | BP | K117 | P118 | 3.5550 |
| | BC | K117 | C119 | 7.0680 |
| | BC | K117 | C205 | 7.3270 |
| | BP | K117 | P206 | 5.7460 |
| | BY | K117 | Y435 | 7.1190 |
| | PP | P118 | P206 | 5.7260 |
| | PB | P118 | K121 | 7.5180 |
| | PB | P118 | K432 | 7.7770 |
| | CB | C119 | K121 | 6.4210 |
| | CB | C119 | K432 | 7.2460 |
| | BP | K121 | P124 | 7.5800 |
| | CB | C205 | K207 | 6.7980 |
| | PB | P206 | K207 | 3.6850 |
| | PP | P206 | P437 | 7.8260 |
| | BY | K207 | Y435 | 7.9040 |
| | BP | K207 | P437 | 7.2030 |
| | PB | P417 | R419 | 6.9530 |
| | CB | C418 | R419 | 3.6110 |
| | CB | C418 | K421 | 7.4810 |
| | BY | K421 | Y435 | 6.5380 |
| | BP | K421 | P437 | 7.8970 |
| | BP | K421 | P438 | 7.9530 |
| | BY | K432 | Y435 | 7.9660 |
| | PP | P437 | P438 | 3.6820 |
| | YB | Y384 | R419 | 3.9660 |
| | YB | Y384 | K421 | 5.4790 |

| | pair | aa | | D* |
|---|---|---|---|---|
| B (3,7) | ZJ | F210 | E211 | 3.4600 |
| | ZJ | F210 | E381 | 6.7250 |
| | PP | P212 | P214 | 6.5010 |
| | PB | P212 | R252 | 7.6690 |
| | PB | P214 | R252 | 5.6350 |
| C (2,5) | CB | C378 | R444 | 6.3270 |
| | GZ | G379 | F382 | 6.9630 |
| | GZ | G379 | F383 | 7.8310 |
| D (1,4) | ZJ | W395 | E466 | 7.7220 |
| | ZJ | W395 | E464 | 7.0190 |
| | ZJ | F396 | E464 | 7.9880 |
| E (1,3) | BC | K227 | C247 | 7.8300 |
| | BC | K227 | C239 | 7.9820 |
| F (1,3) | AX | A336 | N339 | 4.8530 |
| | AX | A336 | N340 | 6.2050 |
| G (1,3) | ZJ | F277 | D279 | 4.6620 |
| | ZJ | F277 | E351 | 7.1990 |

FIGURE 10A
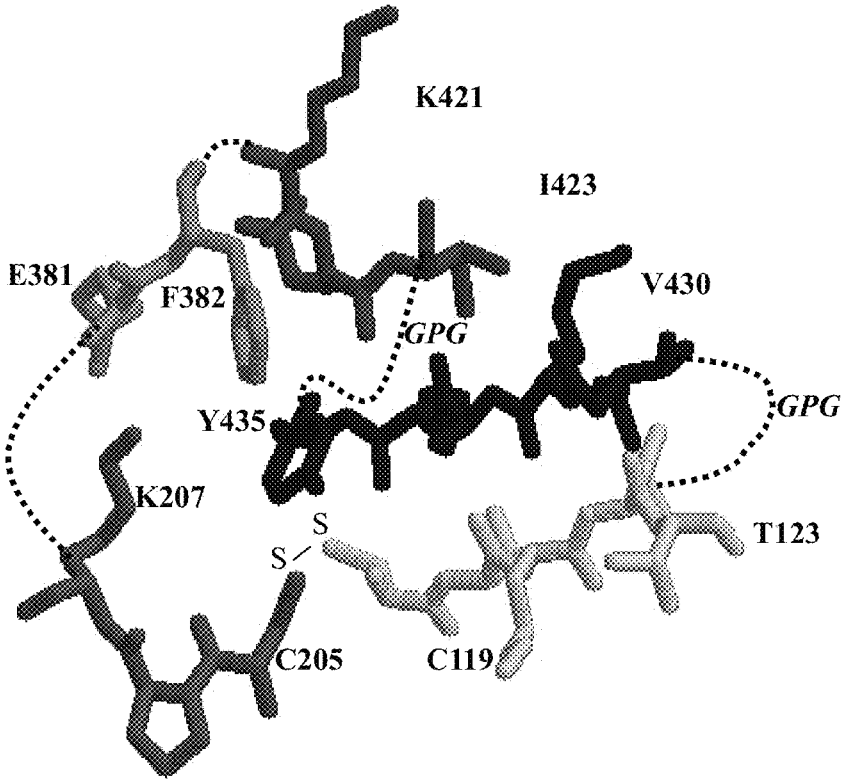
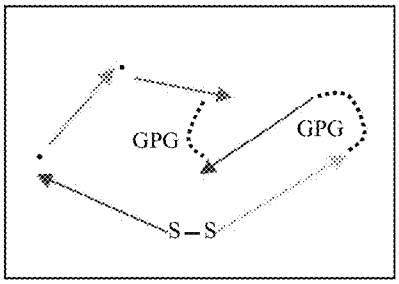
FIGURE 10B
FIGURE 10C
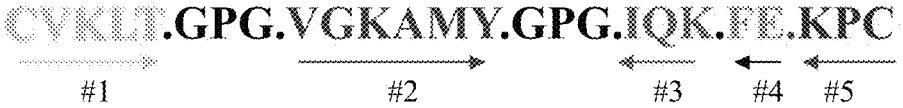

FIGURE 11A

HSFGDLSISPNSLTAWPGTL
WLMRAAWPWDYT
NLRSTSFFELWAKWP
GEFPDWDNLPLLCEG
GRPQWYLQFEDYWRS
DSLRVDEHHEVWVPM
DWVPFFGFFFSRLQLP
NWPRWWEEFVDKHSS
VRFHLAGWLPAVVSFVIFSDH
DGLRSDGSWLARFVFNGSGFY
GNFTASTASWGDELLALY
FVWEEHVGFLMRN
NWPRWEEFVDKHSS
FAHEGSASFRLSSKVEDWVSR
CVFYANVEEEVQCWL
FCVRLMCSGLIPFFVLCCFFA
FSRADFFPLSYSLSSVPSTAL
FSPYPPDIVHTTAFSSFVNPVD
SSFFYSALTPSFPSPYSQSSR
RFFAFPMVCASFFLVAIAFFP
PLPPSRFFITVCLTFLFSLSFF
VRPCVASLLLFFCLLFLLLPS
ICFPFNTRYCIFAMMVSSLVF
QQAGSYPGCIDYYYCHASAIG
CLPAYGCKSFREPF
RHFVPLYLSVSYDGFSRGASI
PIIHPHPPRIAMRVSISPFP
TPTDSTVRGSSTMDGFLKSVY
TASFWRSVSFPWVLSFLAFSH
GAQVNRKCAWHPRHI
VAKKLWVPQVSGSNF
HWGVYR
REKRWIFSDLTHTCI
TCLWSDLRAQCI

FIGURE 11B

```
HO OZ ZG GJ JU UO OU UO OP PX XO OU UO OA AZ ZP PG GO OU
ZU UM MB BA AA AZ ZP PZ ZJ JY YO
XU UB BO OO OO OZ ZZ ZJ JU UZ ZA AB BZ ZP
GJ JZ ZP PJ JZ ZJ JX XU UP PU UU UC CJ JG
GB BP PX XZ ZY YU UX XZ ZJ JJ JY YZ ZB BO
JO OU UB BU UJ JJ JH HH HJ JU UZ ZU UP PM
JZ ZU UP PZ ZZ ZG GZ ZZ ZZ ZO OB BU UX XU UP
XZ ZP PB BZ ZZ ZJ JJ JZ ZU UJ JB BH HO OO
UB BZ ZH HU UA AG GZ ZU UP PA AU UU UO OZ ZU UU UZ ZO OJ JH
JG GU UB BO OJ JG GO OZ ZU UA AB BZ ZU UZ ZX XG GO OG GZ ZY
GX XZ ZO OA AO OO OA AO OZ ZG GJ JJ JU UU UA AU UY
ZU UZ ZJ JJ JH HU UG GZ ZU UM MB BX
XZ ZP PB BZ ZJ JJ JZ ZU UJ JB BH HO OO
ZA AH HJ JG GO OA AO OZ ZB BU UO OO OB BU UJ JJ JZ ZU UO OB
CU UZ ZY YA AX XU UJ JJ JJ JU UX XC CZ ZU
ZC CU UB BU UM MC CO OG GU UU UP PZ ZZ ZU UU UC CC CZ ZZ ZA
ZO OB BA AJ JZ ZZ ZP PU UO OY YO OU UO OO OU UP PO OO OA AU
ZO OP PY YP PP PJ JU UU UH HO OO OA AZ ZO OO OZ ZU UX XP PU UJ
OO OZ ZZ ZY YO OA AU UO OP PO OZ ZP PO OP PY YO OX XO OO OB
BZ ZZ ZA AZ ZP PM MU UC CA AO OZ ZZ ZU UU UA AU UA AZ ZZ ZP
PU UP PP PO OB BZ ZZ ZU UO OU UC CU UO OZ ZU UZ ZO OU UO OZ ZZ
UB BP PC CU UA AO OU UU UU UZ ZZ ZC CU UU UZ ZU UU UU UP PO
UC CZ ZP PZ ZX XO OB BY YC CU UZ ZA AM MM MU UO OO OU UU UZ
XX XA AG GO OY YP PG GC CU UJ JY YY YY YC CH HA AO OA AU UG
CU UP PA AY YG GC CB BO OZ ZB BJ JP PZ
BH HZ ZU UP PU UY YU UO OU UO OY YJ JG GZ ZO OB BG GA AO OU
PU UU UH HP PH HP PP PB BU UA AM MB BU UO OU UO OP PZ ZP
OP PO OJ JO OO OU UB BG GO OO OO OM MJ JG GZ ZU UB BO OU UY
OA AO OZ ZZ ZB BO OU UO OZ ZP PZ ZU UU UO OZ ZU UA AZ ZO OH
GA AX XU UX XB BB BC CA AZ ZH HP PB BH HU
UA AB BB BU UZ ZU UP PX XU UO OG GO OX XZ
HZ ZG GU UY YB
RJ JB BR RZ ZU UF FO OJ JU UO OH HO OC CU
OC CU UZ ZO OJ JU UR RA AX XC CU
```

FIGURE 11C

| | | | | | |
|---|---|---|---|---|---|
| ZU | 25 | OY | 3 | YP | 2 |
| UO | 21 | GU | 3 | PY | 2 |
| ZP | 13 | AB | 3 | PJ | 2 |
| UP | 12 | OG | 3 | PM | 2 |
| ZO | 11 | JY | 3 | ZH | 2 |
| CU | 11 | XO | 3 | UH | 2 |
| JJ | 9 | JH | 3 | AA | 1 |
| UA | 9 | PX | 3 | XP | 1 |
| OA | 9 | BB | 3 | CC | 1 |
| UB | 9 | HU | 3 | CO | 1 |
| BU | 8 | GJ | 3 | MC | 1 |
| OB | 8 | CZ | 3 | PC | 1 |
| AO | 8 | MB | 3 | BY | 1 |
| BZ | 8 | UM | 3 | CJ | 1 |
| JU | 8 | JB | 3 | YA | 1 |
| GO | 7 | AX | 3 | MM | 1 |
| PZ | 7 | BA | 3 | XX | 1 |
| JZ | 7 | PP | 3 | XA | 1 |
| AZ | 7 | HP | 3 | AJ | 1 |
| UJ | 7 | AG | 2 | AH | 1 |
| ZJ | 7 | PA | 2 | CH | 1 |
| BO | 6 | OH | 2 | HA | 1 |
| XU | 6 | JO | 2 | AY | 1 |
| JG | 6 | PG | 2 | YG | 1 |
| OP | 6 | ZX | 2 | CB | 1 |
| AU | 6 | GA | 2 | BX | 1 |
| XZ | 6 | YU | 2 | JP | 1 |
| PU | 6 | BG | 2 | GB | 1 |
| PO | 6 | BP | 2 | YJ | 1 |
| GZ | 6 | HZ | 2 | GX | 1 |
| OJ | 5 | UG | 2 | XG | 1 |
| HO | 5 | BJ | 2 | YZ | 1 |
| ZA | 5 | YY | 2 | PH | 1 |
| UC | 5 | GC | 2 | OM | 1 |
| UX | 5 | AM | 2 | MJ | 1 |
| ZG | 4 | YC | 2 | HH | 1 |
| UY | 4 | XC | 2 | XB | 1 |
| YO | 4 | HJ | 2 | JX | 1 |
| PB | 4 | ZC | 2 | BC | 1 |
| ZB | 4 | CA | 2 | YB | 1 |
| ZY | 4 | MU | 2 | | |
| BH | 4 | OX | 2 | | |

CLUSTER A

CLUSTER B

CLUSTER C - Front

CLUSTER C - Back

CLUSTER D

FIGURE 14 A
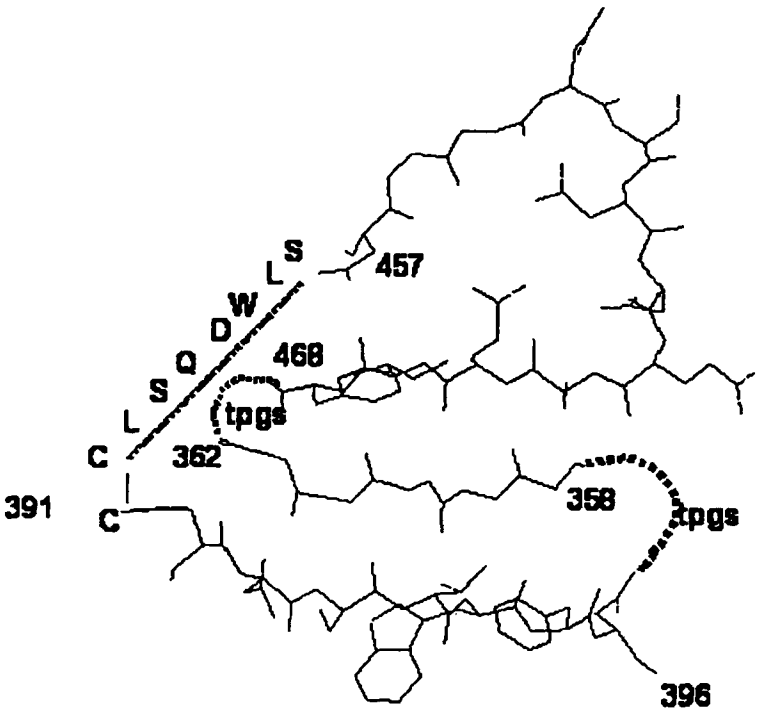
FIGURE 14 B
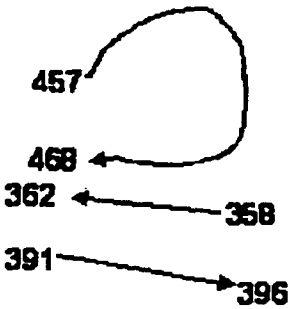
FIGURE 14 C
CFNSTWFNtpgsTIIFKtpgsFIESENNSNGGDSLWDQSLC FIGURE 15A
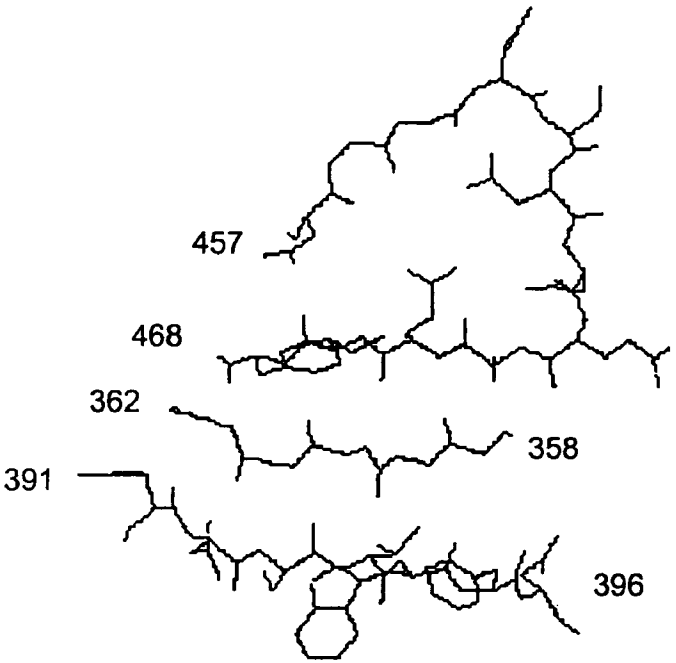
FIGURE 15B
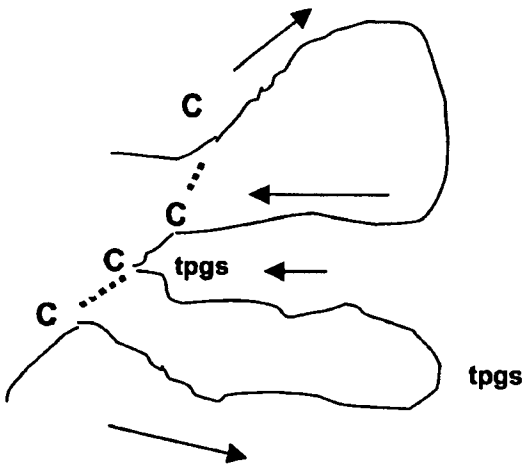
FIGURE 15C
CFNSTWFNtpgsTIIFKCtpgsCFIESENNSNGGDC

MAPPING AND RECONSTITUTION OF A CONFORMATIONAL DISCONTINUOUS BINDING SURFACE

Matter enclosed in heavy brackets [ ] appears in the original patent but forms no part of this reissue specification; matter printed in italics indicates the additions made by reissue.

FIELD OF THE INVENTION

The present invention is directed to a method for the discovery of the structure of conformational, discontinuous binding surfaces that associate with a binding molecule, preferably the epitopes of monoclonal antibodies (mAbs). More particularly, the binding molecule, such as a mAb, is used to select specific peptides from a peptide library that, in turn, are used as a binding surface (epitope) defining database that is applied via a novel computer algorithm to analyze the crystalline-structure of the original binding surface (antigen). The algorithm is based on the following: (1) most contacts between a mAb and an antigen are through side-chain atoms of the residues; (2) in the three-dimensional structure of a protein, amino acids remote in linear sequence can juxtapose to one another through folding; (3) tandem amino acids of the selected phage-displayed peptides can represent pairs of juxtaposed amino acids of the antigen; (4) contact-residues of the epitope are accessible to the antigen surface; and (5) the most frequent tandem pairs of amino acids in the selected phage-displayed peptides can reflect pairs of juxtaposed amino acids of the epitope. Application of the algorithm enables prediction of epitopes. The present invention is further directed to the reconstitution of an antigenic epitope-mimetic that is recognized by its original mAb, based on the segments of the epitope identified in the prediction. More specifically, the present invention is directed to antigenic epitope-mimetics for gp120 that may be used as a vaccine to raise broadly neutralizing antibodies for the prevention and treatment of HIV.

BACKGROUND OF THE INVENTION

The prediction of antigenic determinants is a difficult and uncertain task. Antibody:antigen interfaces have been generally assumed to be hydrophilic and transiently accessible to the surrounding milieu bathing the antigen and, as such, distinct from the subunit:subunit interface of multimeric protein complexes. These assumptions were the basis for the original Hopp and Woods predictive algorithm that sought to identify hydrophilic stretches in the protein linear sequence (Hopp, 1993). This was accomplished by assigning a hydrophilicity value for each of the 20 amino acids and calculating an average score for hexapeptides along the sequence of the antigen. Since then, numerous improved predictive algorithms have been published (Hopp, 1993; Hofmann et al, 1987; Pauletti et al, 1985; Van Regenmortel et al, 1994). Measuring the partition of model synthetic peptides in HPLC analyses has developed empirical hydrophilic values (Parker et al, 1986). Parameters for flexibility (Hopp, 1984), accessibility (Jones et al, 1997) and even antigenicity (Welling et al, 1985) have been introduced in an effort to increase the success rate for accurate prediction of binding surfaces (Van Regenmortel, 1999). Van Regenmortel, who has contributed much to this field, has published numerous detailed and comprehensive reviews and comparisons of predictive algorithms (see, for example, Van Regenmortel, 1999).

The essence of these studies goes towards attempting to learn the fundamental rules for biorecognition and to apply this knowledge to discover potential epitopes of a given antigen. The initial approach has dealt with the linear aspect of protein antigens and is unable to address the more realistic situation of conformational epitopes. Ninety percent of all epitopes are predicted to be discontinuous and highly conformational (Van Regenmortel, 1996). Van Regenmortel has argued that even a three dimensional analysis is still insufficient as one must also consider the fourth dimension—time, which plays a role in the conformational induced-fit of the epitope to better conform to its corresponding paratope of the antibody, and vice versa (Van Regenmortel, 1996).

A major step forward in understanding the nature of the epitope has been due to the co-crystallization of antibody: antigen complexes and solution of their structures at high resolution. Thus, as opposed to the original notion that antigen binding surfaces should comprise only 5-7 amino acid residues (Kabat, 1968), B cell-epitopes are now considered to contain 15-20 residues derived from 2-5 peptide segments of the antigen, occupying a surface of 700-900 $Å^2$ (Lo Conte, 1999; Chakrabarti et al, 2002; Jones et al, 1997). Furthermore, epitopes have been found to incorporate hydrophobic and aromatic residues in addition to hydrophilic and charged amino acids (Glaser et al, 2001). The degree of conformational comp33333lementarity between the epitope and paratope is less complete than might have been expected and water molecules play a significant role in bridging the binding surfaces and "filling-in the gaps" (Xu et al, 1997).

An effective humoral response towards an infectious agent is the ability of antibodies to bind and inactivate the pathogen. Vaccines, designed to induce the production of such antibodies, are typically derivatives of the pathogen, i.e., killed whole cells, attenuated live pathogens, fragments of antigens or DNA corresponding to the latter (Ellis et al, 2001; Hansson et al, 2000). Whatever the modality, the purpose of the vaccine is to stimulate neutralizing immunity in the naive individual in preparation of future encounters with fully virulent field-isolates of the pathogen. Correspondence between the vaccine and the field-isolate of the pathogen must be substantial, therefore, to ensure its efficacy. In cases where the pathogen undergoes extensive genetic variation, the ability to formulate an effective vaccine may present what appears to be an insurmountable obstacle. Such seems to be the case, for example, for HIV-1, the etiological agent of the AIDS epidemic, that is continuously selected for its ability to evade immune surveillance (Burton et al, 1998; Montefiori et al, 1999; Hoffman-Lehman et al, 2002).

HIV-1, as a result of each infectious cycle, accumulates numerous random mutations providing it with an endless source of variants (Wang et al, 2002; Moore et al, 2001). Nonetheless, over the years a few examples of highly cross-reactive and neutralizing monoclonal anti-HIV antibodies have been described—illustrating that protective immunity is possible (Mascola et al, 1999; Gauduin et al, 1997; Burton et al, 1994; Zwick et al, 2001b; Muster et al, 1993; Trkola et al, 1996; Conley et al, 1994; Van Regenmortel, 1996). This has been substantiated by experiments in which cocktails of mixtures of these mAbs, administered as passive immunotherapy, have proven effective in preventing the infection of CD4+ lymphocytes both in vitro and in vivo (Mascola et al, 1999: Gauduin, 1997).

Thus, a rational approach to the design of a cross-reactive antibody response against AIDS can be proposed as follows:

First, one must accumulate a collection of genuine broadly cross-reactive and neutralizing mAbs (to date at least 4 exist (Burton et al, 1994; Zwick et al, 2001b; Muster et al, 1993; Trkola et al, 1996; Conley et al, 1994)).

These, in turn, are used to discover their corresponding epitopes within the antigens of HIV-1.

Once mapped, the epitopes are to be reconstituted as synthetic versions that must be both antigenic (i.e., recognized by the original mAbs) and immunogenic (i.e., able to elicit in the naive individual the production of antibodies that are as effective as the original mAbs themselves).

Unfortunately, such a protocol turns out to be a very difficult task as the "interesting" mAbs against HIV-1 (and in fact against most pathogens) typically correspond to highly conformational epitopes that are comprised of discontinuous segments of the viral antigen (Van Regenmortel et al, 1996). Very often, even linear epitopes show conformational preferences and dependence on the context of a protein antigen (Ho et al, 2002). Thus, one is faced with a fundamental problem, namely: how can one discover the precise molecular design of conformational discontinuous epitopes of highly desirable mAbs of clinical importance?

SUMMARY OF THE INVENTION

Accordingly, it is an object of the present invention to solve the problems of the prior art.

It is a further object of the present invention to discover the molecular design of conformational discontinuous epitopes of highly desirable monoclonal antibodies of clinical importance.

It is another object of the present invention to predict the region on the surface of a proteinaceous material representing a basic element of a binding surface that associates with a predetermined binding molecule.

It is yet another object of the present invention to identify the basic elements of a binding surface on a proteinaceous material, which binding surface associates with a predetermined binding molecule.

It is still another object of the present invention to provide a method of producing a binding surface mimetic.

It is still a further object of the present invention to provide a pharmaceutical composition including one or more of the basic elements of the binding surface of gp120 that is recognized by a broadly neutralizing antibody.

It is still another object of the present invention to provide a molecule mimetic of the binding surface of gp120 that is recognized by a broadly neutralizing antibody.

More specifically, in one embodiment, the present invention is directed to a method for improved prediction of the region on the surface of a proteinaceous material representing a basic element of a binding surface that associates with a predetermined binding molecule comprising:

(a) screening a peptide library with said predetermined binding molecule to identify a plurality of peptides that bind to said binding molecule;

(b) determining the amino acid sequence of each identified peptide;

(c) assigning a symbol to each class of amino acid residue represented in the library and presenting each said sequence as a string of said symbols;

(d) calculating the frequency of occurrences of each tandem pair of symbols that exist in the strings of symbols presented in step (c);

(e) identifying those tandem pairs of symbols, the number of occurrences of which is statistically significant;

(f) mapping on a three-dimensional model of the proteinaceous material those pairs of amino acids represented by the tandem pairs of symbols identified in step (e), wherein a pair of amino acids is two amino acids, each of which are accessible to the surface of the proteinaceous material and whose alpha carbons are separated by no more than a predetermined distance; and (g) determining clusters of amino acid pairs mapped in (f), each amino acid pair in the cluster being topographically related to at least one other pair in the cluster.

Each cluster that is determined in step (g) is a predicted region on the surface of the proteinaceous material representing the binding surface.

The present invention is further directed toward identifying the basic elements of such a binding surface. First, a cluster is identified by the method for improved prediction discussed above. Next, the outermost amino acids of binding pairs in the cluster are identified so as to define the perimeter of the predicted binding surface. All other amino acids on the surface of the proteinaceous material that are situated within the perimeter of the predicted binding surface, or that are within a predetermined distance therefrom, are then also identified. Finally, the basic elements of the binding surface are identified in which each such element is a linear segment of the proteinaceous material whose first and last residues are amino acids previously identified, and none of the intermediate amino acids thereof are amino acids on the surface of the proteinaceous material not so identified. Any amino acid so identified that is not part of such a linear segment is considered to be a basic element consisting of a single amino acid.

The basic elements so identified may be used to produce a binding surface mimetic by connecting the basic elements in such a manner as to maintain the relative spatial orientation of the amino acids of the basic elements, thereby identifying a molecule that is mimetic of said binding surface. That mimetic molecule may then be produced.

An important broadly neutralizing antibody that interacts with the CD4 binding site on HIV-I surface glycoprotein gp120 and neutralizes many primary and TCLA viruses very efficiently is mAb b12 (Burton et al, 1994). Peptides identified by phage library screening have been identified in Zwick et al (2001a) and Boots et al (1997). The algorithm of the present invention can be applied to these previously-disclosed peptides in order to predict two clusters of amino acid pairs that may represent the binding surface recognized by this antibody and, from that, to identify the basic elements thereof and produce binding surface mimetic molecules that are expected to be recognized by this antibody. Thus, another embodiment of the present invention is directed to a pharmaceutical composition including one or more of the basic elements of the binding surface of gp120 that is recognized by mAb b12, which composition comprises a pharmaceutically acceptable carrier and one or more peptides selected from the group consisting of amino acids 254-257 of SEQ ID NO:1, amino acids 368-376 of SEQ ID NO:1, amino acids 382-386 of SEQ ID NO:1, and amino acids 418-424 of SEQ ID NO:1, which make up Cluster B. Alternatively, a cluster of peptides (Cluster A) that may also raise broadly neutralizing antibodies may be one or more peptides selected from the group consisting of amino acids 358-361 of SEQ ID NO:1, amino acids 391-396 of SEQ ID NO:1, and amino acids 455-468 of SEQ ID NO:1. The composition may further include a peptide of amino acids 115-120 of SEQ ID NO:1 (Cluster C).

One preferred embodiment of the present invention relates to a molecule mimetic of the binding surface of gp120 that is recognized by mAb b12 that is obtained by connecting two or more of the peptides of each of Clusters A and B mentioned in the previous paragraph, each in forward or reverse sequence, in such a manner as to form single molecules that maintain the spatial orientation that the amino acids thereof have when they are positioned at the positions at which they appear in gp120. In a further preferred embodiment, even one of the binding elements can be displayed in such a manner as to substantially maintain the relative spatial orientation thereof.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A shows the sequences of inserts of eleven phages (SEQ ID NOs:2-12, respectively) selected by screening phage display peptide libraries with mAb 17b. FIG. 2B shows pair composition of 17b phage inserts. FIG. 2C shows the amino acid pairs ranked according to their occurrences in the 17b-specific peptides.

FIG. 3A shows random frequencies (%) of amino acid pairs in the phage display peptide library that were calculated by multiplying the frequencies of amino acids in each pair. Random frequencies of amino acids in phage display peptide library inserts are shown in parentheses.

FIG. 4A shows clusters of 17b epitope pairs. In the column "Pair", amino acids (in single letter codes) are presented which were identified by the algorithm as located on a surface of the protein antigen at close distance (shown in the column D). In the column "aa", the numbers of these amino acids in the gp120 sequence (SEQ ID NO:1) and their 3-letter codes are presented. These amino acid pairs form "connected clusters". Horizontal lines divide the different clusters. Within the parentheses, the first number is the number of pair types, the second is the number of different amino acids in a cluster. D is the distance between backbone atoms in Å, and aa is amino acids. In FIGS. 4C and 4E, ribbon presentations of genuine and predicted epitope elements, respectively, are shown. Grey represents either non-predicted or non-contact residues, and black represents either predicted or contact residues.

FIGS. 5A-C show the analysis of the 13b5 mAb. FIG. 5A shows the sequences of inserts of sixteen phages (SEQ ID NOs:13-28, respectively) selected by screening phage display peptide libraries with mAb 13b5. FIG. 5B shows the pair composition of 13b5 phage inserts. FIG. 5C shows clusters of 13b5 epitope pairs. In the column marked "Pair", amino acids (in single letter codes) are presented which were identified by the algorithm as located on a surface of the protein antigen at close distance (shown in the column D). In the column marked "aa", the numbers of these amino acids and their one-letter names are presented. These amino acid pairs form "connected clusters". Horizontal lines divide the different clusters. In parentheses: the first number is the number of pair types, the second the number of different amino acids in a cluster. "D" is the distance between backbone (alpha carbon) atoms in Å.

FIG. 6 shows the comparison of CDR-loop sequences of 17b and CG10 mAbs (SEQ ID NOs:29-40 as designated in the figure). Coinciding residues are shown in bold.

FIG. 7A shows sequences (SEQ ID NOs:41-68) of inserts of phages selected by screening phage display peptide libraries with the CG10 mAb. FIG. 7B shows the pair composition of CG10 phage inserts. FIG. 7C shows the amino acid pairs ranked according to their occurrences in the CG10-specific peptides.

FIG. 8 is a cluster analysis of the CG10 epitope. The first number in the parentheses is the number of pair types, the second is the number of different amino acids in a cluster. "D" is the distance between backbone atoms in Å, and aa is amino acids.

FIG. 9A is a comparison of the 17b and predicted CG10 epitopes. White—amino acid residues exclusive to the 17b epitope; black—amino acid residues predicted only for the CG10 epitope; grey—amino acid residues shared by both epitopes. FIG. 9B is a three-dimensional model of gp120 where "cluster A" predicted by computer algorithm is displayed as space fill amino acids. FIG. 9C is a mutational analysis of the CG10 epitope (adapted from Rizzuto et al, 1998). Note that five residues circled in FIG. 9C were predicted as is shown in FIG. 9B.

FIGS. 10A-C are a reconstitution of the CG10 epitope. FIG. 10A shows four peptide fragments (residues 119-123, 430-435, 421-423 and 205-207, respectively, of SEQ ID NO:1) of the CG10 epitope according to the prediction, connected by GPG linkers, with an additional 381-382 fragment added for conformational requirements. In FIG. 10B, directions (from N-terminus to C-terminus) are shown. The sequence of the reconstituted epitope (SEQ ID NO:69) is presented in FIG. 10C.

FIG. 11A shows sequences (SEQ ID NOs:70-103) of inserts of phages selected by screening phage display libraries with the b12 mAb. FIG. 11B shows the pair composition of b12 phage inserts. FIG. 11C shows the amino acid pairs ranked according to their occurrence in the b12-specific peptides.

FIGS. 14A-14C are a reconstitution of the b12 epitope. FIG. 14A shows three peptide fragments of the b12 epitope according to the prediction, the first being residues 391-396 of SEQ ID NO:1, the second being 358-362 of SEQ ID NO:1, and the third being 457-468 of SEQ ID NO:1. The first and second fragments are linked by a TPGS (residues 9-12 of SEQ ID NO:104) linker, and the second and third fragments are linked by another TPGS (residues 18-21 of SEQ ID NO:104) linker. The third fragment is linked to the first, substantially maintaining the spatial orientation by a SLWDQSLC (residues 34-41 of SEQ ID NO:104) linker. In FIG. 14B, directions (from N-terminus to C-terminus) are shown. The sequence of the reconstituted epitope (SEQ ID NO:104) is presented in FIG. 14C.

FIGS. 15A-15C show a reconstitution of the b12 epitope that is a variation of that of FIGS. 14A-14C. FIG. 15A shows the three peptide fragments (residues 391-396, 358-362 and 457-468 of SEQ ID NO:1), linked by TPGS (residues 9-12 and 19-22 of SEQ ID NO:105) linkers, with double cysteine loops. In FIG. 15B, directions (from N-terminus to C-terminus) are shown, as well as the location of the disulfide bonds. The sequence of the reconstituted epitope (SEQ ID NO:105) is presented in FIG. 15C.

DETAILED DESCRIPTION OF PREFERRED EMBODIMENTS

Figure 1:
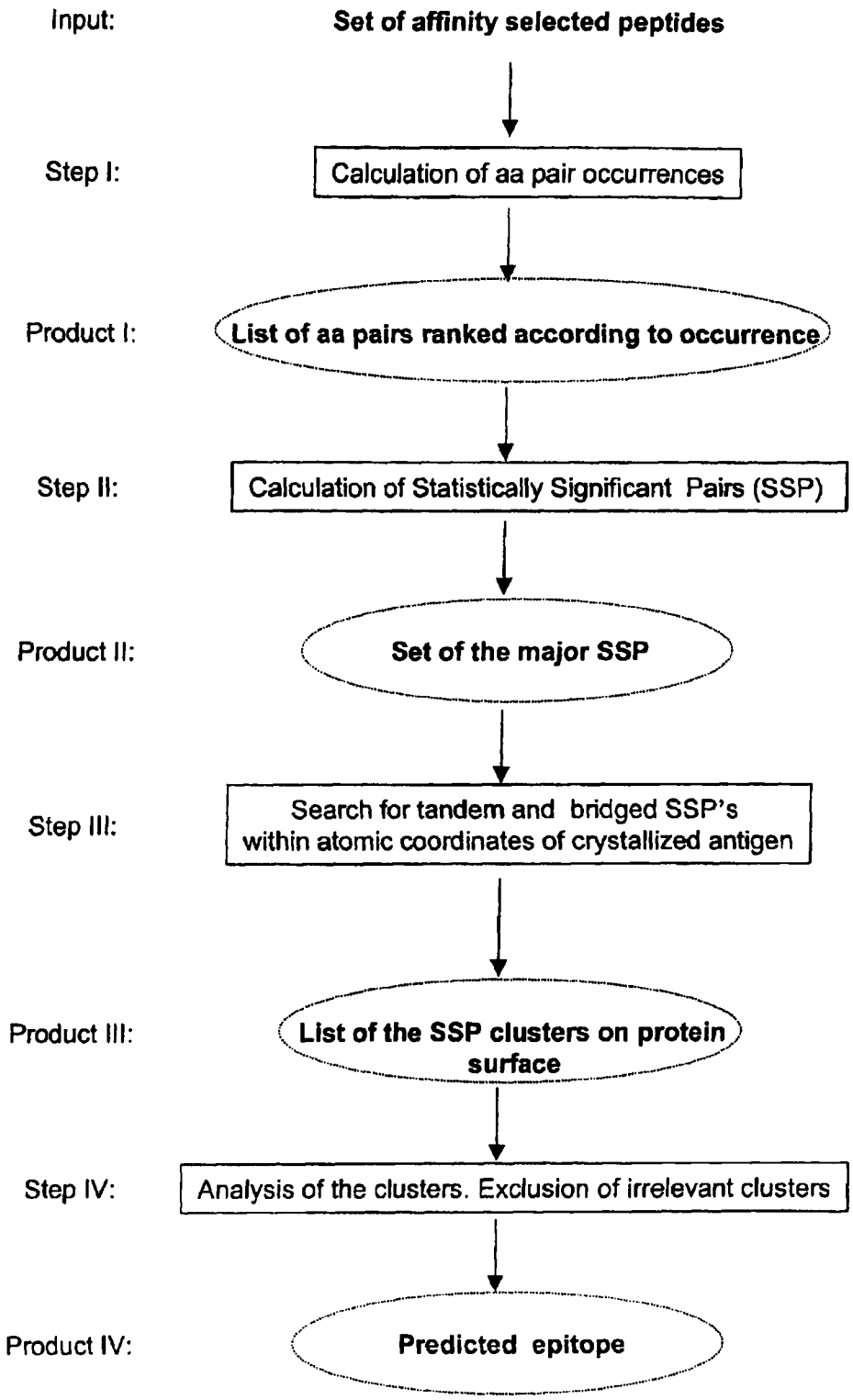
FIG. 1 shows a scheme of the algorithm used in the present invention.

As used throughout the present specification and claims, the following definitions apply:

A "binding surface" is that portion of a proteinaceous material that associates with a binding molecule.

A "proteinaceous material" is any protein, or fragment thereof, or complex containing one or more proteins formed by any means, such as covalent peptide bonds, disulfide bonds, chemical crosslinks, etc., or non-covalent associations, such as hydrogen bonding, van der Waal's contacts, electrostatic salt bridges, etc.

The "binding molecule" is any molecule, whether or not proteinaceous, that associates with a binding surface, i.e., binds to the binding surface with specificity dependent on the structure of that surface and with an affinity greater than $K_D=10^{-5}$ M. While the binding molecule-binding surface association is mainly discussed herein from the standpoint of the antibody-antigen association, such associations may be a ligand-receptor association, a receptor-hormone association, an enzyme-substrate association, or any other protein-protein interaction.

While the binding molecule may itself be a proteinaceous material, such as an antibody, an enzyme, a ligand, a receptor, etc., it is not necessarily proteinaceous. Thus, for example, the binding molecule may be a polynucleotide sequence or a sugar molecule, gangliosides, lipids, etc. Among examples of applications for the process of the present invention using non-proteinaceous binding molecules are the following. One may screen a peptide library with a complex glyco moiety for the purpose of identifying the active binding surface of a lectin specific for that sugar. Another example is screening with a specific DNA sequence for the discovery of the binding surface of transcription factors such as repressors or inducers of gene expression that bind to that surface. The active binding surface of any DNA binding protein may be found by this method.

In general, when the binding surface and the binding molecule are both proteinaceous materials, they may be interchangeable, such that either may be denominated the binding surface or the binding molecule. However, while the binding molecule need not be proteinaceous, the binding surface must be on a proteinaceous material. Thus, where one of the binding pairs is a proteinaceous material and the other is non-proteinaceous, the proteinaceous material is always considered to be the binding surface, and the non-proteinaceous material will always be considered to be the binding molecule.

A "peptide library" is a collection of peptides, preferably ranging from 5 to 25 amino acid residues in length. The collection of peptides may be a random collection or it may be rationally designed based on the composition of the proteinaceous material of which the binding surface is a part. The greater the number of different peptides in the library, the better. Preferably, in the case of a random peptide library, it should contain more than $10^7$ different peptides. An example of a rationally defined peptide library may be that disclosed in WO 98/20169.

In the peptide library, the peptides may be displayed by any means, such as, for example, peptides displayed on phage, a combinatorial library of synthetic peptides on beads, etc. Phage display libraries of random peptides are well known in the art. See, for example, Enshell-Seijffers et al (2002).

The term "statistically significant", when determining which tandem pairs of symbols are to be used for further processing, means that the number of occurrences of that tandem pair is greater than would be predicted from randomness by an amount that is statistically significant.

The term "three-dimensional model" means a calculated or predicted structure in which the XYZ coordinates of at least the alpha-carbon of each amino acid thereof is specified. An example of such a three-dimensional model would be a solved crystal structure or a structure determined by NMR-spectroscopy. Alternatively, a predicted structure can be derived by superimposition of an unknown structure onto a known structure.

The term "mapping" means identifying the physical location on the three-dimensional model of the identified amino acids.

The "predetermined distance" used in the mapping step is a function of the degree of stringency designed into the analysis. The greater the distance used, the poorer will be the resolution of the results. A preferred range is 5-15 Å.

A "cluster of amino acid pairs" is an identified group of amino acid pairs, each amino acid pair of which is topographically related to at least one other pair in the group. Two amino acid pairs are "topographically related" if they either share an amino acid residue or each has an amino acid residue that falls within a predetermined distance of one another. The predetermined distance must be greater than the amino acid difference that defines a pair of amino acids and may be as great as three times that distance. The preferred relationship is that in which the two amino acid pairs share a common amino acid. A cluster has two or more pairs of amino acids. Any cluster so identified is a predicated region on the surface of the proteinaceous material representing a basic element of the binding surface being sought. The greater the number of pairs of amino acids in the cluster, the greater the likelihood this cluster represents the binding surface or a significant portion thereof.

The present invention is a systematic approach designed to discover the precise molecular design of conformational, discontinuous binding surfaces, which are bound by highly desirable binding molecules. Preferably the binding surfaces are epitopes and the binding molecules are monoclonal antibodies (mAbs). It is based on using specific binding molecules, such as mAbs, to screen peptide libraries, such as combinatorial phage display peptide libraries. The binding molecule-specific phages are then used as a binding surface-defining database to which is applied a novel computer algorithm to analyze the crystalline structures of the proteinaceous material, of which the binding surface is a part. Thus, if the proteinaceous material is the gp120 envelope protein of HIV and the binding material is a mAb specific thereto, the mAb-specific phage may be used to analyze the crystal-like structure of the viral antigen. In this manner, candidate binding surface areas are mapped to the surface of the proteinaceous material. Based on this mapping, bona fide segments of the proteinaceous material are used independently or two or more used in combination to reconstitute the binding surface or components thereof, that are recognized by the original binding molecules, or which raise antibodies that block the binding of the original binding molecules to the gp120. Henceforth, the present specification will discuss the preferred embodiment in which the binding molecule is a mAb and the binding surface is an epitope. It should be understood, however, that other binding molecules may be substituted for mAbs and other binding surfaces for epitopes.

The development of the present invention was based on the assumption that affinity-selected peptides derived from a vast collection of random peptides, due to their specific binding to the mAb of interest, must reflect structural elements of the original epitope. Initially, this might appear to be a trivial assumption as one could expect to obtain peptides that show linear homologies with the immunogenic antigen. However, in the case of highly conformation-dependent mAbs, the peptides obtained are often diverse and lack obvious homology or relatedness with the original antigen (Felici et al. 1993; Folgori et al, 1994).

The first step, therefore, is to screen libraries so as to accumulate a diverse spectrum of peptides that bind to the binding molecule of the binding molecule-binding surface pair that is being studied. In the case of a mAb-epitope binding pair, these peptides will collectively provide insights to the molecular nature of the epitope recognized by the mAb.

Then, a systematic computer algorithm is used, which is described below, designed to focus on the common denominators of the peptides and use this information to map epitopes onto the surface of the solved crystalline structures of the antigens.

Once this is achieved, the discontinuous epitope can be reconstituted from the segments of the antigen that make up the original epitope.

As indicated above, the first step of the process of the present invention is to repeatedly screen combinatorial phage display peptide libraries (or other peptide libraries) using the monoclonal antibody (or other binding molecule) until a collection of peptides is obtained, each of which bind to the binding molecule. It is expected that 10-20 peptides will be identified in the course of such a screen, although fewer may suffice to make an accurate prediction, and the more that are found, the more accurate the prediction is expected to be. The amino acid sequence is then determined for each peptide identified in the screen as being capable of binding to the binding molecule, such as the mAb, used in the screen.

In order to derive the location of the binding surface on the proteinaceous material of interest, using the peptides identified in the screen, a novel computational algorithm has been developed. FIG. 1 is a general scheme of the final algorithm. The algorithm is based on the following considerations:

1. Most of the contacts made between a mAb and its antigen are through side-chain atoms of the residues, rather than through main-chain moieties. This is based on many studies, for example, the analysis of 19 different antibody-antigen complexes (81% of the contacts are contributed by side-chain atoms (Lo Conte et al, 1999)) and is specifically true for the 17b/gp120 complex for which >70% of the contacts are through the side-chains.

2. In the three-dimensional structure of a protein, amino acids remote in linear sequence can be juxtaposed to one another through folding. A conformational epitope of an antibody can consist of such amino acids and form a cluster of discontinuous amino acids that create a contiguous binding surface. A cluster can therefore contain residues that are tandem in sequence or residues brought together through folding.

3. Tandem amino acids of the selected phage-displayed peptides can represent pairs of juxtaposed amino acids of the binding surface of the antigen. It is assumed that phage displayed peptides, affinity selected via biopanning with the mAb of interest, represent partial structural elements of the epitope.

4. Contact residues of the epitope are accessible to the antigen surface.

5. The most frequent tandem pairs of amino acids in the selected phage-displayed peptides, are most likely to reflect pairs of juxtaposed amino acids of the clustered residues of the bona fide epitope.

Step I in the computer algorithm is to calculate the number of occurrences of specific amino acid pairs present in the affinity-selected peptides, and identify those pairs that are substantially over-represented as compared to the random frequencies of pairs statistically anticipated.

Calculation of random frequencies of amino acid pairs may be performed as follows. In the random library the frequency of amino acids should reflect the codon-usage employed in the generation of the corresponding random DNA oligonucleotides. For example, in the libraries prepared for the experiments reported in the following examples, a restricted codon-usage was applied in which any of the four phosphoramidites are possible for the first two positions of any codon; however, only G or T are provided for the third position. The reason for this was to avoid the stop codons UAA and UGA as well as to reduce the total redundancy of codons. Furthermore, in order to prevent abortive termination at stop codon UAG, the libraries were produced in bacteria containing a glutamic acid suppression mutation.

Each pair of residues may be analyzed for anticipated frequencies. However, as contacts between the mAb and the antigen are through functional moieties of the R-groups, a preferred embodiment is to consolidate conserved residues into functional subgroups of amino acids. An example of this is the consolidation into the following six functional subgroups, each of which is given single letter codes:

R,K=B
E,D=J
S,T=O
L,V,I=U

Q,N=X

W,F=Z.

The anticipated frequencies ($n_r$) of the amino acid pairs for totally random peptides are then calculated. In the above-described library, using the symbols represented by the single letter codes given above for grouped residues and the standard code of the remaining individual residues, the results of such a calculation are given in FIG. 3A. A similar analysis can readily be conducted for any other library that may be used.

Two types of pairs must be considered: completely random pairs, in which both partners of a pair are random and "semi-random" pairs in which only one partner is random, whereas the other is constant (as is in the case for the first and last pair of each peptide containing the constant flanking cysteine residues).

The amino acid sequences of the peptides found in the screen are first entered into the algorithm. The algorithm then assigns the corresponding symbol to each class of amino acid residue represented in the library and then presents each of the sequences as a string of such symbols. As indicated above, the symbols may be the common single-letter code for each residue or a symbol representing each of the functional subgroups of amino acids. Preferably, each sequence is presented as tandem pairs of said symbols. Thus, for example, if the first peptide is CSGLRNETFLRC (SEQ ID NO:2), the same sequence represented as a string of symbols that take into account the functional subgroups would be COGUBXJOZUBC. This sequence may be represented as the following tandem pairs of amino acid symbols: CO OG GU UB BX XJ JO OZ ZU UB BC.

Once all of the peptides found in the initial screen are presented as tandem pairs, the frequency of occurrences of each tandem pair of symbols that exists in the strings of symbols is calculated. This is simply done by counting the number of times each possible tandem pair appears in the list of tandem pairs that is generated from the sequences of the peptides found in the screen. Thus, for example, for the sequences found in Example 1, discussed below, shown in FIG. 2A, the tandem pairs of symbols are shown in FIG. 2B, and the number of occurrences for each amino acid pair of the eleven affinity-selected peptides were scored and listed according to their occurrences in FIG. 2C. This corresponds to "Product I" in FIG. 1.

The next step is to identify those tandem pairs of symbols, the number of occurrences of which is statistically significant. Thus, for example, if the number is no more than would be expected from a random appearance of such pairs, it is not considered to be statistically significant. The expected theoretical number of specific amino acid pairs ($f_r$) is calculated as the product of the theoretical frequency of a pair ($n_r$) and the total number of pairs in a specific set of peptides (A). Thus, the total number of tandem pairs (A) in FIG. 2B is 141. The anticipated frequency ($n_r$) of the most frequently found tandem pair, BU, can be seen from FIG. 3A as being 2.34%. Thus, the theoretical frequency ($f_r$) of BU in the 141 tandem pairs of FIG. 2B is 3.3, as can be seen in the stippled column above UB in FIG. 3B. Even taking into account random error, it is apparent that the experimental number of occurrences (10) is substantially greater than theoretical and, thus, the number of occurrences for UB is statistically significant. On the other hand, the experimental number of the BU tandem pair is not greater than the theoretical statistically significant amount. The number of standard deviations above randomness required for a given pair is defined as the Statistical Threshold, ST. This is a parameter which is controllable by the algorithm and can be set or varied by the operator.

The next step is to map, on a three-dimensional model of the proteinaceous material, those pairs of amino acids represented by the statistically significant tandem pairs of symbols. For the purpose of this mapping, a "pair of amino acids" is two amino acids, each of which are accessible to the surface of the proteinaceous material and whose alpha-carbons are separated by no more than a predetermined distance. While preferably both members of each pair are surface accessible, the algorithm may afford the possibility of including a pair for which only one of its members is surface accessible. Surface accessibility is determined by a third parameter E, surface accessability threshold. The accessibility of each amino acid may be calculated, for example, using the SurfRace software (Tsodikov et al., 2002), which can be assimilated into the algorithm software. This parameter is controlled by the algorithm and may be set or varied by the operator.

Preferably, the mapping is done by first preparing a database containing the physical distances between each pair of alpha-carbon atoms in the entire proteinaceous material. As the three-dimensional structure of the proteinaceous material has already been solved as a prerequisite to its use in the process of the present invention, it is readily within the skill of one of ordinary skill in the art to calculate the distance between any two alpha-carbons, repeat this for every possible pair, and then rank each pair in order of the distance between them. This is done without regard to whether or not the members of the pair are adjacent to one another in the linear sequence that makes up the proteinaceous material. This may be done by hand or by computer.

As indicated above, those pairs that are considered to be relevant in determining the binding surface are those having a separation of alpha-carbons less than a predetermined distance D. This distance parameter is controllable by the algorithm and can be set or varied by the operator.

Using the parameters defined above, amino acid pairs from the database of amino acid pairs of the proteinaceous material ranked by the distance separating them can be analyzed to determine which of those pairs is considered to be relevant. Each of the relevant pairs may then be mapped on the three-dimensional model of the proteinaceous material.

The next step is to determine clusters of those mapped relevant amino acid pairs, wherein each amino acid pair in the cluster is topographically related to at least one other pair in the cluster. Preferably, clustered pairs are determined by an appropriate rule of connectivity. For example, a cluster of pairs may be determined when a member of one pair can be connected to a member of a second pair, which, in turn, is connected to a third, and so forth. Two pairs are considered to be connected if they are topographically related. Two amino acid pairs are topographically related if they either share an amino acid residue or each has an amino acid residue that falls within a predetermined distance of one another. In either case, a tandem residue (i.e., linearly consecutive) to a predicted pair is considered to be topographically related if it also participates in a predicted pair. Thus, one rule of connectivity is to require that each pair actually share an amino acid residue (or a tandem residue) in order to be considered topographically related. In another embodiment, however, it is only necessary that each have an amino acid residue that falls within a predetermined distance of one another. The predetermined distance must be greater than the amino acid difference that defines a pair of amino acids used in determining what is a relevant amino acid pair when mapping the statistically significant amino acid pairs onto the surface of the three-dimensional model of the proteinaceous material. Thus, the predetermined distance for determining whether two amino acid pairs are topographically related may be as great as three times the distance defined above with respect to the mapping step. Thus, such a predetermined distance may preferably be 18-36 Å, although it could be as great as 45 Å.

A cluster has two or more pairs of amino acids as determined by the rule of connectivity that is used. Any cluster so identified is a predicted region on the surface of the proteinaceous material, representing at least a part of the binding surface being sought. The greater the number of pairs of amino acids in the cluster, the greater the likelihood this cluster represents the binding surface or a significant portion thereof. Each cluster identified by means of the process of the present invention is a predicted region on the surface of the proteinaceous material representing the binding surface.

Depending on the size and quality of the peptide panel, one can miss specific residues of the epitope that are contained within segments of the predicted clusters. Consider for example a prediction that contains residues #200 and #208 as well as all the residues between them except for #203 and #204. In such a case, two short peptides, 200-202 and 205-208 would be predicted separated by two non-predicted residues 203 and 204. The algorithm can include the entire segment 200-208 (9 amino acids) in its prediction, "filling in the gap" that stems from the missed residues. Therefore, a fourth parameter—I, defines the maximum gap (i.e., the number of non-predicted amino acids) between two residues to be connected. This parameter is also set or varied by the algorithm.

A preferred algorithm of the present invention is the algorithm that has been published by Enshell-Seijffers et al., 2003, which is entirely incorporated by reference herein.

In order to refine the precision of the prediction of the binding surface, a number of steps may optionally be taken. This is particularly useful in the situation that an analysis predicts a number of clusters within the antigen and one requires objective criteria to focus on the most physiologically relevant prediction.

As the first step, and as indicated above, the largest and most elaborate cluster, containing the largest number of different pairs and the largest number of different residues, is identified.

In order to further refine the prediction once one has screened the mAb with a given type of library (such as a linear p3 20 mer library) and obtained peptides and a prediction, a second screen can be conducted against a different type of library (e.g., constrained S-S 12 mer library) and another analysis conducted so as to try to identify overlapping clusters or segments of clusters. It could be concluded that the overlaps are more likely to be relevant than isolated individual clusters.

Another refinement involves conducting mutagenesis of the residues in the predicted clusters to identify those mutations that most affect the binding.

A further refinement would be to create mutations of the CDR loops of the mAb. If one is able to introduce a mutation that affects the binding of some of the peptides and not to the antigen, one can exclude the affected peptides from the analysis and see if the prediction now focuses more on a specific cluster.

Another possible refinement is to screen the peptides recognized by the mAb against polyclonal serum of relevant patients. It would be expected that peptides that most resemble (structurally or functionally) the bona fide epitopes of the pathogenic antigens would be recognized by polyclonal serum. The analysis of the present invention can then be conducted using the peptides that are recognized by more than the single original mAb.

Another refinement would be to try to obtain different mAbs that compete for the antigen against the original mAb. If any of the peptides from the original mAb are bound by the competing mAb, these peptides should be given more weight in the analysis.

Finally, the competing mAbs could be screened against peptide libraries in order to obtain new peptides. These can be used to conduct predictions and see if any new clusters coincide or overlap in part with the original clusters. Furthermore, if the competing antibodies produce peptides that are recognized by the original mAb, these should be given more weight in the analyses.

Once a cluster of amino acids is identified using the process of the present invention discussed above, this information may be used to identify a basic element of the binding surface on the proteinaceous material. The first step in accomplishing the identification of such a basic element is to analyze the amino acids of the cluster as mapped on the three-dimensional model of the proteinaceous material. The perimeter of the predicted binding surface is defined by identifying the outermost amino acids of the binding pairs in the cluster.

In the next step, one identifies all of the other amino acids on the surface of the proteinaceous material situated either within the perimeter of the predicted binding surface or within a perimeter that is extended from the positions of the outermost amino acids of the binding pairs in the cluster by a predetermined distance. Thai predetermined distance is preferably about the same as that described above in the context of the rules of connectivity, i.e., 18-36 Å, although it could be as great as 45 Å. Preferably, it is about 20 Å. Thus, all amino acids within the perimeter of the outermost amino acids of the binding pairs in the cluster or otherwise within a predetermined distance of one of those outermost amino acids, which predetermined distance is the same as that for finding relevant amino acid pairs, are all identified in this step.

Finally, linear segments of the proteinaceous material are identified according to the following requirements. The first and last residues of each such linear segment must be amino acid residues identified in either of the preceding two steps. None of the intermediate amino acids thereof are amino acids on the surface of the proteinaceous material not identified in either of the previous two steps. Each such linear segment is identified as being a basic element of the binding surface. In addition, any single amino acid identified in either of the previous two steps that is not a part of one of the linear segments identified herein are considered to be basic elements of a single amino acid each.

The "basic elements", which are determined using the analysis discussed above, may each be peptides having from one to twenty or more residues. The basic elements themselves have utility as follows:

(1) If they are to be immunogenic, either independently or when presented on a carrier, when administered in any of the standard procedures for immunization with a peptide (see for example, Van Regenmortal, 2001), one or more of them may be used as a vaccine with the expectation that antibodies raised against them will cross-react with the binding surface and cause neutralization, a mechanism similar to that by which the neutralizing binding molecule that one started with causes neutralization. Besides raising antibodies that might be neutralizing, the basic element itself might prevent the interaction of the proteinaceous material that is necessary for its activity with its target. The ability of such a basic element, or plurality of basic elements, to serve as such a vaccine may be determined by testing polyclonal antibodies raised thereby in an animal model in a competitive assay with the original neutralizing antibody. If such antibodies (or such antibodies after first being purified by affinity separation using the original immunogens), block the binding of the original neutralizing antibody to its substrate, then it is likely that such antibodies will also be neutralized and such immunogen then becomes a prime candidate for a vaccine.

(2) If the basic element is part of an enzymatic region, then the basic element may serve as an inhibitor of the enzymatic reaction by sequestering the substrate.

With respect to the first utility, one can assume that, if a functional antibody response is elicited against a segment of the epitope, that might suffice in interfering with virus infection or physiology. Thus, one might not have to functionally reconstitute the original surface to be recognized by the original monoclonal antibody to justify its use as a vaccine component.

While it may not be reasonably predictable that each binding element will function as a vaccine or have one of the other utilities discussed above, they have a much increased probability of such activity over a random peptide. One of skill in the art will readily be able to test each such binding element for the specified activity without engaging in undue experimentation, such as in the manner discussed above.

The basic elements previously identified may next be used in order to produce a molecule that is a binding surface mimetic.

When making a molecule mimetic of a binding surface, the peptides of the basic elements are connected in such a manner as to form a single molecule that substantially maintains the spatial orientation that the same amino acids have when part of the binding surface. The term "connected", in this sense, includes connecting the peptides by covalent bonds (peptide bond or other), directly to one another or indirectly by means of appropriate linkers selected so as to cause the molecule to maintain the desired spatial orientation. For example, a preferred linker used to impose a turn is GPG. A second linker that also imposes a turn is the tetrapeptide TPGS (residues 9-12 of SEQ ID NO:104). If one wants to force rigidity, one might introduce more proline residues. A more flexible and hydrophilic linker might contain glycines, serines and threonines.

When connecting the peptides, one or more of the peptides of the basic elements may need to be synthesized in reverse order so as to maintain the spatial orientation of the binding surface. Furthermore, extra residues from the underlying molecule that linearly extend the basic elements may be added to assist in creating the desired spatial orientation. The peptides may also be connected by means of non-peptide bonds, such as disulfide bonds. Examples of mimetic molecules connected in such a manner are discussed below with respect to the G12 mimetic, which is mimetic of the binding surface of gp120 recognized by the CG10 antibody, and with respect to the molecules that are mimetics of the binding surface of gp120 recognized by the b12 antibody.

The term "connected" in this context also includes grafting of the peptides onto a scaffold, which is essentially the same as the use of extended linkers. The grafting of loops onto a scaffold is common in the field of antibody modifications in which CDR-loop grafting is common practice. In CDR-loop grafting, CDR loops from one antibody are swapped onto a scaffold of another, a process required in humanization of murine antibodies to be used in pharmaceutical compositions in people. To find an appropriate scaffold for such grafting, one would screen the database of protein crystals to find spatial orientation structures on other proteins that are similar to the spatial orientation of the binding elements being connected. If such a structure is found, then the sequences of the peptides of the binding elements can be substituted at the corresponding positions of the scaffold.

Another example of a scaffold is to actually use the same proteinaceous material of which the binding surface is a part, which has been modified in such a manner as to accentuate the immunogenicity only of the binding surface. An example of this may be found in Pantophlet et al (2003). In this reference, hyperglycosylation is introduced into the gp120 so as to obscure some areas of the molecule and reveal others to become more immunogenic.

Once the peptides of the basic elements are identified, one can vary the sequence of those peptides to the extent that the corresponding portion of other cognate proteins may include such variability. Two proteins are "cognate" if they are produced in different species, but are sufficiently similar in structure and biological activity to be considered the equivalent proteins for those species. Two proteins may also be considered cognate if they have at least 50% amino acid sequence identity (when globally aligned with a pam250 scoring matrix with a gap penalty of the form q+r(k−1) where k is the length of the gap, q=−12 and r=−4; percent identity=number of identities as percentage of length of shorter sequence) and at least one biological activity in common. Similarly, two genes are cognate if they are expressed in different species and encode cognate proteins.

For example, the proteinaceous material used in the examples of the present application is gp120. One can vary the sequence of the peptides of the basic element reported herein to the extent that the corresponding portions of other isolates of gp120 may include such variability. Thus, the gp120 sequence of SEQ ID NO:1, which is used throughout the present specification, is the sequence of HXB2 isolate. Many other isolates of gp120 are known and whose sequences are known, which isolates represent the extensive number of sub-types of HIV. Table 1, for example, is a comparison of the sequences of the basic elements of the b12 binding surface of HXB2 (which is a clade B isolate) and the consensus sequence for each of clades A-G and O. It can be seen that many of the residues are highly conserved while others are quite variable.

TABLE 1

Comparison between the Cluster A Segments of the B12 Epitope of HXB2 with the Corresponding Positions in the Consensus Sequences of Various HIV-1 Clades

| Clade | 391-396 | SEQ ID NO | Clade | 360-362 |
|---|---|---|---|---|
| Hxb2 | F N S T W F | 1 | Hxb2 | I F K |
| A | F N S T W N | 108 | A | I F T |
| A1 | F N S T W N | 108 | A1 | I F T |
| A2 | F N S T W ? | 109 | A2 | I F T |
| B | F N S T W N | 108 | B | V F N |
| C | F N S T Y N | 110 | C | K F A |
| D | F N S T W N | 108 | D | I F K |
| F1 | F N D T G S | 111 | F1 | K F N |
| F2 | F N N T E V | 112 | F2 | T F N |
| G | F N N S I L | 113 | G | T F N |
| O | F N Y T F S | 114 | O | I F N |

TABLE 1-continued

Comparison between the Cluster A Segments of the B12 Epitope of HXB2 with the Corresponding Positions in the Consensus Sequences of Various HIV-1 Clades

| | | | | |
|---|---|---|---|---|
| O1 | F N N T<br>C I | 115 | O1 | I F Q |
| O2 | F N S T<br>W N | 108 | O2 | I F A |
| O3 | F N S T<br>W N | 108 | O3 | V F N |
| O4 | F N S T<br>Y M | 116 | O4 | ? F A |
| O6 | F N ? S<br>I ? | 117 | O6 | T F N |
| O8 | F N G T<br>Y ? | 118 | O8 | K F A |

| Clade | 457-468 | SEQ ID NO |
|---|---|---|
| Hxb2 | D G G N S - - - - - - - - N N E S E I F | 1 |
| A | D G G V N - - - - - ? ? ? N S ? N E T F | 119 |
| A1 | D G G V N - - - - - ? ? ? N S ? N E T F | 119 |
| A2 | D G G ? N - - - - - - - - ? ? ? N E T F | 120 |
| B | D G G N N ? ? ? ? ? ? ? ? T N T T E I F | 121 |
| C | D G G N N - ? ? ? ? ? ? ? T N T T E T F | 122 |
| D | D G G A N - ? ? - ? ? ? ? N S S N E T F | 123 |
| F1 | D G G Q ? - - - - - - ? ? ? S ? T E T F | 124 |
| F2 | D G G K N - - - - - - - - ? N G S E T L | 125 |
| G | D G G N N - ? - - - ? ? ? T S T N E T F | 126 |
| O | D N P W N - ? - - - ? ? T S N ? N A T F | 127 |
| O1 | D G G A N - ? - - - ? ? ? N T T N E T F | 128 |
| O2 | D G G N N - - - - - - ? ? N S T N E T F | 129 |
| O3 | D G G N Q - - - - - - - - S N V T E I F | 130 |
| O4 | D G G ? ? - - - - ? ? ? ? ? ? ? N E T F | 131 |
| O6 | D G N N ? - - - - - - - - ? S ? S E T F | 132 |
| O8 | D G G R T - - - - - - ? E S N D T E I F | 133 |

Data obtained from the website found at hiv-web.lanl.gov ?: variable positions, -: no residue at this position Table 2, hereinbelow, is an illustration of an example of anticipated variations in the sequence of the basic elements of the b12 binding surface that would be regarded as still part of the present invention. Any natural variation of the predicted segments may be substituted for the residue identified at a particular position with respect to the HXB2 sequence. Table 2 represents the results of BLAST analysis of the segment of HXB2 HIV-1 gp120 against all the other known HIV sequences. Then each residue of the cluster A peptides was analyzed for variations seen in the top 50 closest peptide sequences found. As to be expected, there is just a limited degree of variation. The same BLAST analysis can be conducted taking the consensus sequence of each of the clades. HXB2 is a representative of clade B.

Table 2 below shows that variability may be found within the consensus of each clade. Residue-variation at each position was obtained by multiple sequence alignment with HXB2 (50 homologs were analyzed):

TABLE 2

| Residue in HXB2 | Natural Variations |
|---|---|
| ILE 360 | A, F, H, K, N, R, S, T, V, Y |
| PHE 361 | L |
| LYS 362 | A, D, I, N, Q, R, T, V |
| PHE 391 | I, L |
| ASN 392 | S, T |
| SER 393 | D, G, N, W, Y |
| THR 394 | A, I, L, N, V |
| TRP 395 | E, H, I, N |
| PHE 396 | D, L, N, Q, R, T, Y |
| ASP 457 | N |

TABLE 2-continued

| Residue in HXB2 | Natural Variations |
|---|---|
| GLY 458 | A, E, S, T, V, W, Y |
| GLY 459 | D, I, N, P, Q, R, T, V |
| ASN 460 | A, I, K, Q, S, T, V |
| SER 461 | D, E, G, N |
| ASN 462 | D, E, G, I, K, Q, S, T, V |
| ASN 463 | D, Q, S, T |
| GLU 464 | D, G, K, N, Q, R, S, T |
| SER 465 | E, H, I, N, T |
| GLU 466 | L |
| ILE 467 | N, T, V |
| PHE 468 | G, I, L, N, S |

Using a similar analysis, known variations that diverge from target sequences of each clade can be determined, all of which are considered to be encompassed by the present invention. Thus for example, the tryptophan residue in position 395 in HXB2 has diverged to tyrosine in clade C, glycine in clade F1 and cysteine in clade O1. These three variations are not included in the BLAST analysis described in Table 2, illustrating therefore that such a BLAST analysis for each clade consensus sequence would certainly expand the range of anticipated variation permissible for each amino acid position claimed as part of this invention.

Any of the residues that appear at a given position in any clade may be substituted for the residue in the HXB2 isolate which has been specified when making pharmaceutical compositions comprising the basic elements or when making the molecules that are mimetic of the binding surface. Preferably, the highly conserved residues are maintained.

Once a molecule is identified that is mimetic of the binding surface, it is produced for ultimate use. If the mimetic is a peptide, it may either be synthesized or produced recombinantly in methods that are well known to those of ordinary skill in the art. Where necessary, disulfide bonds may be caused to be formed in such peptides by means that are well known to those of ordinary skill in the art.

The present invention may be used to produce a vaccine in any situation in which a desirable neutralizing antibody is known for any given pathogen and the antigen that is recognized by that antibody has a known three-dimensional structure. Oftentimes, it is undesirable to use the pathogen itself or even the antigen as a vaccine in view of problems of toxicity or lack of immunogenicity or immunodominance of unrelated epitopes. By means of the present invention, the binding surface of the antigen may be identified and a molecule mimetic thereof produced which, when used as an immunogen, will in effect raise antibodies similar to the desirable neutralizing antibody used as the starting material. A useful non-toxic vaccine thereby becomes available for active immunization.

If the mAb used coincides with a binding site on the proteinaceous material for another ligand, such as, for example, the CD4 or CCR5 binding site on gp120, then the predicted and reconstituted epitope might itself bind the ligand, such as CD4 or CCR5 in the above example. Thus, such a reconstituted epitope could be used directly as an antiviral therapeutic. It would not involve undue experimentation to test any such reconstituted epitope for this utility and then formulate appropriate therapeutic compositions, including appropriate pharmaceutically acceptable excipients. Furthermore, it is well within the skill of those of ordinary skill in the art to empirically determine appropriate dosages and means of administration for such an antiviral therapeutic.

If the mAb that one starts with binds specifically to the active site of an enzyme, then it would be expected that the reconstituted epitope could act as a catalytic peptide and could be used for catalysis in a bioreactor scenario. Again, it is within the skill of the art to determine whether any given reconstituted epitope in such a situation does act as a catalytic peptide by routine experimentation. If it does have such a property, those of skill in the art could use the catalytic peptide for catalysis in a bioreactor scenario without engaging in undue experimentation.

The approach of the present invention is based on the assumption that the collection of random peptides that bind specifically to the antibody being studied must reflect in some manner the paratopes of that antibody. Furthermore, as the antibody was produced to correspond to the native antigen, the native epitope should in some fashion correlate with this same collection of affinity-selected peptides. In the following examples, the reference mAbs, 17b and 13b5, were useful for the formulation of the algorithm providing known positive controls. Of course, other control antibodies that have been solved in a co-crystal could also have been selected. Once the system appeared to be working, the prediction of the CG10 and b12 epitopes was undertaken.

The following examples provide four lines of evidence that give credence to the approach of the present invention.

The epitope predicted for CG10 entails segments that overlap with the 17b epitope. Both these mAbs have been studied extensively and have been found to be distinct yet do compete for gp120 binding, suggesting that there should be common shared elements in their corresponding epitopes (Sullivan et al, 1998).

The epitopes do not coincide completely and one can conclude this also by comparing phage sequences found by screening the library with both antibodies (FIGS. 2A and 7A). The phages that were selected by screening the 17b mAb do not interact with the CG10 mAb and vice versa (data not shown). Moreover, as previously discussed, the sequences of CDR-loops of both antibodies are also different, particularly the CDR3-loops of the heavy chains (FIG. 6). It is obvious, therefore, that these antibodies should not necessarily have the same contact residues even when they form overlapping interfaces with gp120.

Five of the predicted amino acids of the CG10 epitope have been shown by mutational analyses performed by others to be critical for mAb binding to gp120 (Rizzuto et al, 1998).

The construction of the reconstituted epitope that binds CG10 and competes against CD4/gp120 complex.

This last criterion is especially important as it illustrates that not only is the procedure of the present invention able to identify a limited cluster of residues that appear to be critical for mAb binding, it is possible to "string them together" in a meaningful way. The concept of reconstituting discontinuous epitopes is not new. There have been previous successful studies where segments of a protein have been produced as contiguous elements in a single synthetic peptide structure (Ottl et al, 1999; Villen et al, 2001). Functional reproduction of the discontinuous antigenic site D of foot-and-mouth disease virus (FMDV) has been achieved by means of synthetic peptide constructions that integrate into a single molecule each of the three protein loops that define the antigenic site. Antisera to the peptide were moderately neutralizing of FMDV in cell culture and partially protective of guinea pigs against challenge with the virus. These results demonstrate functional mimicry of the discontinuous epitope D by the peptide, which is therefore an obvious candidate for a peptide-based vaccine against FMDV (Villen et al, 2001).

The G12 construct produced in Example 3 reconfirms, therefore, two major aspects of the present invention, the predictability of epitopes by combining the phage analyses with the algorithm of the present invention and the feasibility of reconstituting discontinuous epitopes.

The reconstructed epitope molecules corresponding to the predicted antigenic determinants can be used as a synthetic vaccine that will generate antibodies that have the same specificity as the original antibody used in the analysis. The reconstituted CG10 epitope that has been produced based on the predictions of the present invention can be used as a synthetic vaccine.

The present invention will be better understood by consideration of the following non-limiting examples.

Example 1 mAb 17b

The concept of the present invention will first be demonstrated using a control model system. The ternary complex of the core of HIV-1 gp120 with a truncated version of its receptor, soluble CD4 (sCD4) and a Fab fragment of the mAb 17b has been crystallized and solved to 2.5-2.2 Å resolution (Kwong et al, 2000; Rizzuto et al, 2000; Wyatt et al, 1998; Kwong et al 1998; Rizzuto et al, 1998). As a result, the 17b epitope is known to be comprised of four discontinuous beta-strands. Thus, this information allows the known mAb 17b epitope to be used as a control model system.

MAb 17b was used to repeatedly screen combinatorial phage display peptide libraries until a collection of peptides was obtained. As is illustrated in FIG. 2A, eleven random peptides were isolated through the comprehensive screening of three combinatorial phage display peptide libraries. Each library represented $1\text{-}5\times10^9$ recombinant random 12 mer peptides flanked by constant cysteine residues so to constrain a looped structure at the $NH_2$ terminus of the major coat protein, pVIII, of the filamentous bacteriophage fd (one of the selected peptides happens to contain only 8 residues). No obvious homology exists between the peptides and gp120.

In order to derive the epitope of mAb 17b from the 11 peptides described above, the novel computational algorithm discussed above was utilized (FIG. 1 is a general scheme of the final algorithm).

Identification of Over-Represented Amino Acid Pairs:

Step I in the computer algorithm is to calculate the number of occurrences of specific amino acid pairs present in the affinity-selected phage-displayed peptides, and identify those pairs that are substantially over-represented as compared to the random frequencies of pairs statistically anticipated.

Calculation of random frequencies of amino acid pairs was performed as discussed above. As contacts between the mAb and the antigen are through functional moieties of the R-groups, conserved residues were consolidated into the six functional subgroups of amino acids, as discussed above, and given the following single letter codes:

R,K=B
E,D=J
S,T=O
L,V,I=U
Q,N=X
W,F=Z.

The anticipated frequencies ($n_r$) of the amino acid pairs for totally random peptides were then calculated and are given in FIG. 3A.

Two types of pairs must be considered: completely random pairs, in which both partners of a pair are random and "semi-random" pairs in which only one partner is random, whereas the other is constant (as is in the case for the first and last pair of each peptide containing the constant flanking cysteine residues).

Figure 3B:
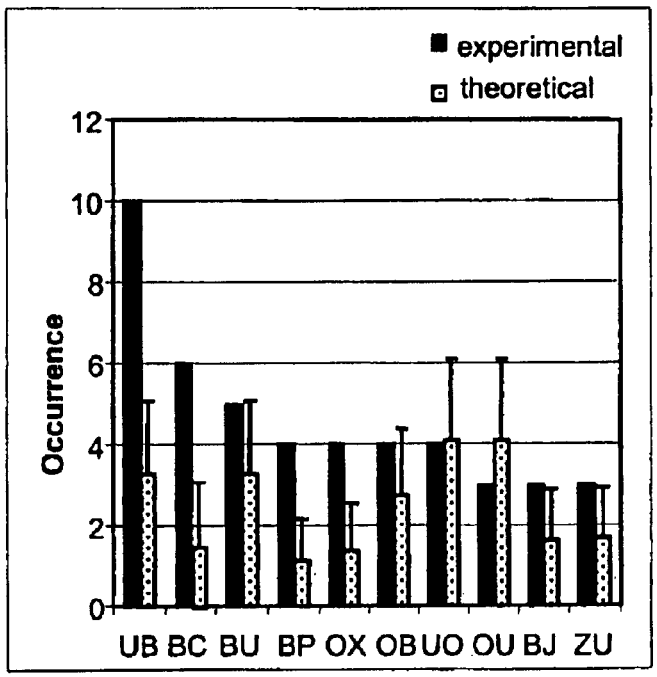
FIG. 3B is a bar graph showing the identification of statistically significant pairs (SSP's): comparison of theoretical ($f_r$) (stippled columns) and experimentally observed (solid columns) occurrences of 17b amino acid pairs. Error bars present $\sqrt{f_r}$ as a measure of random error. The theoretical occurrences are based on randomness and were calculated by multiplying the theoretical frequency of a pair ($n_r$) with the total number of pairs in a specific set of peptides (A) [$f_r=n_r \cdot A$]. The theoretical probabilities of the BC and CB pairs were calculated taking into account the "semi-random" nature of these pairs.

The peptide sequences were converted into their amino acid pair equivalents (FIG. 2B). The 11 peptides comprise a total of 141 amino acid pairs (119 are completely random and 22 pairs are "semi-random"), representing 84 different pairs of the 169 possible pairs (considering the 13 amino acid categories, see FIG. 3A). The number of occurrences for each amino acid pair of the 11 affinity selected peptides was scored and a list of amino acid pairs ranked according to their occurrences is given in FIG. 2C (this corresponds to "Product I" in FIG. 1). Then, the expected theoretical number of specific amino acid pairs ($f_r=n_r \cdot A$, where A is number of amino acid pairs in a set of peptides) was calculated for 17b selected peptides based on the randomness. FIG. 3B compares the theoretical occurrences ($f_r$) to the experimental occurrences in the isolated 17b selected peptides. For example, ten UB pairs exist in the eleven 17b-peptides which is at least twice as many as would be expected randomly. Thus, for the 7 most prevalent pairs in the 17b-peptides four of them (UB, BC, BP and OX) are statistically more abundant than randomness would predict and thus represent the set of the most statistically significant pairs (SSP, see algorithm FIG. 1). Note the propensity for positively charged residues (B=K,R) which is not surprising in view of the acidic nature of the CDR3 loop of the heavy chain of 17b (Kwong et al, 1998); see also FIG. 6).

The next step is to identify the most prevalent pairs of amino acids described above, within the three dimensional structure of gp120. Then, based on these clustered pairs, candidate epitopes are predicted. The present novel computer algorithm is designed to accomplish these two tasks.

Identification of Epitope-Relevant Amino Acid Pairs

In essence, pairs of amino acids in the antigen are sought that are functionally represented by the tandem residues in the 12 mer peptides displayed on the phages. The dimensions of what is a pair have been defined hereinabove. Using these definitions, each epitope-relevant amino acid pair in the proteinaceous material can readily be identified from the database of distances between each possible pair of amino acids in the protein.

Figure 4B:
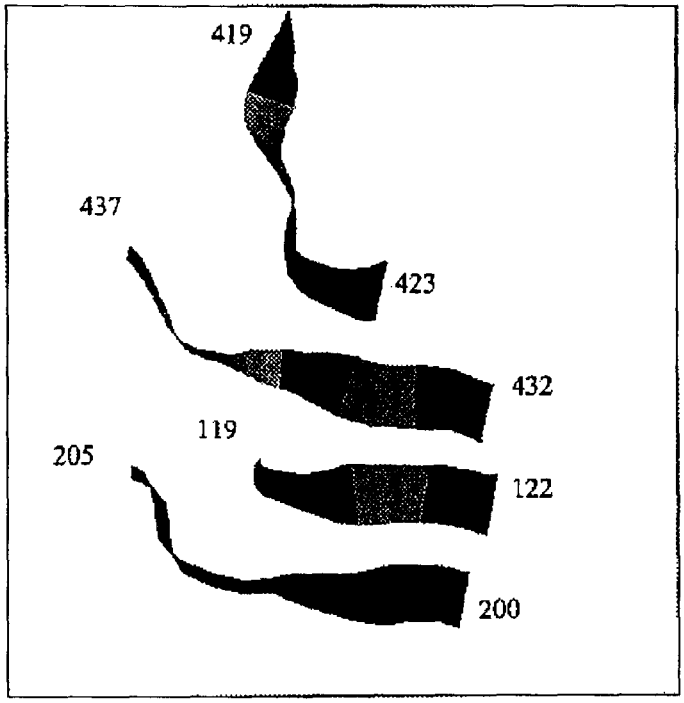
FIGS. 4B and 4D show RasMol representations of the 17b epitope.
Figure 4C:
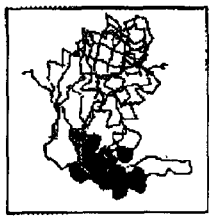
FIG. 4C shows a model of gp120 backbone+genuine 17b epitope residues.

Prediction of Candidate Epitopes:

Once the relevant amino acid pairs are identified on the surface of the antigen, clustered-pairs can then be defined. A cluster of pairs is determined when a member of one pair can be connected to a member of a second pair, which in turn is connected to a third and so forth. Thus, for example, in FIG. 4A a list of the SSP clusters relevant to the 17b-selected peptides is provided (Product III, FIG. 1). Seven clusters could be defined. The largest is Cluster A. Note that the UB pair L111, K117 (first pair in Cluster A) is connected to the BC pair K117, C205 as K117 is common to both. The OX T202, Q203 pair is included as T202 in tandem to I201. BU was included despite the fact that, while abundant, it is statistically within the error set for randomness. It was included to test whether the inclusion would improve the prediction. The difference without BU (data not shown) is only slight. The same binding elements are predicted except that amino acids 419 and 208 were not included in the absence of BU. Thus, it should be understood that the definition of statistical error given above is not the only definition of statistical significance that can be used and that making such judgment calls is within the skill of the art.

An alternative embodiment of the present invention is to consider forward and reverse pairs, e.g., BU and UB, as being equivalent when conducting the SSP analysis. Thus, the number of each would be added together, and the $n_r$ for each would be added when determining which pairs are relevant.

Thus, one can define the boundaries of a given cluster through rules of connectivity. The cluster of highest relevance is considered to be that cluster that includes the maximal number of pairs, types of pairs and total amino acids associated via connectivity. Cluster A is a particularly attractive candidate-epitope as it comprises 27 pairs of 5 different pair types (UB, BP, BC, BU and OX) encompassing a total of 24 different amino acid residues.

Figure 4D:
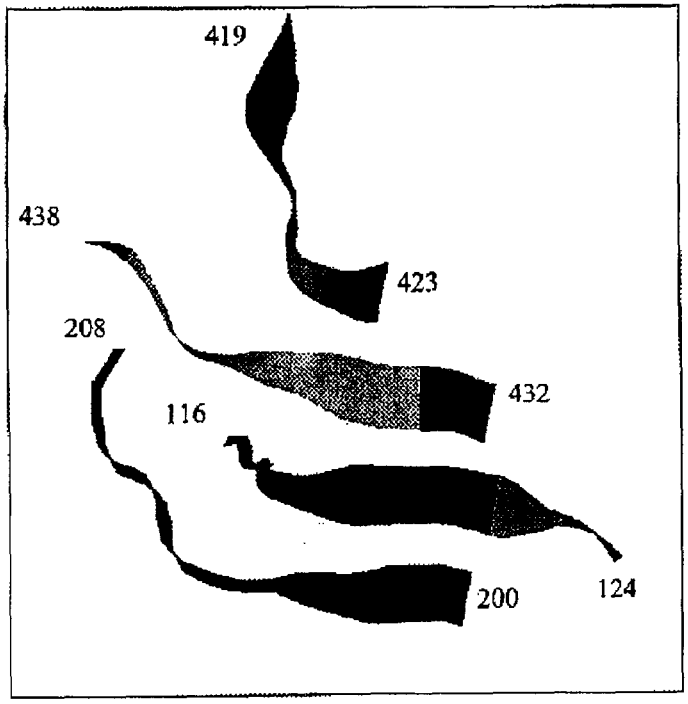
Figure 4E:
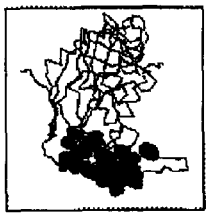
FIG. 4E shows the predicted "cluster A", displayed as space fill residues.

FIG. 4E depicts Cluster A in the context of the gp120 crystalline structure. The predicted epitope comprises four segments of the gp120 molecule that together create an anti-parallel beta-sheet surface (FIG. 4D). As can be seen, this predicted epitope (Product IV, FIG. 1) corresponds very well with the actual contact residues of the 17b epitope as determined from the co-crystal (FIG. 4B; Kwong et al, 1998). Thus, it appears that the computer algorithm correctly identified the elements of the bona fide 17b epitope based on the affinity-selected phage-displayed peptides.

Example 2 mAb 13b5

Figure 5D:
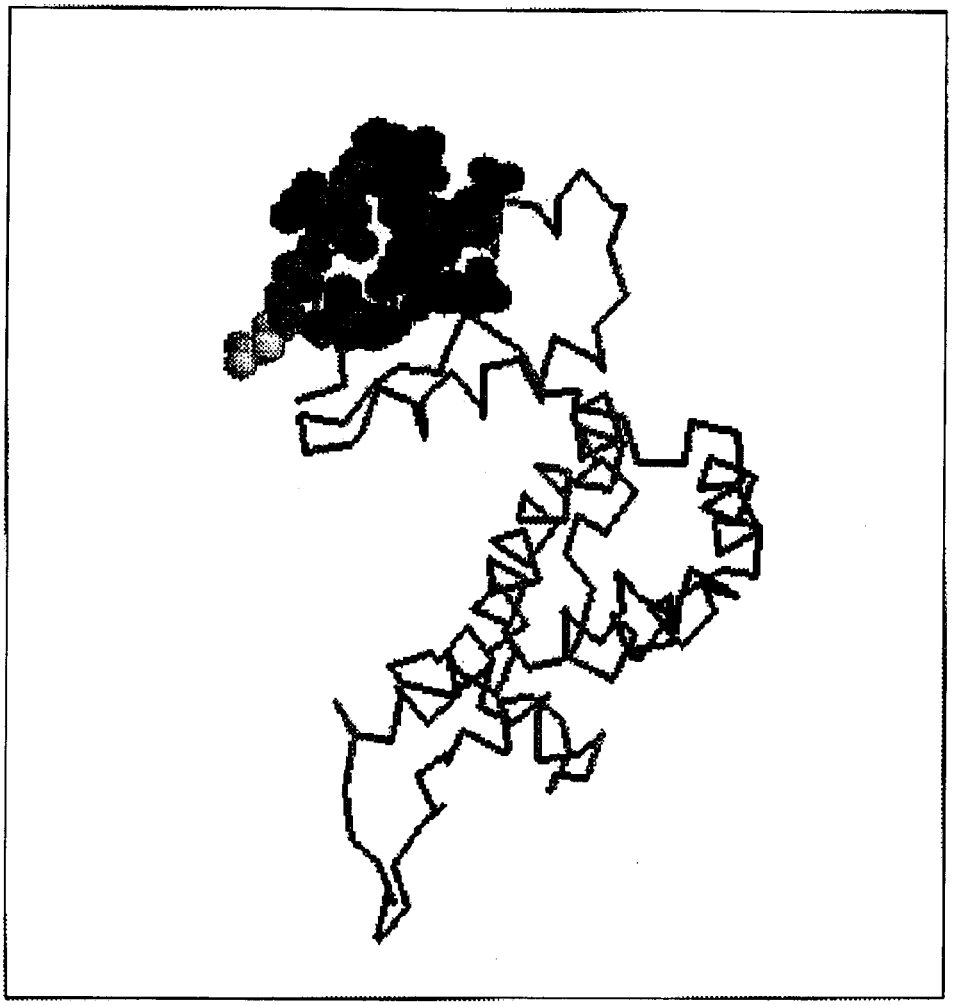
FIG. 5D is the RasMol representation of the 13b5 epitope. A model of the p24 backbone and the epitope is displayed as space fill residues. The spheres of lightest color are only predicted residues; the spheres of intermediate darkness are only experimental residues; and the black spheres are coinciding residues.

The algorithm was further tested using a second control mAb. The mAb 13b5 binds HIV-1 p24 antigen (Monaco-Malbet et al, 2000). The epitope of 13b5 has been defined in the 13b5/p24 co-crystal (3 Å resolution) (Berthet-Colominas, 1999). Therefore, 13b5 was used to screen the 12 mer constrained-loop peptide library described herein. Initially, 10 peptides were isolated and used for the computational analysis. A number of poorly-defined clusters were predicted including the region of the genuine epitope. In order to improve the statistics and sharpen the cluster analysis, additional libraries were screened until a total of 16 different 13b5-specific peptides were isolated (FIGS. 5A and 5B). These were then used for analysis and the algorithm predicted 4 clusters (FIG. 5C). The largest and most comprehensive corresponded remarkably well to the genuine epitope illustrating the predictive power of the method (FIG. 5D).

Example 3 mAb CG10

In view of the above success in epitope prediction, the phage/algorithm analysis of the present invention was then applied to a mAb where its corresponding epitope is unknown. For this, the mAb CG10, which binds to a highly conformation dependent epitope peculiar to the CD4/gp120 complex (Gershoni et al, 1993), was used. In view of the fact that 17b and CG10 compete for CD4/gp120 complex binding, it was expected that the CG10 epitope should overlap to some degree with the 17b epitope (Sullivan et al, 1998). On the other hand, comparing the molecular structure of the CDR loops of both mAbs shows marked differences between the two (FIG. 6). The CDR3 of the 17b heavy chain is extremely acidic (containing 5 E or D residues out of 12 amino acids). In contrast to this, the CDR3 of the CG10 heavy chain is rather hydrophobic. One should expect, therefore, very distinct random peptides for each mAb.

CG10 was used to screen the phage-display peptide libraries produced in the laboratory of the present inventors until a total of 28 phages were affinity isolated (FIG. 7A). These were then translated into their corresponding amino acid pair equivalents (FIG. 7B) and the list of amino acid pairs ranked according to the number of occurrences (Product I, FIG. 1) is given in FIG. 7C.

Figure 7D:
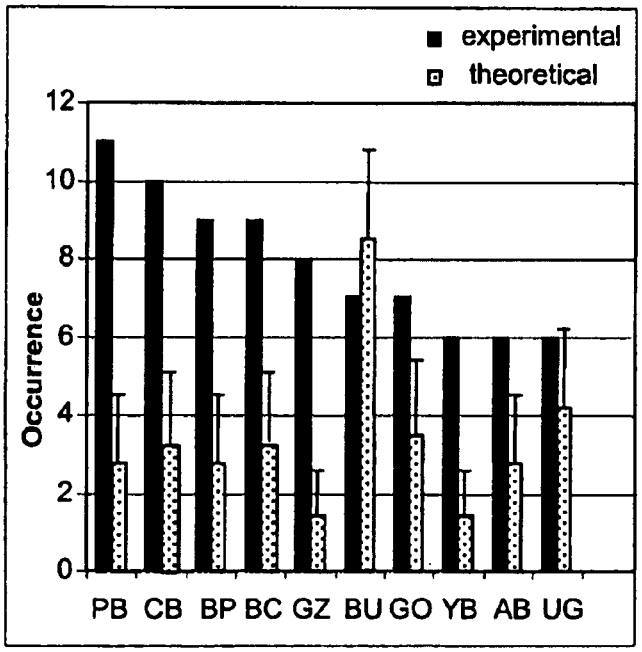
FIG. 7D is a bar graph showing the identification of SSP's, comprising the theoretical and experimental occurrences of CG10 amino acid pairs.

Comparison of the usage of the amino acid pairs found in the CG10-specific peptides versus the expected random usage is given in FIG. 7D. As to be expected, in comparison with the same analysis of 17b, there are marked differences. The most prevalent 17b pair, UB, is very rare in the CG10-specific peptides. PB, the most abundant CG10 pair, is relatively rare for 17b (2 incidences). Clearly, the general profile of amino acid pairs used to produce CG10 binding peptides is markedly different from that found for 17b. These differences in composition explain the fact that whereas 17b and CG10 compete for gp120, none of the 17b selected phages are recognized by CG10 and vice versa.

Figure 9A:
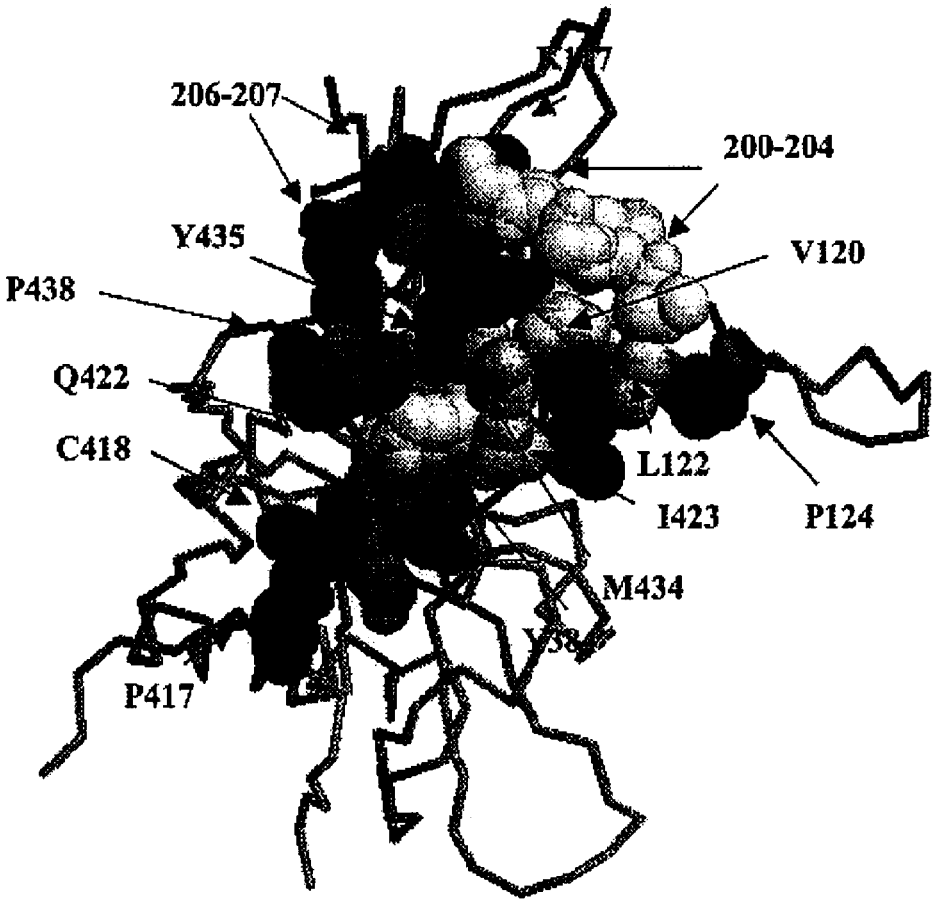
FIGS. 9A-9C are RasMol depictions of the CG10 epitope.
Figure 9B:
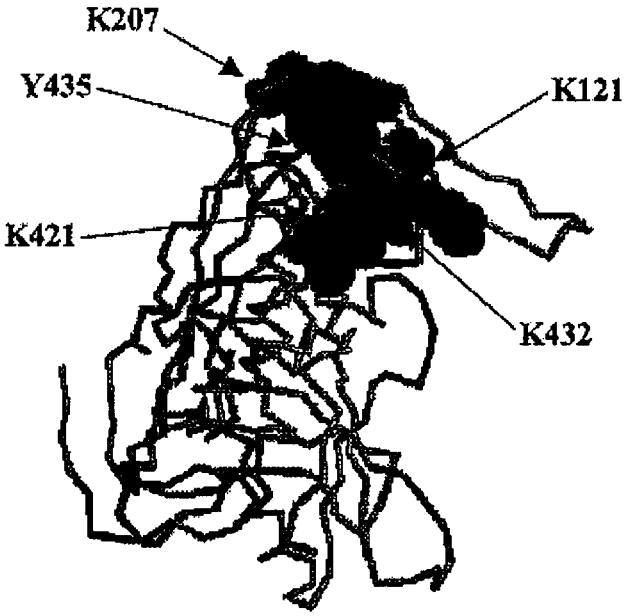
Figure 9C:
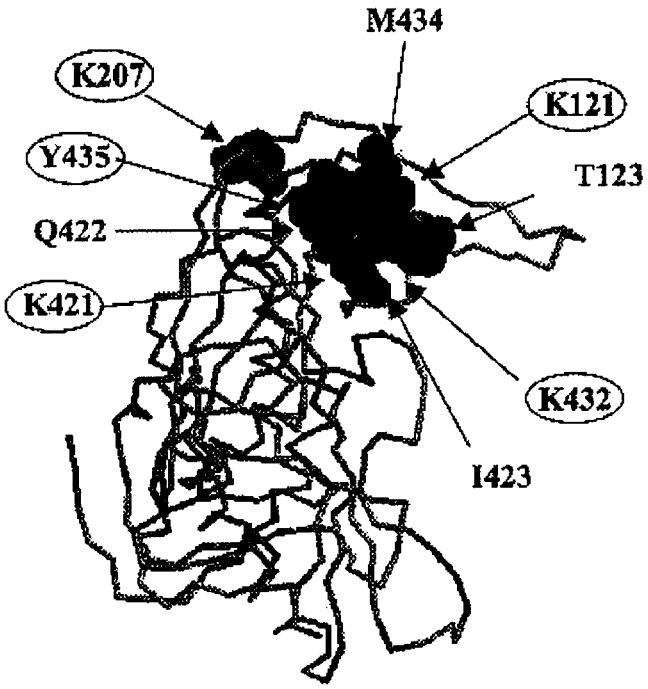

The search for clusters on the gp120 surface (Step II, FIG. 1) for CG10 produced seven clusters of which only Cluster A seemed extensive and likely as an epitope candidate (FIG. 8). FIG. 9A shows the position of this cluster within the crystalline model of gp120. Indeed, as expected, the predicted CG10 epitope does overlap with the 17b epitope yet contains elements unique and distinct as well. The question is how confident can one be with this prediction? Evidence for the validity of the prediction can be found in the comparison of the predicted epitope and the mutation analysis performed by Rizzuto et al (1998) for CG10 binding. As is illustrated in FIG. 9 (compare FIG. 9B with FIG. 9C) five predicted residues correspond with five mutations previously shown to affect CG10 binding to the CD4/gp120 complex.

Figure 10D:
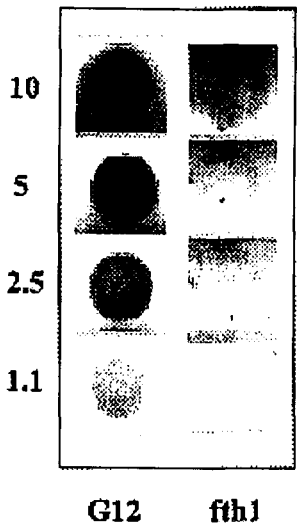
FIG. 10D is a dot blot analysis of CG10 binding to phage G12.
Figure 10E:
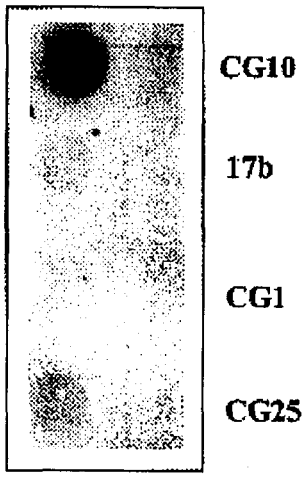
FIG. 10E shows the G12 phage binding by CG10 vs CG1, 17b and CG25 mAbs.
Figure 10F:
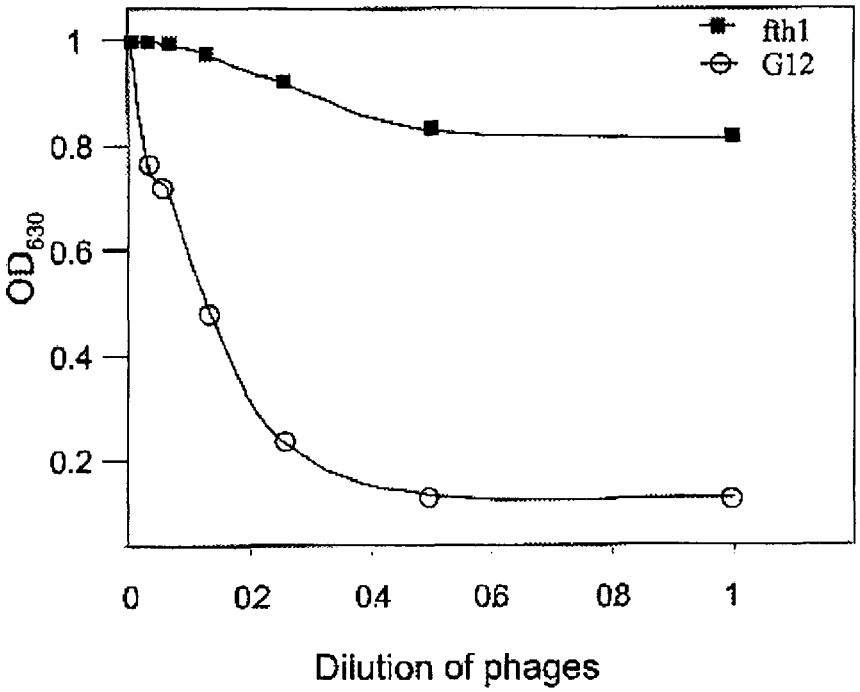
FIG. 10F is a graph showing the competition between G12 phage and the CD4/gp120 complex for CG10 mAb binding.

Reconstitution of the CG10 Epitope:

The information as to the mapping of the CG10 epitope can best be used by physically creating a molecule that effectively reconstitutes the CG10 epitope based on the prediction. For this, four short peptide segments of gp120 that were predicted to comprise the CG10 epitope, were used to generate an epitope mimetic (see FIGS. 10A-10C). To fill the gap between amino acids K207 and K421 a fifth segment comprising amino acid residues F381-E382 was introduced. The logic was based on the fact that in the original gp120 molecule these amino acids form non-covalent contacts with K421 and Y435 stabilizing the conformation (Kwong et al, 1998). As is shown in FIGS. 10A-10C, the five segments were either connected directly to one another or via two tri-peptide linkers (GPG) designed to impose a turn in the structure. Since the epitope consists of anti-parallel beta-strands, fragments #3, #4 and #5 (FIG. 10C) within the reconstituted sequence were introduced in the opposite direction as compared to the original antigen sequence to satisfy spatial requirements. Thus, the 25 amino acid sequence derived from gp120 (FIG. 10C) was taken (including the two predicted cysteine residues, cys119 and cys205), which create, therefore, a constrained loop that was introduced into the N-terminus of the pVIII protein of the fd bacteriophage. Phages were isolated and tested for their specific binding of CG10. As can be seen in FIG. 10D, the phage expressing the reconstituted epitope (designated G12) readily bound CG10 in contrast to the lack of binding for the control fth1 phage. The specificity of the binding was shown in FIG. 10E where only CG10 bound G12 as compared to three other mAbs that bind other epitopes. Note that 17b did not bind G12, once again demonstrating the distinct nature of these two overlapping epitopes. Finally, G12 was found to efficiently compete for CG10-binding against the CD4/gp120 complex (FIG. 10F). In view of these results, it was concluded that not only was the presentation able to predict the CG10 epitope based on phage analysis and application of the herein described computer algorithm, but also reconstitute the epitope based on this prediction.

Example 4 mAb b12

Figure 12:
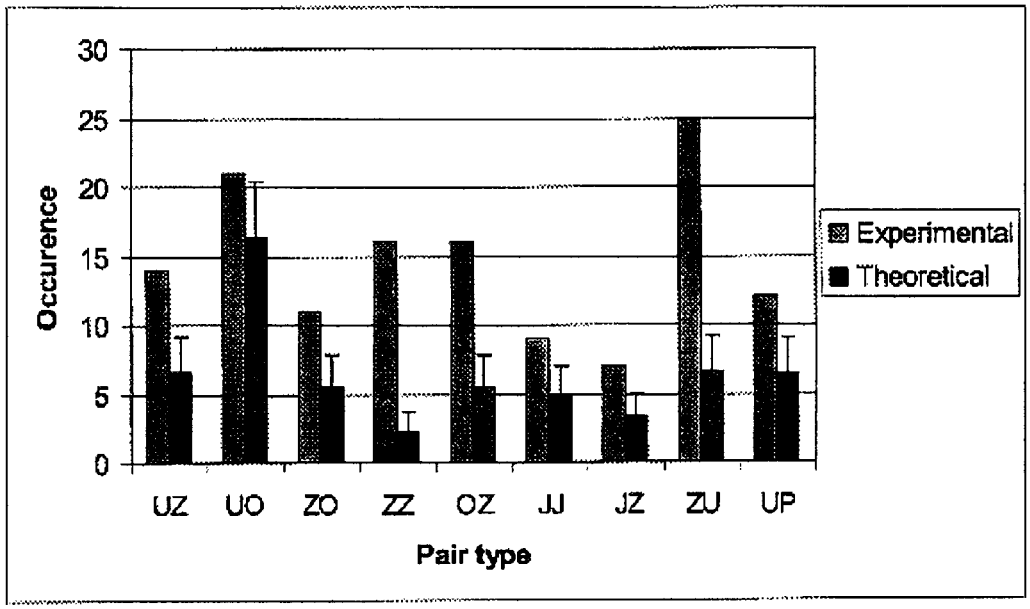
FIG. 12 is a graph showing the identification of statistically significant pairs: comparisons of theoretical (dark columns) and experimental (light columns) occurrence of b12 amino acid pairs.
Figure 13A:
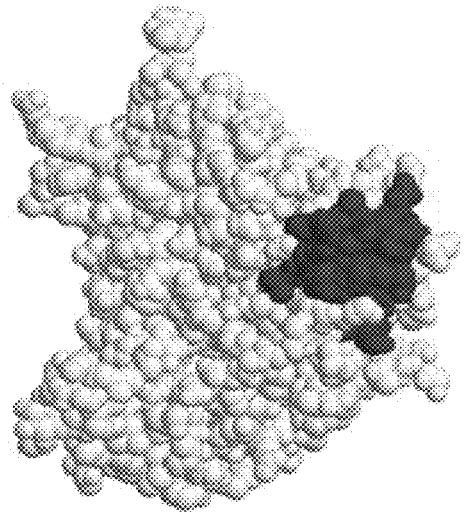
FIGS. 13A-E show Clusters A, B, C (front), C (rear), and D, respectively, of b12 epitope pairs and 13C show clusters of b12 epitope pairs. The predicted residues are shown in color.
Figure 13B:
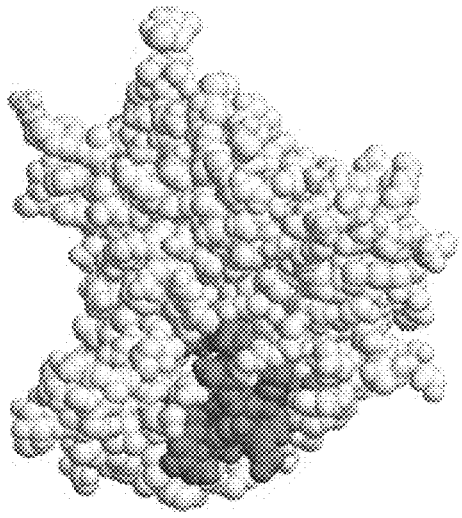
Figure 13C:
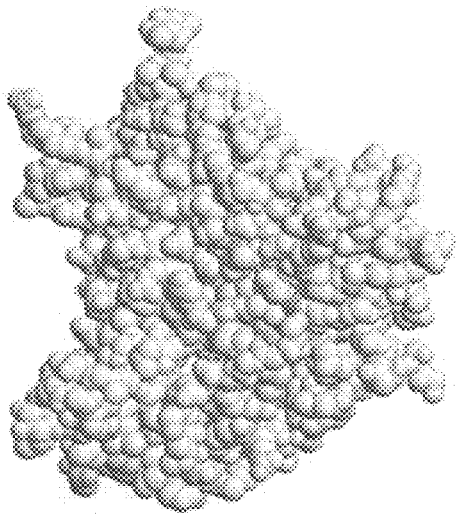
Figure 13D:
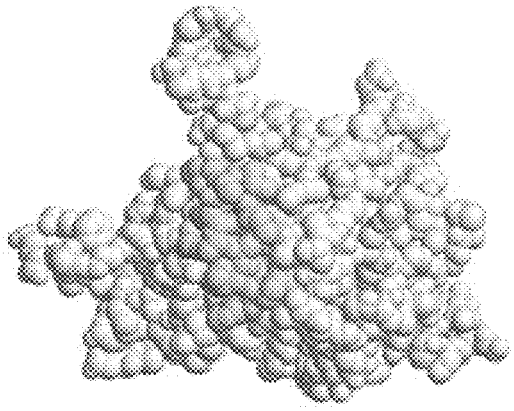
Figure 13E:
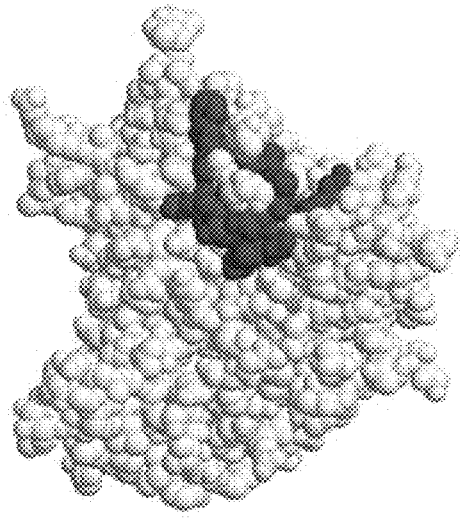

One of the most important mAbs that interacts with the CD4 binding site on HIV-1 surface glycoprotein gp120 is mAb b12, which is known to neutralize many primary and TCLA viruses very efficiently (Burton et al, 1994). This antibody has been extensively studied, and the first step of the present invention has already been reported in the prior art in studies by others. Thus, Zwick et al (2001a) and Boots et al (1997) report the screening of peptide libraries using the b12 mAb, as well as the sequences of peptides found to bind thereto. These reported peptides can be used in the algorithm of the present invention so as to predict the binding elements of the binding surface of gp120, which is bound by mAb b12 without the necessity of using the antibody itself. Thus, 32 peptides from Boots et al (1997) and two peptides from Zwick et al (2001a) (FIG. 11A), were translated into their corresponding amino acid pair equivalents (FIG. 11B), and the list of amino acid pairs ranked according to the number of occurrences is given in FIG. 11C. Comparison of the usage of the amino acid pairs with the statistical frequencies, as shown in FIG. 12, allows the identification of those pairs that are particularly relevant.

The algorithm was then applied to identify the pairs on the surface of gp120 and four clusters were identified as potential epitope elements (FIGS. 13A-E).

These analyses predict four major clusters: Cluster A: T358-F361, T391-F396, T455-F468; Cluster B: V254-T257, D368-F376, F382-N386 and C418-I424 Cluster C: S115-V120, I201-F210 and Cluster D W96, T232-P238, V271-T283, F353. The residues correspond to the numeration of gp120 of HIV-1 HXB2 isolate (SEQ ID NO:1).

These analyses predict that three strands of gp120 comprise major elements of the b12 epitope: residues 360-362, 391-396 and 464-468. In addition, conducting the analysis on the two peptides isolated by Zwick et al (2001a) (the last two peptides in FIG. 11A) residue Asp457 is predicted to be part of the epitope (the significance of Asp457 is lost when the two Zwick et al (2001a) peptides are taken together with those of Boots et al (1997)). The residues correspond to the numeration of gp120 of HIV-1 HXB2 isolate (SEQ ID NO:1).

Cluster C (S115-V120, I201-F210) is tandem to the C1 helix of gp120 (residues 105-112). This helix is bound by the monoclonal antibody GV1A8 (Stern 1997). In view of the fact that mAb GV1A8 does not interfere with b12 binding to gp120 in a competitive ELISA test, Cluster C is considered to be a weak candidate for the b12 epitope. Cluster D is located away from the CD4 binding site and as such would not explain CD4 inhibition of b12 binding and thus is not considered to be a strong b12 epitope candidate.

Both Clusters A and B are therefore the most likely candidates for the b12 epitope. The algorithm does not sufficiently distinguish between them and thus both Clusters are taken as epitope candidates. In order to distinguish between the two so to identify a possible more likely candidate the following two analyses were conducted.

Mutation analyses of selected residues on gp120 have been published by numerous investigators ([Pantophlet, 2003, Roben, 1994, Saphire, 2001). There are 8 mutations included in the Cluster B prediction that affect b12 binding 7 of which (S256, D368, E370, V372, T373, Y384 and N386) almost knocked out b12 binding completely (≥85%). There are 6 mutations contained within Cluster A, 3 of which reduce b12 binding by more than 80% (D457, S461, E464), 2 that reduce b12 binding by 37% and 50% (I467 and S465, respectively)

and one that increases binding by 500% (T455). In view of these data it would appear that Cluster B is more sensitive to mutations than is Cluster A and thus might be a stronger candidate for the b12 epitope.

The second analysis is based on the fact that the b12 antibody is highly cross reactive. Therefore each of the clusters were analyzed by the computer program ConSurf (consurf-.tau.ac.i1/) and the results of these analyses are shown in Table 3. Here a clear distinction between the two Clusters exists and Cluster B is markedly more conserved than is Cluster A.

TABLE 3

| Conseravation Scores (9 Conserved, 1 Non-Conserved) | | | |
|---|---|---|---|
| Cluster B | | Cluster A | |
| Amino acid | Score | Amino acid | Score |
| V254 | 8 | T358 | 1 |
| V255 | 8 | I359 | 9 |
| S256 | 9 | I360 | 1 |
| T257 | 9 | F361 | 7 |
| D368 | 9 | F391 | 8 |
| Q370 | 9 | S393 | 5 |
| I371 | 7 | T394 | 6 |
| V372 | 7 | W395 | 4 |
| T373 | 4 | F396 | 4 |
| H374 | 8 | T455 | 8 |
| S375 | 6 | D457 | 8 |
| F376 | 7 | S461 | 1 |
| C418 | 9 | E464 | 1 |
| I410 | 9 | S645 | 2 |
| I423 | 8 | E466 | 8 |
| I424 | 6 | I467 | 7 |
| | | F468 | 6 |

In summary four Clusters are predicted for the b12 epitope. Clusters C and D are weak candidates whereas Clusters A and B are both good candidates for the b12 epitope. There is some evidence that the strongest candidate is Cluster B however Cluster A should not be excluded.

In order to reconstitute the b12 epitope, one first highlights the predicted segments of the epitope within the three dimensional model of gp120. This should be done for each Cluster. The following are two examples; one for Cluster A, the second for Cluster B. However, one should appreciate that similar and other analyses and constructions should be possible and as such the examples are not restricting. By highlighting the predicted segments of a given cluster, one immediately appreciates the spacial relatedness of each segment and understands the sequential order that must be maintained in order to construct a single linear peptidomimetic of the epitope. Thus, for example, for construction and topographical considerations, residue 362 may be added without substantially changing the likelihood of the peptidomimetic having the desired properties. Similarly, residues 455 and 456 may or may not be present. In order to include predicted residue 457 in the construct, a single continuous element ranging from 457 through 468 is shown, although it may be preferable to start the continuous element at residue 455. Thus, starting with residue 391, one strings the elements together proceeding to residue 396, followed by a short bridging linker (TPGS (residues 9-12 of SEQ ID NO:104) that imposes a turn) followed by the sequence 358 through 362 (or, perhaps more preferably, 361, not shown). A second TPGS (residues 18-21 of SEQ ID NO:104) linker allows a turn in the construct to be followed by the reversed orientation segment 468 through 457 (or, perhaps more preferably, 455, not shown). The distance between the ends of this construct is predicted to be 14-15 Å. In order to bridge this gap, one can introduce residues derived from the 110-118 segment, which includes most of one of the peptide elements predicted for cluster C. Thus, the first seven residues (SLWDQSL, residues 110-116 of SEQ ID NO:1) were introduced to bridge the gap. This permits at least a portion of another predicted peptide element to be included in the peptidomimetic. Then, flanking cysteine residues are included to produce a constrained looped peptide that contains the sequential as well as spacial orientation of the residues predicted for the b12 epitope. The resultant peptide is shown in FIG. 14C (SEQ ID NO:104).

An additional variation of this kind of construct is illustrated in FIG. 15 in which the same elements are incorporated into a double cysteine looped construct. This illustrates that there may be more than one way to connect the basic elements in a manner so as to substantially maintain the relative spatial orientation of the amino acids in the basic elements. Those of ordinary skill in the art, following the instructions in the present disclosure, and being aware of prior art methods of doing so (see, for example Villen et al, 2001), can readily perform such a step without engaging in undue experimentation.

In contrast to the preceding example in which the elements of an epitope, or part thereof, are strung together (with or without bridging linkers) into a linear peptidomimetic, the epitope elements may also be incorporated into existing scaffolds. The concept is based on the fundamental premise that if an epitope element is of a given secondary conformation in the original antigen, it will continue to assume the same structure even when it replaces a different sequence with a similar structure in the context of a foreign polypeptide scaffold. In other words, the gp120 derived peptides, when grafted into the scaffold, will assume their native conformation there.

Figure 16A:
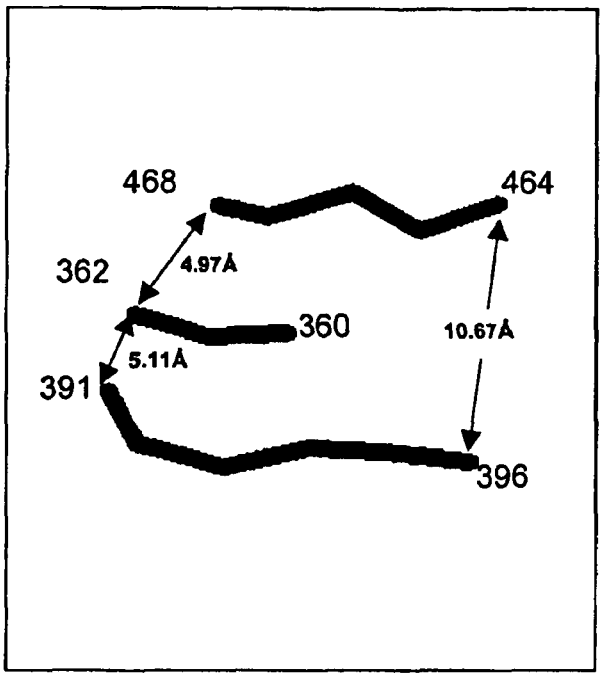
FIG. 16A shows the structure of the three binding elements of FIG. 13E, including the distance between the terminal alpha-carbons thereof.

The b12 epitope elements, for example, form a beta-sheet comprised of three beta strands. FIG. 16A. The native orientation of these strands can be defined by measuring the distances between the ends of the strands as is illustrated.

Once one knows the structure one is interested in (FIG. 16A) one can survey the database of solved crystalline structures of proteins and search for compatible scaffolds. In the following case, beta-sheet structures are to be analyzed. It is well known in the art that members of the super gene family of immunoglobulins contain considerable beta-sheet structures. Thus, for example, one can examine the solved structure of CD4, a member of this gene family.

Figure 16B:
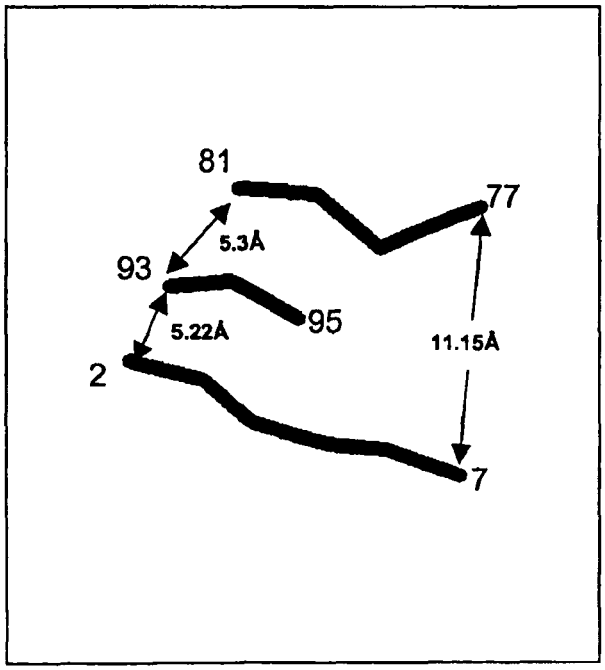
FIGS. 16B and 16C show the structure of the peptide elements that are part of the CD4 protein (SEQ ID NO:106) and the $V_H$ domains of the murine IgG1 protein (SEQ ID NO:107), respectively.

The model of the CD4 backbone can be visualized with any of the graphic programs such as RasMol, PDB viewer or Protein Explorer. One then can selectively highlight segments of CD4 that assume beta-strand secondary structure (a standard command in any of these programs). Seeking areas that form beta-sheets of the same general dimensions and shape of that of the b12 epitope, it becomes apparent that the three strands of CD4: residues 77-81, 93-95 and 2-7 (of SEQ ID NO:106), are excellent candidates for strand exchanges. Thus, a method for the expression of the b12 epitope is to incorporate the gp120 strands into the corresponding locations of the identified CD4 beta-sheet as is illustrated in FIG. 16B. This will result in a hybrid protein with the sequence of SEQ ID NO:134.

Figure 16C:
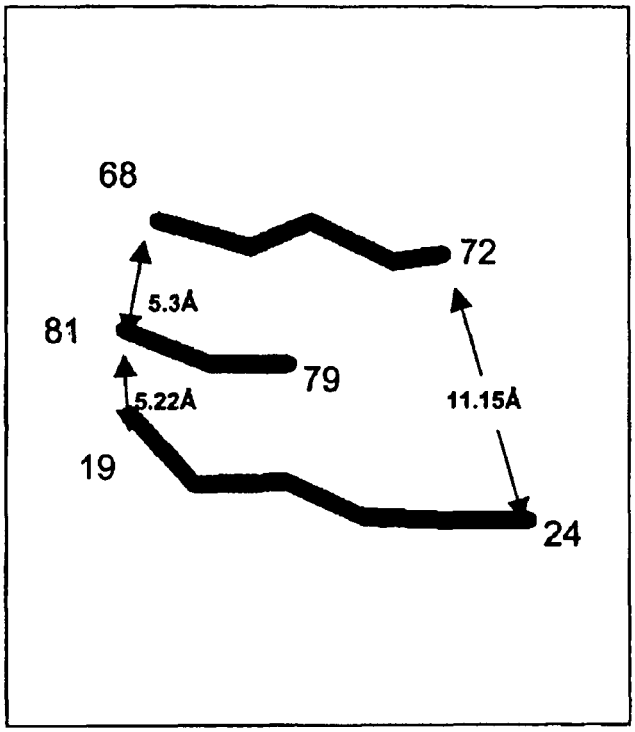

A second example of such a grafted construct is shown in FIG. 16C in which the gp120 segments replace compatible segments of the framework component of the $V_H$ domain of murine IgG1 (SEQ ID NO:107). This will result in a hybrid protein with the sequence of SEQ ID NO:135. A similar analysis can be conducted for the strands disclosed herein for Cluster B.

Figure 17A:
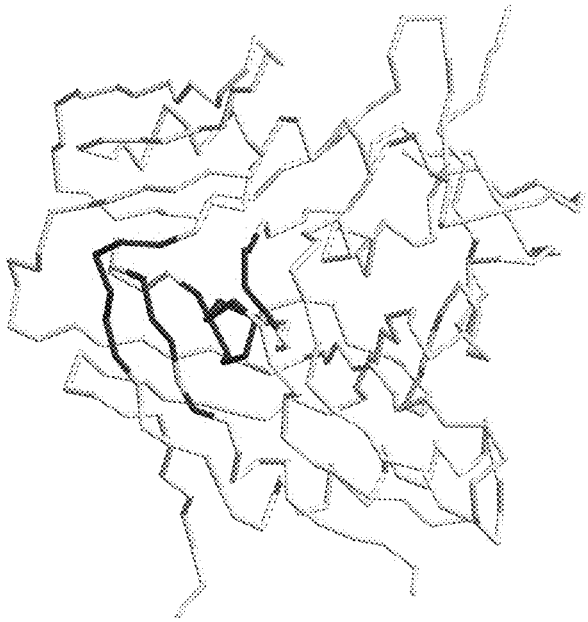
FIG. 17A shows the strands of Cluster B highlighted within the backbone representation of gp120.
Figure 17B:
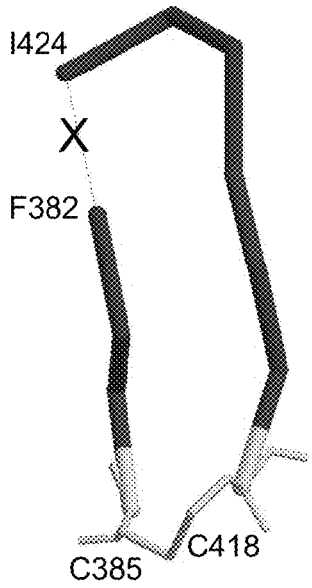
FIG. 17B shows the relative orientation of the beta strands 418-424 and 382-385 that are both parts of Cluster B. An alternative containing the 382-385 segment is shown in FIG. 17C.
Figure 17C:
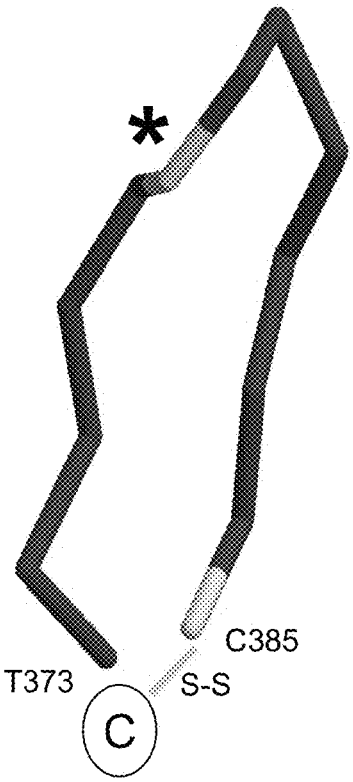
FIG. 17D shows a construct in which 373 to 385 is one continuous loop of gp120, containing an additional cysteine residue (indicated by the circled C).
FIG. 17E shows a construct in which the sequence 370-375 forms a loop with a gap between 370 and 375 of 5.4 angstroms.
FIG. 17F shows the structure of the 13B5 heavy chain residues 14 to 119, in which the two strands of the framework of the beta barrel of the heavy chain that otherwise support the CDR3 loop are highlighted in blue.
FIG. 17G illustrates the fact that the two strands of FIG. 17F can support the 370-375 loop of FIG. 17E.
Figure 17D:
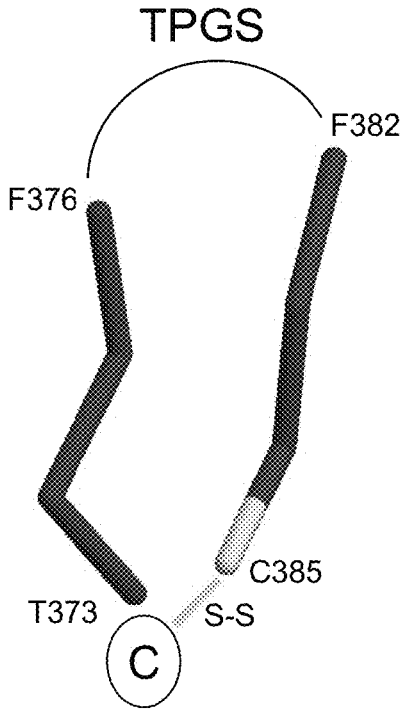

As is illustrated in FIG. 17A the strands of Cluster B are highlighted within the backbone representation of gp120. This epitope consists of four strands and here we illustrate the possibility of expressing segments of the epitope separately. The rationale is that effectively produced segments can be used independently or together as a mixture for immunization. Antibodies binding to these immunogens would cross-react with gp120 and these in turn would be able to prevent HIV infection of target cells. FIG. 17B shows the relative orientation of the beta strands 418-424 and 382-385 that are both parts of Cluster B. One can appreciate that the gap between residues 424 and 382 can be closed by introducing one or two amino acid residues. Thus, a total of no more than 40 different constructs would have to be screened against b12 to select for that construct that best represents the native conformation of these two segments. An alternative containing the 382-385 segment is shown in FIG. 17C. Here, the 382-385 strand is paired with another component of Cluster B, namely segment 373-376. If one were to introduce a second cysteine residue just following threonine 373, a disulfide bond could be formed between the new cysteine and, by single group rotation, the sulfhydryl of cysteine 385. The gap between residues 376 and 382 could be closed by a linker such as described previously, e.g., the short tetra-peptide TPGS. An alternative could be to simply include residues of gp120 that naturally bridge between 376 and 382. As is shown in FIGS. 17D, 373 to 385 is one continuous loop of gp120. This loop contains an additional cysteine residue (indicated by the circled C). In order to avoid mismatching of cysteines in the formation of disulfide bonds, one could point mutate the extra cysteine into serine.

Figure 17E:
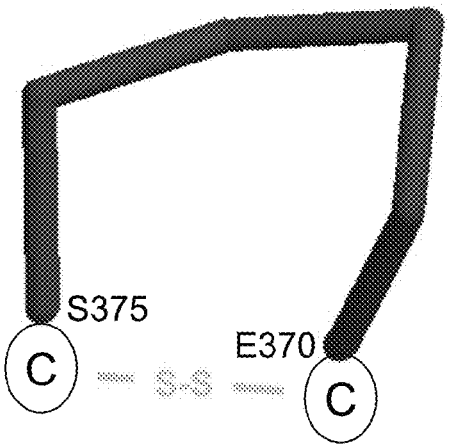
Figure 17F:
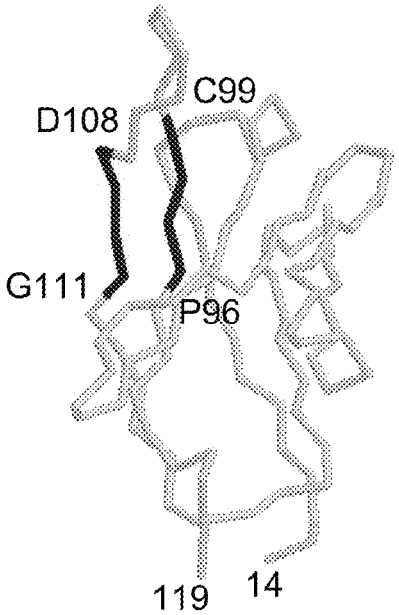
Figure 17G:
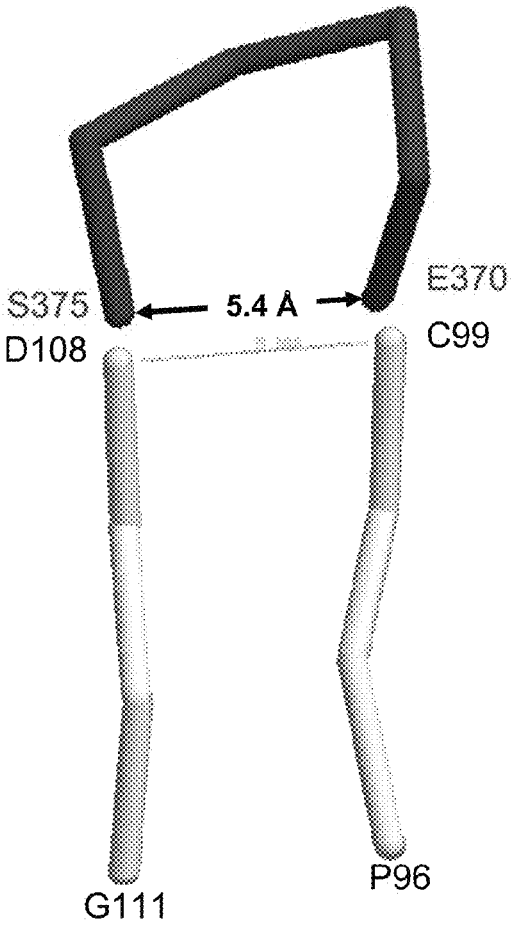

Yet a third segment of Cluster B can be used to form an immunogen. The sequence 370-375 forms a loop with a gap between 370 and 375 of 5.4 angstrom (FIG. 17E). One can introduce flanking cysteines just preceding and following residues 370 and 375 respectively and express such a cysteine constrained loop. An alternative to this would be to support the loop on a protein scaffold as described previously for Cluster A. FIG. 17F shows the structure of the 13B5 heavy chain residues 14 to 119. The two strands of the framework of the beta barrel of the heavy chain that otherwise support the CDR3 loop are highlighted in blue. These two strands can support the 370-375 loop as is illustrated in FIG. 17G.

Example 5

Materials and Methods

DNA Preparations

Single-stranded DNA of filamentous phages was isolated using the QIAprep Spin M13 Kit® (QIAGEN GmbH, Germany).

Monoclonal Antibodies

CG10, CG1 and CG9 mAbs used in this study were produced at Tel Aviv University (Gershoni et al, 1993). Human mAb 17b was produced at Tulane University Medical Center (Thali et al, 1993). The mAb 13b5 is a product of bioMérieux, France (Monaco-Malbet et al, 2000).

Library Construction and Biopanning

Three 12-mer cysteine-constrained peptide libraries were constructed: one in ftac88 and the other two in fth1 (Enshell-Seijffers et al, 2001). Protein G (Sigma Chemical Co, St. Louis, Mo.) was used to coat the bottom of 35-mm tissue culture 6-well plates overnight at 4° C. (50 μg of protein G in 0.7 ml Tris buffered saline (TBS)). After discarding the excess solution, the dish was blocked with TBS containing 0.25% (w/v) gelatin (TBSG) for 2 hours at room temperature. Next, the dish was rinsed rapidly five times with TBS and incubated with a total volume of 0.7 ml containing 10-50 μg of mAb and rocked gently at room temperature for 4 hours. After washing with TBS, biopanning was accomplished by adding $10^{11}$ phages from the library to the dish in 0.7 ml TBSG and incubated at 4° C. overnight. Unbound phages were rinsed away and the dish was washed extensively ten times with TBS. Bound phages were eluted with 400 μl of elution buffer (0.1 M HCl adjusted to pH 2.2 with glycine, 1 mg/ml BSA) for 10 minutes at room temperature with gentle agitation. The eluate was transferred into a 1.5 ml microfuge tube and neutralized with 75 μl of neutralizing buffer (1M Tris-HCl pH 9.1). For more details see Enshell-Siejffers et al, 2002).

Immunoscreening

DH5alphaF+ bacteria were infected with the affinity selected phages and plated on LB plates containing 20 μg/ml tetracycline and grown at 37° C. overnight. Single colonies were picked to inoculate 200 μl Terrific Broth in U-bottom 96 well plates. After overnight culture the plates were centrifuged at 3000 rpm for 30 minutes at room temperature. 125 μl of the supernatant from each well were transferred to a flat-bottom, 96-well plate already containing 50 μl/well of PEG/NaCl solution. The flat-bottom plates were incubated at 4° C. for 2 hours and centrifuged. The precipitated phages were re-suspended in a total of 100 μl TBS and applied via a vacuum manifold to nitrocellulose filters. After blocking with 5% milk in TBS for 1 hour, the membranes were washed briefly with TBS and incubated overnight with the selected mAb (1-2 μg/ml) in TBS/5% milk at 4° C. with gentle rocking. After washing, the membranes were incubated with goat-anti mouse IgG/HRP conjugates diluted 1:5000 in TBS/5% milk for 1 hour at room temperature (Enshell-Siejffers et al, 2002). The positive signals were detected by ECL (Amersham) immunodetection.

Sequencing

For sequencing the inserts of the phages selected from library, single-stranded DNA was isolated from phage-particles and used as a template for sequencing using the primer 5'-GGTCAGACGATTGGCCTTG-3'(SEQ ID NO:136) (Enshell-Siejffers et al, 2002).

Reconstitution of CG10 Epitope

For the construction of the reconstituted CG10-epitope, two complementary oligonucleotides were used:

```
                                        (SEQ ID NO: 137)
5'-GTGTGTAAAATTAACTGCACCAGGAGTAGGAAAAGCAATGTATGGCC
CTGGGATTCAAAAATTCGAAAAGCCATGTGCTG-3'
and

                                        (SEQ ID NO: 138)
5'-CAGCACATGGCTTTTCGAATTTTTGAATCCCAGGGCCATACATTGCT
TTTCCTACTCCTGGTGCAGTTAATTTTACACAC-3'
```

which were designed to create an insert containing 3'-overhang ends compatible with the Sfi I sites of the fth1 vector and reconstruct the reading frame of phage pVIII protein. The oligonucleotides were heated at 86° C. 10 minutes and allowed to slowly cool to 35° C. and then were ligated with fth1 vector cut with Sfi I to produce clone G12.

Analysis of the Reconstituted CG10 Epitope

100 μl of phages G12 or fth1 were applied onto nitrocellulose membrane filters, blocked with 5% milk and incubated with mAbs: CG10 (1-10 μg/ml), CG1, 17b and CG25 mAbs (5 μg/ml) overnight at 4° C. Then the membranes were washed and probed with anti-mouse IgG conjugated with HRP. ECL reaction was used for detection.

ELISA

CG10 (1 μg/ml) was pre-incubated overnight at 4° C. with a series of double diluted phages (G12 or fth1, $10^{11}$ was the starting amount) and then applied onto ELISA plates coated with CD4/gp120 complex (375 ng) and incubated 1 hour at room temperature and then probed with anti-mouse alkaline phosphatase conjugate.

Structure Analyses

Definition of the 17b contact residues and surface accessible residues were performed according to Sobolev et al (1999).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

REFERENCES

Berthet-Colominas et al, "Head-to-tail dimers and interdomain flexibility revealed by the crystal structure of HIV-1 capsid protein (p24) com-plexed with a monoclonal antibody Fab", EMBO J", 18:1124-1136 (1999)

Boots et al, "Anti-human immunodeficiency virus type 1 human monoclonal antibodies that bind discontinuous epitopes in the viral glycoproteins can identify mimotopes from recombinant phage peptide display libraries", AIDS Res Hum Retroviruses 13(18):1549-1559 (1997)

Burton et al, "Efficient neutralization of primary isolates of HIV 1 by a recombinant human monoclonal antibody", Science 266:1024-1027 (1994)

Burton et al, "Why do we not have an HIV vaccine and how can we make one?" Nat Med 4:495-498 (1998)

Chakrabarti et al, "Dissecting protein-protein recognition sites", Proteins 47:334-343 (2002)

Conley et al, "Neutralization of divergent human immunodeficiency virus type 1 variants and primary isolates by IAM-41-2F5, an anti-gp41 human monoclonal antibody", Proc Natl Acad Sci USA 91:3348-52 (1994)

Ellis R W, "Technologies for the design, discovery, formulation and administration of vaccines", Vaccine 19:2681-2687 (2001)

Enshell-Seijffers et al, "The rational design of a 'type 88' genetically stable peptide display vector in the filamentous bacteriophage fd", Nucleic Acids Res 29:E50-0 (2001)

Enshell-Siejffers et al, "Phage-display selection and analysis of Ab-binding epitopes", in Current Protocols in Immunology (Coligan et al, Eds.), John Wiley & Sons, New York (2002)

Enshell-Siejffers et al, "The mapping and reconstitution of a conformational discontinuous B-cell epitope of HIV-1", J. Mol. Biol. 334, 87-101 (2003)

Felici et al, "Mimicking of discontinuous epitopes by phage-displayed peptides, II", Selection of clones recognized by a protective monoclonal antibody against the Bordetella pertussis toxin from phage peptide libraries", Gene 128: 21-27(1993)

Folgori et al, "A general strategy to identify mimotopes of pathological antigens using only random peptide libraries and human sera", Embo J, 13:2236-2243 (1994)

Gauduin et al, "Passive immunization with a human monoclonal antibody protects hu-PBL-SCID mice against challenge by primary isolates of HIV-1", Nat Med 3:1389-1393 (1997)

Gershoni et al, "HIV binding to its receptor creates specific epitopes for the CD4/gp120 complex", Faseb J 7:1185-1187 (1993)

Gershoni et al, "Determination and Control of Bimolecular Interactions", WO 98/20169, published May 14, 1998

Glaser et al, "Residue frequencies and pairing preferences at protein-protein interfaces", Proteins 43:89-102 (2001)

Hansson et al, "Design and production of recombinant subunit vaccines", Biotechnol Appl Biochem 32, 95-107 (2000)

Ho et al, "Construction of recombinant targeting immunogens incorporating an HIV-1 neutralizing epitope into sites of differing conformational constraint", Vaccine 20:1169-1180 (2002)

Hofmann et al, "On the theoretical prediction of protein antigenic determinants from amino acid sequences", Biomed Biochim Acta 46:855-866 (1987)

Hoffmann-Lehmann et al, "Molecular evolution of human immunodeficiency virus env in humans and monkeys: similar patterns occur during natural disease progression or rapid virus passage", J Virol 76:5278-284 (2002)

Hopp T P, "Protein antigen conformation: folding patterns and predictive algorithms; selection of antigenic and immunogenic peptides", Ann Sclavo Collana Monogr 1:47-60 (1984)

Hopp T P, "Retrospective: 12 years of antigenic determinant predictions, and more", Pept Res 6:183-190(1993)

Jones et al, "Analysis of protein-protein interaction sites using surface patches", J Mol Biol 272:121-132 (1997a)

Jones et al, "Prediction of protein-protein interaction sites using patch analysis", J Mol Biol 272:133-143 (1997b)

Kabat E A. Structural concepts in immunology and immunochemistry (Ebert et al Eds), Holt, Rinehart and Winston, Inc., New York, (1968)

Kwong et al, "Structure of an HIV gp120 envelope glycoprotein in complex with the CD4 receptor and a neutralizing human antibody", Nature 393:648-59 (1998)

Kwong et al, "Structures of HIV-1 gp120 envelope glycoproteins from laboratory-adapted and primary isolates", Structure Fold Des 8:1329-1339 (2000)

Lo Conte et al, "The atomic structure of protein-protein recognition sites", J Mol Biol 285:2177-2198 (1999)

Mascola et al, "Protection of macaques against pathogenic simian/human immunodeficiency virus 89.6PD by passive transfer of neu-tralizing antibodies", J Virol 73:4009-4018 (1999)

Monaco-Malbet et al, "Mutual Conformational Adaptations in Antigen and Antibody upon Complex Formation between an Fab and HIV-1 Capsid Protein p24", Structure 8:1069-1077 (2000)

Montefiori et al, "HIV vaccines, Magic of the occult?", Science 283, 336-337 (1999)

Moore et al, "Genetic subtypes, humoral immunity, and human immunodeficiency virus type 1 vaccine development", J Virol 75:5721-9 (2001)

Muster et al, "A conserved neutralizing epitope on gp41 of human immunodeficiency virus type 1", J Virol 67:6642-6647 (1993)

Ottl et al, "Heterotrimeric collagen peptides containing functional epitopes. Synthesis of single-stranded collagen type I peptides related to the collagenase cleavage site", J Pept Sci 5:103-110 (1999)

Parker et al, "New hydrophilicity scale derived from high-performance liquid chromatography peptide retention data: correlation of predicted surface residues with antigenicity and X-ray-derived accessible sites", Biochemistry 25:5425-5432 (1986)

Pantophlet et al, "Hyperglycosylated mutants of human immunodeficiency virus (HIV) type 1 monomeric gp120 as novel antigens for HIV vaccine design", J Virol 77(10): 5889-5901 (2003)

Pauletti et al, "Application of a modified computer algorithm in determining potential antigenic determinants associated with the AIDS virus glycoprotein", Anal Biochem 151: 540-546 (1985)

Rizzuto et al, "A conserved HIV gp120 glycoprotein structure involved in chemokine receptor binding", Science 280: 1949-1953 (1998)

Rizzuto et al, "Fine definition of a conserved CCR5-binding region on the human immunodeficiency virus type 1 glycoprotein 120", AIDS Res Hum Retroviruses 16:741-749 (2000)

Sobolev et al, "Automated analysis of interatomic contacts in proteins", Bioinformatics 15:327-332 (1999)

Sullivan et al, "CD4-Induced conformational changes in the human immunodeficiency virus type 1 gp120 glycoprotein: consequences for virus entry and neutralization", J Virol 72:4694-4703 (1998)

Thali et al. "Characterization of conserved human immunodeficiency virus type 1 gp120 neutralization epitopes exposed upon gp120-CD4 binding", J Virol 67:3978-3988 (1993)

Trkola et al, "Human monoclonal antibody 2G12 defines a distinctive neutralization epitope on the gp120 glycoprotein of human immunodeficiency virus type 1", J Virol 70:1100-1108 (1996)

Tsodikov et al, "Novel computer program for fast exact calculation of accessible and molecular surface areas and average surface curvature", J. Comput. Chem 23, 600-609 (2002)

Van Regenmortel et al, "Predicting antigenic determinants in proteins: looking for unidimensional solutions to a three-dimensional problem?", Pept Res 7"224-228 (1994)

Van Regenmortel M H V, "Mapping Epitope Structure and Activity: From One-Dimensional Prediction to Four-Dimensional Description of Antigenic Specificity", Methods 9:465-72 (1996)

Van Regenmortel M H V, "Molecular dissection of protein antigens and prediction of epitopes" in Synthetic Peptides as Antigens (van der Vliet, Ed.), Elsevier Science, Amsterdam (1999)

Van Regenmortal, M H V, "Antigenicity and immunogenicity of synthetic peptides", Biologicals, 29(3-4):209-13, September-December (2001)

Villen et al, "Synthetic peptides as functional mimics of a viral discontinuous antigenic site", Biologicals 29:265-269 (2001)

Wang et al, "Emergence of autologous neutralization-resistant variants from preexisting human immunodeficiency virus (HIV) quasi species during virus rebound in HIV type 1-infected patients undergoing highly active antiretroviral therapy", J Infect Dis 185:608-617 (2002)

Welling et al, "Choice of peptide and peptide length for the generation of antibodies reactive with the intact protein", FEBS Lett 182:81-84 (1985)

Wyatt et al, "The antigenic structure of the HIV gp120 envelope glycoprotein", Nature 393:705-711 (1998)

Xu et al, "Hydrogen bonds and salt bridges across protein-protein interfaces", Protein Eng 10:999-1012 (1997)

Zwick et al, "Identification and characterization of a peptide that specifically binds the human, broadly neutralizing anti-human immunodeficiency virus type 1 antibody b12". J Virol 75(14):6692-6699 (2001a)

Zwick et al, "Broadly neutralizing antibodies targeted to the membrane-proximal external region of human immunodeficiency virus type 1 glycoprotein gp41", J Virol 75(22): 10892-10905 (2001b)

SEQUENCE LISTING

```
<160> NUMBER OF SEQ ID NOS: 138

<210> SEQ ID NO 1
<211> LENGTH: 856
<212> TYPE: PRT
<213> ORGANISM: HIV-1

<400> SEQUENCE: 1

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
```

```
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480
```

```
Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
        515                 520                 525

Thr Met Gly Ala Ala Ser Met Thr Leu Thr Val Gln Ala Arg Gln Leu
    530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
        595                 600                 605

Pro Trp Asn Ala Ser Trp Ser Asn Lys Ser Leu Glu Gln Ile Trp Asn
    610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
        675                 680                 685

Val Gly Gly Leu Val Gly Leu Arg Ile Val Phe Ala Val Leu Ser Ile
    690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
    850                 855


<210> SEQ ID NO 2
<211> LENGTH: 12
<212> TYPE: PRT
<213> ORGANISM: Artificial
<220> FEATURE:
<223> OTHER INFORMATION: synthetic
```

<400> SEQUENCE: 2

Cys Ser Gly Leu Arg Asn Glu Thr Phe Leu Arg Cys
1 5 10

<210> SEQ ID NO 3
<211> LENGTH: 14
<212> TYPE: PRT
<213> ORGANISM: Artificial
<220> FEATURE:
<223> OTHER INFORMATION: synthetic

<400> SEQUENCE: 3

Cys Glu Phe Phe Gln Gln His Met Leu Arg Val Pro Arg Cys
1 5 10

<210> SEQ ID NO 4
<211> LENGTH: 14
<212> TYPE: PRT
<213> ORGANISM: Artificial
<220> FEATURE:
<223> OTHER INFORMATION: synthetic

<400> SEQUENCE: 4

Cys Asn Met Lys Leu Lys Leu Arg Glu Met Thr Gln Arg Cys
1 5 10

<210> SEQ ID NO 5
<211> LENGTH: 14
<212> TYPE: PRT
<213> ORGANISM: Artificial
<220> FEATURE:
<223> OTHER INFORMATION: synthetic

<400> SEQUENCE: 5

Cys Met Thr Arg Pro Thr Ser Leu Thr Gln Leu Thr Gly Cys
1 5 10

<210> SEQ ID NO 6
<211> LENGTH: 14
<212> TYPE: PRT
<213> ORGANISM: Artificial
<220> FEATURE:
<223> OTHER INFORMATION: synthetic

<400> SEQUENCE: 6

Cys Leu His Ile Arg Val Asn Glu Thr Ala Tyr Arg Val Cys
1 5 10

<210> SEQ ID NO 7
<211> LENGTH: 14
<212> TYPE: PRT
<213> ORGANISM: Artificial
<220> FEATURE:
<223> OTHER INFORMATION: synthetic

<400> SEQUENCE: 7

Cys Asp Phe Leu Arg Glu His Gly Met Lys Asn Pro Arg Cys
1 5 10

<210> SEQ ID NO 8
<211> LENGTH: 14
<212> TYPE: PRT
<213> ORGANISM: Artificial
<220> FEATURE:
<223> OTHER INFORMATION: synthetic

<400> SEQUENCE: 8

Cys Arg Ser Arg Pro Thr Asn Met Thr Thr Leu Arg Asp Cys
1 5 10

<210> SEQ ID NO 9
<211> LENGTH: 14
<212> TYPE: PRT
<213> ORGANISM: Artificial
<220> FEATURE:
<223> OTHER INFORMATION: synthetic

<400> SEQUENCE: 9

Cys Ala Ala Tyr Asn Ala Thr Arg Gly Thr Val Ser Ala Cys
1 5 10

<210> SEQ ID NO 10
<211> LENGTH: 14
<212> TYPE: PRT
<213> ORGANISM: Artificial
<220> FEATURE:
<223> OTHER INFORMATION: synthetic

<400> SEQUENCE: 10

Cys Gln Leu Leu His Thr Trp Glu Asp Lys Met Arg Lys Cys
1 5 10

<210> SEQ ID NO 11
<211> LENGTH: 14
<212> TYPE: PRT
<213> ORGANISM: Artificial
<220> FEATURE:
<223> OTHER INFORMATION: synthetic

<400> SEQUENCE: 11

Cys Arg Asn Gly Glu Leu Trp Leu Arg Arg Pro Gly Leu Cys
1 5 10

<210> SEQ ID NO 12
<211> LENGTH: 14
<212> TYPE: PRT
<213> ORGANISM: Artificial
<220> FEATURE:
<223> OTHER INFORMATION: synthetic

<400> SEQUENCE: 12

Cys Met Val Arg Pro Ser Asn Trp Asp Ala Leu Thr Arg Cys
1 5 10

<210> SEQ ID NO 13
<211> LENGTH: 14
<212> TYPE: PRT
<213> ORGANISM: Artificial
<220> FEATURE:
<223> OTHER INFORMATION: synthetic

<400> SEQUENCE: 13

Cys Ala His Phe Pro Pro Arg Ser Gln Met Ile Ala Asp Cys
1 5 10

<210> SEQ ID NO 14
<211> LENGTH: 14
<212> TYPE: PRT
<213> ORGANISM: Artificial
<220> FEATURE:
<223> OTHER INFORMATION: synthetic

<400> SEQUENCE: 14

Cys Ala His Phe Ala Pro Gly Thr Ala Met Tyr Ser Asp Cys
1 5 10

<210> SEQ ID NO 15
<211> LENGTH: 14
<212> TYPE: PRT
<213> ORGANISM: Artificial
<220> FEATURE:
<223> OTHER INFORMATION: synthetic

<400> SEQUENCE: 15

Cys Arg Gln Phe Pro His Ser Ser Ser Met Tyr Thr Asp Cys
1 5 10

<210> SEQ ID NO 16
<211> LENGTH: 14
<212> TYPE: PRT
<213> ORGANISM: Artificial
<220> FEATURE:
<223> OTHER INFORMATION: synthetic

<400> SEQUENCE: 16

Cys Arg Glu Ser Arg Ala Ala Leu Glu Arg Gly Trp Trp Cys
1 5 10

<210> SEQ ID NO 17
<211> LENGTH: 14
<212> TYPE: PRT
<213> ORGANISM: Artificial
<220> FEATURE:
<223> OTHER INFORMATION: synthetic

<400> SEQUENCE: 17

Cys Glu Ala Arg Thr His Asn Glu Ala Arg Arg Arg Arg Cys
1 5 10

<210> SEQ ID NO 18
<211> LENGTH: 14
<212> TYPE: PRT
<213> ORGANISM: Artificial
<220> FEATURE:
<223> OTHER INFORMATION: synthetic

<400> SEQUENCE: 18

Cys Ala Ala Ala Arg Ser Thr Gly Glu Thr Ser Ala His Tyr
1 5 10

<210> SEQ ID NO 19
<211> LENGTH: 14
<212> TYPE: PRT
<213> ORGANISM: Artificial
<220> FEATURE:
<223> OTHER INFORMATION: synthetic

<400> SEQUENCE: 19

Cys Tyr Tyr Arg Met Gly Ala Asn Tyr Thr Val Gly Glu Cys
1 5 10

<210> SEQ ID NO 20
<211> LENGTH: 14
<212> TYPE: PRT
<213> ORGANISM: Artificial
<220> FEATURE:
<223> OTHER INFORMATION: synthetic

<400> SEQUENCE: 20

Cys Ser Val Ser Pro Leu Tyr Ala Tyr Asp Asp Pro Leu Cys
1 5 10

<210> SEQ ID NO 21
<211> LENGTH: 14
<212> TYPE: PRT
<213> ORGANISM: Artificial
<220> FEATURE:
<223> OTHER INFORMATION: synthetic

<400> SEQUENCE: 21

Cys Thr Gln Met His Glu Met Asp Pro Asn Phe Pro Pro Cys
1 5 10

<210> SEQ ID NO 22
<211> LENGTH: 14
<212> TYPE: PRT
<213> ORGANISM: Artificial
<220> FEATURE:
<223> OTHER INFORMATION: synthetic

<400> SEQUENCE: 22

Cys Val Thr Ala Leu Gly Pro Asn Tyr Thr Gly Gln Glu Cys
1 5 10

<210> SEQ ID NO 23
<211> LENGTH: 14
<212> TYPE: PRT
<213> ORGANISM: Artificial
<220> FEATURE:
<223> OTHER INFORMATION: synthetic

<400> SEQUENCE: 23

Cys Tyr Val Gln Gln Pro Trp Trp Val Leu Glu Arg Glu Cys
1 5 10

<210> SEQ ID NO 24
<211> LENGTH: 14
<212> TYPE: PRT
<213> ORGANISM: Artificial
<220> FEATURE:
<223> OTHER INFORMATION: synthetic

<400> SEQUENCE: 24

Cys Ala Asp Val Met Gly Pro Leu Val Thr Ala Ala Glu Cys
1 5 10

<210> SEQ ID NO 25
<211> LENGTH: 14
<212> TYPE: PRT
<213> ORGANISM: Artificial
<220> FEATURE:
<223> OTHER INFORMATION: synthetic

<400> SEQUENCE: 25

Cys Ala Asp Val Met Gly Pro Leu Val Thr Ala Gly Glu Cys
1 5 10

<210> SEQ ID NO 26
<211> LENGTH: 14
<212> TYPE: PRT
<213> ORGANISM: Artificial
<220> FEATURE:
<223> OTHER INFORMATION: synthetic

<400> SEQUENCE: 26

Cys Val Val Phe Leu Asp Val Ser Glu Ala Phe Arg Asp Cys
1 5 10

<210> SEQ ID NO 27
<211> LENGTH: 7

<212> TYPE: PRT
<213> ORGANISM: Artificial
<220> FEATURE:
<223> OTHER INFORMATION: synthetic

<400> SEQUENCE: 27

Val Trp Arg Cys Asn Trp Phe
1 5

<210> SEQ ID NO 28
<211> LENGTH: 7
<212> TYPE: PRT
<213> ORGANISM: Artificial
<220> FEATURE:
<223> OTHER INFORMATION: synthetic

<400> SEQUENCE: 28

Ala Ala Ser Trp Asn Gly Arg
1 5

<210> SEQ ID NO 29
<211> LENGTH: 14
<212> TYPE: PRT
<213> ORGANISM: Artificial
<220> FEATURE:
<223> OTHER INFORMATION: synthetic

<400> SEQUENCE: 29

Gln Ser Val Asp Tyr Asp Gly Asp Ser Tyr Met Asn Trp Tyr
1 5 10

<210> SEQ ID NO 30
<211> LENGTH: 14
<212> TYPE: PRT
<213> ORGANISM: Artificial
<220> FEATURE:
<223> OTHER INFORMATION: synthetic

<400> SEQUENCE: 30

Glu Ser Val Ser Ser Asp Leu Ala Trp Tyr Gln Gln Lys Pro
1 5 10

<210> SEQ ID NO 31
<211> LENGTH: 7
<212> TYPE: PRT
<213> ORGANISM: Artificial
<220> FEATURE:
<223> OTHER INFORMATION: synthetic

<400> SEQUENCE: 31

Ala Ala Ser Asn Leu Glu Ser
1 5

<210> SEQ ID NO 32
<211> LENGTH: 7
<212> TYPE: PRT
<213> ORGANISM: Artificial
<220> FEATURE:
<223> OTHER INFORMATION: synthetic

<400> SEQUENCE: 32

Gly Ala Ser Thr Arg Ala Thr
1 5

<210> SEQ ID NO 33
<211> LENGTH: 5
<212> TYPE: PRT
<213> ORGANISM: Artificial

<220> FEATURE:
<223> OTHER INFORMATION: synthetic

<400> SEQUENCE: 33

Ser His Glu Asp Pro
1 5

<210> SEQ ID NO 34
<211> LENGTH: 6
<212> TYPE: PRT
<213> ORGANISM: Artificial
<220> FEATURE:
<223> OTHER INFORMATION: synthetic

<400> SEQUENCE: 34

Tyr Asn Asn Trp Pro Arg
1 5

<210> SEQ ID NO 35
<211> LENGTH: 11
<212> TYPE: PRT
<213> ORGANISM: Artificial
<220> FEATURE:
<223> OTHER INFORMATION: synthetic

<400> SEQUENCE: 35

Ala Gly Tyr Thr Phe Thr Asp Tyr Trp Ile Gly
1 5 10

<210> SEQ ID NO 36
<211> LENGTH: 11
<212> TYPE: PRT
<213> ORGANISM: Artificial
<220> FEATURE:
<223> OTHER INFORMATION: synthetic

<400> SEQUENCE: 36

Ser Gly Asp Thr Phe Ile Arg Tyr Ser Phe Thr
1 5 10

<210> SEQ ID NO 37
<211> LENGTH: 8
<212> TYPE: PRT
<213> ORGANISM: Artificial
<220> FEATURE:
<223> OTHER INFORMATION: synthetic

<400> SEQUENCE: 37

Pro Gly Gly Asp Tyr Thr Leu Tyr
1 5

<210> SEQ ID NO 38
<211> LENGTH: 8
<212> TYPE: PRT
<213> ORGANISM: Artificial
<220> FEATURE:
<223> OTHER INFORMATION: synthetic

<400> SEQUENCE: 38

Thr Ile Leu Asp Val Ala His His
1 5

<210> SEQ ID NO 39
<211> LENGTH: 12
<212> TYPE: PRT
<213> ORGANISM: Artificial
<220> FEATURE:
<223> OTHER INFORMATION: synthetic

<400> SEQUENCE: 39

Tyr Tyr Gly Tyr Ser Tyr Ala Trp Phe Ala Tyr Trp
1 5 10

<210> SEQ ID NO 40
<211> LENGTH: 12
<212> TYPE: PRT
<213> ORGANISM: Artificial
<220> FEATURE:
<223> OTHER INFORMATION: synthetic

<400> SEQUENCE: 40

Glu Gly Glu Ala Asp Glu Gly Glu Tyr Arg Asn Asn
1 5 10

<210> SEQ ID NO 41
<211> LENGTH: 14
<212> TYPE: PRT
<213> ORGANISM: Artificial
<220> FEATURE:
<223> OTHER INFORMATION: synthetic

<400> SEQUENCE: 41

Cys Ala Lys Glu Gly Asp Leu Asn Lys Tyr Lys Pro Trp Cys
1 5 10

<210> SEQ ID NO 42
<211> LENGTH: 14
<212> TYPE: PRT
<213> ORGANISM: Artificial
<220> FEATURE:
<223> OTHER INFORMATION: synthetic

<400> SEQUENCE: 42

Cys Met Arg Leu Pro Ile Asp Asn Arg Tyr Arg Pro Trp Cys
1 5 10

<210> SEQ ID NO 43
<211> LENGTH: 14
<212> TYPE: PRT
<213> ORGANISM: Artificial
<220> FEATURE:
<223> OTHER INFORMATION: synthetic

<400> SEQUENCE: 43

Cys Arg Tyr Ala Val Thr Val Ala Gln Lys Asn Arg Tyr Cys
1 5 10

<210> SEQ ID NO 44
<211> LENGTH: 14
<212> TYPE: PRT
<213> ORGANISM: Artificial
<220> FEATURE:
<223> OTHER INFORMATION: synthetic

<400> SEQUENCE: 44

Cys Gln Phe Asp Pro Glu Ile Asp Trp Ile Pro Pro Lys Cys
1 5 10

<210> SEQ ID NO 45
<211> LENGTH: 14
<212> TYPE: PRT
<213> ORGANISM: Artificial
<220> FEATURE:
<223> OTHER INFORMATION: synthetic

<400> SEQUENCE: 45

Cys Arg Ser Asp Thr Thr Val Gly Trp Arg Pro Pro Arg Cys
1 5 10

<210> SEQ ID NO 46
<211> LENGTH: 14
<212> TYPE: PRT
<213> ORGANISM: Artificial
<220> FEATURE:
<223> OTHER INFORMATION: synthetic

<400> SEQUENCE: 46

Cys Val Trp Glu Thr Gly Ser Arg Trp Arg Met Pro Lys Cys
1 5 10

<210> SEQ ID NO 47
<211> LENGTH: 14
<212> TYPE: PRT
<213> ORGANISM: Artificial
<220> FEATURE:
<223> OTHER INFORMATION: synthetic

<400> SEQUENCE: 47

Cys Lys Gly Val His Val Glu Asp Gln Tyr Arg Pro Trp Cys
1 5 10

<210> SEQ ID NO 48
<211> LENGTH: 14
<212> TYPE: PRT
<213> ORGANISM: Artificial
<220> FEATURE:
<223> OTHER INFORMATION: synthetic

<400> SEQUENCE: 48

Cys Gln Trp Glu Thr Asn Gly Gly Trp Thr Arg Pro Lys Cys
1 5 10

<210> SEQ ID NO 49
<211> LENGTH: 14
<212> TYPE: PRT
<213> ORGANISM: Artificial
<220> FEATURE:
<223> OTHER INFORMATION: synthetic

<400> SEQUENCE: 49

Cys Trp Ser Pro Asp Ser Ala Trp Glu Lys Pro Lys Cys Cys
1 5 10

<210> SEQ ID NO 50
<211> LENGTH: 14
<212> TYPE: PRT
<213> ORGANISM: Artificial
<220> FEATURE:
<223> OTHER INFORMATION: synthetic

<400> SEQUENCE: 50

Cys Trp Glu Gly Pro Val Ser Pro Ala Gly Leu Pro Arg Cys
1 5 10

<210> SEQ ID NO 51
<211> LENGTH: 14
<212> TYPE: PRT
<213> ORGANISM: Artificial
<220> FEATURE:
<223> OTHER INFORMATION: synthetic

<400> SEQUENCE: 51

Cys Glu Tyr Asp Asn Gln Ser His Trp Ala Arg Pro Lys Cys 1 5 10

<210> SEQ ID NO 52
<211> LENGTH: 14
<212> TYPE: PRT
<213> ORGANISM: Artificial
<220> FEATURE:
<223> OTHER INFORMATION: synthetic

<400> SEQUENCE: 52

Cys Gly Met Thr Leu Arg Gly Trp Arg Asp Pro Arg Met Cys
1 5 10

<210> SEQ ID NO 53
<211> LENGTH: 14
<212> TYPE: PRT
<213> ORGANISM: Artificial
<220> FEATURE:
<223> OTHER INFORMATION: synthetic

<400> SEQUENCE: 53

Cys Arg Val Ala Gln Ala Glu Gly Trp Ala Pro Pro Arg Cys
1 5 10

<210> SEQ ID NO 54
<211> LENGTH: 14
<212> TYPE: PRT
<213> ORGANISM: Artificial
<220> FEATURE:
<223> OTHER INFORMATION: synthetic

<400> SEQUENCE: 54

Cys Ile Arg Asn Tyr His Val Phe Pro Pro Gly Lys Val Cys
1 5 10

<210> SEQ ID NO 55
<211> LENGTH: 14
<212> TYPE: PRT
<213> ORGANISM: Artificial
<220> FEATURE:
<223> OTHER INFORMATION: synthetic

<400> SEQUENCE: 55

Cys Ala Lys Asn Tyr Leu Leu Tyr Pro Pro Ile Arg Gln Cys
1 5 10

<210> SEQ ID NO 56
<211> LENGTH: 14
<212> TYPE: PRT
<213> ORGANISM: Artificial
<220> FEATURE:
<223> OTHER INFORMATION: synthetic

<400> SEQUENCE: 56

Cys Arg Thr Gly Thr Val Ser Trp Gly Gln Tyr Lys Gly Cys
1 5 10

<210> SEQ ID NO 57
<211> LENGTH: 14
<212> TYPE: PRT
<213> ORGANISM: Artificial
<220> FEATURE:
<223> OTHER INFORMATION: synthetic

<400> SEQUENCE: 57

Cys Lys Leu Asp Tyr Arg Ile Gly Glu Asn Phe Ala Gln Cys
1 5 10

<210> SEQ ID NO 58
<211> LENGTH: 14
<212> TYPE: PRT
<213> ORGANISM: Artificial
<220> FEATURE:
<223> OTHER INFORMATION: synthetic

<400> SEQUENCE: 58

Cys Lys Tyr Glu Val Ser Gln Glu Ala Arg Glu Arg Trp Cys
1 5 10

<210> SEQ ID NO 59
<211> LENGTH: 14
<212> TYPE: PRT
<213> ORGANISM: Artificial
<220> FEATURE:
<223> OTHER INFORMATION: synthetic

<400> SEQUENCE: 59

Cys Gly Thr His Pro Tyr Gly Ser Pro Gln Phe Met Thr Cys
1 5 10

<210> SEQ ID NO 60
<211> LENGTH: 14
<212> TYPE: PRT
<213> ORGANISM: Artificial
<220> FEATURE:
<223> OTHER INFORMATION: synthetic

<400> SEQUENCE: 60

Cys Leu Val Gly Glu Thr Arg Leu Gly Ile Trp Leu Gly Cys
1 5 10

<210> SEQ ID NO 61
<211> LENGTH: 14
<212> TYPE: PRT
<213> ORGANISM: Artificial
<220> FEATURE:
<223> OTHER INFORMATION: synthetic

<400> SEQUENCE: 61

Cys Ser Ser Ser Cys Ala Lys Trp Ala Trp Ser His Cys Cys
1 5 10

<210> SEQ ID NO 62
<211> LENGTH: 14
<212> TYPE: PRT
<213> ORGANISM: Artificial
<220> FEATURE:
<223> OTHER INFORMATION: synthetic

<400> SEQUENCE: 62

Cys Arg Gly Gly Gly Thr Asp Ala Gln Gly Trp Tyr Thr Cys
1 5 10

<210> SEQ ID NO 63
<211> LENGTH: 14
<212> TYPE: PRT
<213> ORGANISM: Artificial
<220> FEATURE:
<223> OTHER INFORMATION: synthetic

<400> SEQUENCE: 63

Cys Arg Arg Pro Val Val Asp Ala Gly Trp Asn Met Ser Cys
1 5 10

<210> SEQ ID NO 64

<211> LENGTH: 14
<212> TYPE: PRT
<213> ORGANISM: Artificial
<220> FEATURE:
<223> OTHER INFORMATION: synthetic

<400> SEQUENCE: 64

Cys Ser Gly Ala Ser Ala Trp Arg Gly Glu Met Gln His Cys
1 5 10

<210> SEQ ID NO 65
<211> LENGTH: 14
<212> TYPE: PRT
<213> ORGANISM: Artificial
<220> FEATURE:
<223> OTHER INFORMATION: synthetic

<400> SEQUENCE: 65

Cys Lys Asp Leu Ala Glu Gly Gly Pro Ala Ile Gly Ser Cys
1 5 10

<210> SEQ ID NO 66
<211> LENGTH: 14
<212> TYPE: PRT
<213> ORGANISM: Artificial
<220> FEATURE:
<223> OTHER INFORMATION: synthetic

<400> SEQUENCE: 66

Cys Tyr Lys Pro Leu Tyr Ala Gln Gly Trp Gly Trp Tyr Cys
1 5 10

<210> SEQ ID NO 67
<211> LENGTH: 14
<212> TYPE: PRT
<213> ORGANISM: Artificial
<220> FEATURE:
<223> OTHER INFORMATION: synthetic

<400> SEQUENCE: 67

Cys Ser Pro Arg Thr Arg Thr Gly Thr Ala Arg Ser Arg Cys
1 5 10

<210> SEQ ID NO 68
<211> LENGTH: 14
<212> TYPE: PRT
<213> ORGANISM: Artificial
<220> FEATURE:
<223> OTHER INFORMATION: synthetic

<400> SEQUENCE: 68

Cys Asp Pro Lys Arg Asn Pro Asp Arg Ile Met His Pro Cys
1 5 10

<210> SEQ ID NO 69
<211> LENGTH: 25
<212> TYPE: PRT
<213> ORGANISM: Artificial
<220> FEATURE:
<223> OTHER INFORMATION: synthetic

<400> SEQUENCE: 69

Cys Val Lys Leu Thr Gly Pro Gly Val Gly Lys Ala Met Tyr Gly Pro
1 5 10 15

Gly Ile Gln Lys Phe Glu Lys Pro Cys
20 25

<210> SEQ ID NO 70
<211> LENGTH: 20
<212> TYPE: PRT
<213> ORGANISM: Artificial
<220> FEATURE:
<223> OTHER INFORMATION: synthetic

<400> SEQUENCE: 70

His Ser Phe Gly Asp Leu Ser Ile Ser Pro Asn Ser Leu Thr Ala Trp
1 5 10 15

Pro Gly Thr Leu
20

<210> SEQ ID NO 71
<211> LENGTH: 12
<212> TYPE: PRT
<213> ORGANISM: Artificial
<220> FEATURE:
<223> OTHER INFORMATION: synthetic

<400> SEQUENCE: 71

Trp Leu Met Arg Ala Ala Trp Pro Trp Asp Tyr Thr
1 5 10

<210> SEQ ID NO 72
<211> LENGTH: 15
<212> TYPE: PRT
<213> ORGANISM: Artificial
<220> FEATURE:
<223> OTHER INFORMATION: synthetic

<400> SEQUENCE: 72

Asn Leu Arg Ser Thr Ser Phe Phe Glu Leu Trp Ala Lys Trp Pro
1 5 10 15

<210> SEQ ID NO 73
<211> LENGTH: 15
<212> TYPE: PRT
<213> ORGANISM: Artificial
<220> FEATURE:
<223> OTHER INFORMATION: synthetic

<400> SEQUENCE: 73

Gly Glu Phe Pro Asp Trp Asp Asn Leu Pro Leu Leu Cys Glu Gly
1 5 10 15

<210> SEQ ID NO 74
<211> LENGTH: 15
<212> TYPE: PRT
<213> ORGANISM: Artificial
<220> FEATURE:
<223> OTHER INFORMATION: synthetic

<400> SEQUENCE: 74

Gly Arg Pro Gln Trp Tyr Leu Gln Phe Glu Asp Tyr Trp Arg Ser
1 5 10 15

<210> SEQ ID NO 75
<211> LENGTH: 15
<212> TYPE: PRT
<213> ORGANISM: Artificial
<220> FEATURE:
<223> OTHER INFORMATION: synthetic

<400> SEQUENCE: 75

Asp Ser Leu Arg Val Asp Glu His His Glu Val Trp Val Pro Met
1 5 10 15

<210> SEQ ID NO 76
<211> LENGTH: 16
<212> TYPE: PRT
<213> ORGANISM: Artificial
<220> FEATURE:
<223> OTHER INFORMATION: synthetic

<400> SEQUENCE: 76

Asp Trp Val Pro Phe Phe Gly Phe Phe Phe Ser Arg Leu Gln Leu Pro
1 5 10 15

<210> SEQ ID NO 77
<211> LENGTH: 15
<212> TYPE: PRT
<213> ORGANISM: Artificial
<220> FEATURE:
<223> OTHER INFORMATION: synthetic

<400> SEQUENCE: 77

Asn Trp Pro Arg Trp Trp Glu Glu Phe Val Asp Lys His Ser Ser
1 5 10 15

<210> SEQ ID NO 78
<211> LENGTH: 21
<212> TYPE: PRT
<213> ORGANISM: Artificial
<220> FEATURE:
<223> OTHER INFORMATION: synthetic

<400> SEQUENCE: 78

Val Arg Phe His Leu Ala Gly Trp Leu Pro Ala Val Val Ser Phe Val
1 5 10 15

Ile Phe Ser Asp His
20

<210> SEQ ID NO 79
<211> LENGTH: 21
<212> TYPE: PRT
<213> ORGANISM: Artificial
<220> FEATURE:
<223> OTHER INFORMATION: synthetic

<400> SEQUENCE: 79

Asp Gly Leu Arg Ser Asp Gly Ser Trp Leu Ala Arg Phe Val Phe Asn
1 5 10 15

Gly Ser Gly Phe Tyr
20

<210> SEQ ID NO 80
<211> LENGTH: 18
<212> TYPE: PRT
<213> ORGANISM: Artificial
<220> FEATURE:
<223> OTHER INFORMATION: synthetic

<400> SEQUENCE: 80

Gly Asn Phe Thr Ala Ser Thr Ala Ser Trp Gly Asp Glu Leu Leu Ala
1 5 10 15

Leu Tyr

<210> SEQ ID NO 81
<211> LENGTH: 13
<212> TYPE: PRT
<213> ORGANISM: Artificial
<220> FEATURE:
<223> OTHER INFORMATION: synthetic

<400> SEQUENCE: 81

Phe Val Trp Glu Glu His Val Gly Phe Leu Met Arg Asn
1 5 10

<210> SEQ ID NO 82
<211> LENGTH: 14
<212> TYPE: PRT
<213> ORGANISM: Artificial
<220> FEATURE:
<223> OTHER INFORMATION: synthetic

<400> SEQUENCE: 82

Asn Trp Pro Arg Trp Glu Glu Phe Val Asp Lys His Ser Ser
1 5 10

<210> SEQ ID NO 83
<211> LENGTH: 21
<212> TYPE: PRT
<213> ORGANISM: Artificial
<220> FEATURE:
<223> OTHER INFORMATION: synthetic

<400> SEQUENCE: 83

Phe Ala His Glu Gly Ser Ala Ser Phe Arg Leu Ser Ser Lys Val Glu
1 5 10 15

Asp Trp Val Ser Arg
20

<210> SEQ ID NO 84
<211> LENGTH: 15
<212> TYPE: PRT
<213> ORGANISM: Artificial
<220> FEATURE:
<223> OTHER INFORMATION: synthetic

<400> SEQUENCE: 84

Cys Val Phe Tyr Ala Asn Val Glu Glu Glu Val Gln Cys Trp Leu
1 5 10 15

<210> SEQ ID NO 85
<211> LENGTH: 21
<212> TYPE: PRT
<213> ORGANISM: Artificial
<220> FEATURE:
<223> OTHER INFORMATION: synthetic

<400> SEQUENCE: 85

Phe Cys Val Arg Leu Met Cys Ser Gly Leu Ile Pro Phe Phe Val Leu
1 5 10 15

Cys Cys Phe Phe Ala
20

<210> SEQ ID NO 86
<211> LENGTH: 21
<212> TYPE: PRT
<213> ORGANISM: Artificial
<220> FEATURE:
<223> OTHER INFORMATION: synthetic

<400> SEQUENCE: 86

Phe Ser Arg Ala Asp Phe Phe Pro Leu Ser Tyr Ser Leu Ser Ser Val
1 5 10 15

Pro Ser Thr Ala Leu
20

<210> SEQ ID NO 87
<211> LENGTH: 22
<212> TYPE: PRT
<213> ORGANISM: Artificial
<220> FEATURE:
<223> OTHER INFORMATION: synthetic

<400> SEQUENCE: 87

Phe Ser Pro Tyr Pro Pro Asp Ile Val His Thr Thr Ala Phe Ser Ser
1 5 10 15

Phe Val Asn Pro Val Asp
20

<210> SEQ ID NO 88
<211> LENGTH: 21
<212> TYPE: PRT
<213> ORGANISM: Artificial
<220> FEATURE:
<223> OTHER INFORMATION: synthetic

<400> SEQUENCE: 88

Ser Ser Phe Phe Tyr Ser Ala Leu Thr Pro Ser Phe Pro Ser Pro Tyr
1 5 10 15

Ser Gln Ser Ser Arg
20

<210> SEQ ID NO 89
<211> LENGTH: 21
<212> TYPE: PRT
<213> ORGANISM: Artificial
<220> FEATURE:
<223> OTHER INFORMATION: synthetic

<400> SEQUENCE: 89

Arg Phe Phe Ala Phe Pro Met Val Cys Ala Ser Phe Phe Leu Val Ala
1 5 10 15

Ile Ala Phe Phe Pro
20

<210> SEQ ID NO 90
<211> LENGTH: 22
<212> TYPE: PRT
<213> ORGANISM: Artificial
<220> FEATURE:
<223> OTHER INFORMATION: synthetic

<400> SEQUENCE: 90

Pro Leu Pro Pro Ser Arg Phe Phe Ile Thr Val Cys Leu Thr Phe Leu
1 5 10 15

Phe Ser Leu Ser Phe Phe
20

<210> SEQ ID NO 91
<211> LENGTH: 21
<212> TYPE: PRT
<213> ORGANISM: Artificial
<220> FEATURE:
<223> OTHER INFORMATION: synthetic

<400> SEQUENCE: 91

Val Arg Pro Cys Val Ala Ser Leu Leu Leu Phe Phe Cys Leu Leu Phe
1 5 10 15

Leu Leu Leu Pro Ser
20

<210> SEQ ID NO 92
<211> LENGTH: 21
<212> TYPE: PRT
<213> ORGANISM: Artificial
<220> FEATURE:
<223> OTHER INFORMATION: synthetic

<400> SEQUENCE: 92

Ile Cys Phe Pro Phe Asn Thr Arg Tyr Cys Ile Phe Ala Met Met Val
1 5 10 15

Ser Ser Leu Val Phe
20

<210> SEQ ID NO 93
<211> LENGTH: 21
<212> TYPE: PRT
<213> ORGANISM: Artificial
<220> FEATURE:
<223> OTHER INFORMATION: synthetic

<400> SEQUENCE: 93

Gln Gln Ala Gly Ser Tyr Pro Gly Cys Ile Asp Tyr Tyr Tyr Cys His
1 5 10 15

Ala Ser Ala Ile Gly
20

<210> SEQ ID NO 94
<211> LENGTH: 14
<212> TYPE: PRT
<213> ORGANISM: Artificial
<220> FEATURE:
<223> OTHER INFORMATION: synthetic

<400> SEQUENCE: 94

Cys Leu Pro Ala Tyr Gly Cys Lys Ser Phe Arg Glu Pro Phe
1 5 10

<210> SEQ ID NO 95
<211> LENGTH: 21
<212> TYPE: PRT
<213> ORGANISM: Artificial
<220> FEATURE:
<223> OTHER INFORMATION: synthetic

<400> SEQUENCE: 95

Arg His Phe Val Pro Leu Tyr Leu Ser Val Ser Tyr Asp Gly Phe Ser
1 5 10 15

Arg Gly Ala Ser Ile
20

<210> SEQ ID NO 96
<211> LENGTH: 20
<212> TYPE: PRT
<213> ORGANISM: Artificial
<220> FEATURE:
<223> OTHER INFORMATION: synthetic

<400> SEQUENCE: 96

Pro Ile Ile His Pro His Pro Pro Arg Ile Ala Met Arg Val Ser Ile
1 5 10 15

Ser Pro Phe Pro
20

<210> SEQ ID NO 97
<211> LENGTH: 21

<212> TYPE: PRT
<213> ORGANISM: Artificial
<220> FEATURE:
<223> OTHER INFORMATION: synthetic

<400> SEQUENCE: 97

Thr Pro Thr Asp Ser Thr Val Arg Gly Ser Ser Thr Met Asp Gly Phe
1 5 10 15

Leu Lys Ser Val Tyr
20

<210> SEQ ID NO 98
<211> LENGTH: 21
<212> TYPE: PRT
<213> ORGANISM: Artificial
<220> FEATURE:
<223> OTHER INFORMATION: synthetic

<400> SEQUENCE: 98

Thr Ala Ser Phe Trp Arg Ser Val Ser Phe Pro Trp Val Leu Ser Phe
1 5 10 15

Leu Ala Phe Ser His
20

<210> SEQ ID NO 99
<211> LENGTH: 15
<212> TYPE: PRT
<213> ORGANISM: Artificial
<220> FEATURE:
<223> OTHER INFORMATION: synthetic

<400> SEQUENCE: 99

Gly Ala Gln Val Asn Arg Lys Cys Ala Trp His Pro Arg His Ile
1 5 10 15

<210> SEQ ID NO 100
<211> LENGTH: 15
<212> TYPE: PRT
<213> ORGANISM: Artificial
<220> FEATURE:
<223> OTHER INFORMATION: synthetic

<400> SEQUENCE: 100

Val Ala Lys Lys Leu Trp Val Pro Gln Val Ser Gly Ser Asn Phe
1 5 10 15

<210> SEQ ID NO 101
<211> LENGTH: 6
<212> TYPE: PRT
<213> ORGANISM: Artificial
<220> FEATURE:
<223> OTHER INFORMATION: synthetic

<400> SEQUENCE: 101

His Trp Gly Val Tyr Arg
1 5

<210> SEQ ID NO 102
<211> LENGTH: 15
<212> TYPE: PRT
<213> ORGANISM: Artificial
<220> FEATURE:
<223> OTHER INFORMATION: synthetic

<400> SEQUENCE: 102

Arg Glu Lys Arg Trp Ile Phe Ser Asp Leu Thr His Thr Cys Ile
1 5 10 15

<210> SEQ ID NO 103
<211> LENGTH: 12
<212> TYPE: PRT
<213> ORGANISM: Artificial
<220> FEATURE:
<223> OTHER INFORMATION: synthetic

<400> SEQUENCE: 103

Thr Cys Leu Trp Ser Asp Leu Arg Ala Gln Cys Ile
1 5 10

<210> SEQ ID NO 104
<211> LENGTH: 41
<212> TYPE: PRT
<213> ORGANISM: Artificial
<220> FEATURE:
<223> OTHER INFORMATION: synthetic

<400> SEQUENCE: 104

Cys Phe Asn Ser Thr Trp Phe Asn Thr Pro Gly Ser Thr Ile Ile Phe
1 5 10 15

Lys Thr Pro Gly Ser Phe Ile Glu Ser Glu Asn Asn Ser Asn Gly Gly
20 25 30

Asp Ser Leu Trp Asp Gln Ser Leu Cys
35 40

<210> SEQ ID NO 105
<211> LENGTH: 36
<212> TYPE: PRT
<213> ORGANISM: Artificial
<220> FEATURE:
<223> OTHER INFORMATION: synthetic

<400> SEQUENCE: 105

Cys Phe Asn Ser Thr Trp Phe Asn Thr Pro Gly Ser Thr Ile Ile Phe
1 5 10 15

Lys Cys Thr Pro Gly Ser Cys Phe Ile Glu Ser Glu Asn Asn Ser Asn
20 25 30

Gly Gly Asp Cys
35

<210> SEQ ID NO 106
<211> LENGTH: 433
<212> TYPE: PRT
<213> ORGANISM: Artificial
<220> FEATURE:
<223> OTHER INFORMATION: synthetic

<400> SEQUENCE: 106

Lys Lys Val Val Leu Gly Lys Lys Gly Asp Thr Val Glu Leu Thr Cys
1 5 10 15

Thr Ala Ser Gln Lys Lys Ser Ile Gln Phe His Trp Lys Asn Ser Asn
20 25 30

Gln Ile Lys Ile Leu Gly Asn Gln Gly Ser Phe Leu Thr Lys Gly Pro
35 40 45

Ser Lys Leu Asn Asp Arg Ala Asp Ser Arg Arg Ser Leu Trp Asp Gln
50 55 60

Gly Asn Phe Pro Leu Ile Ile Lys Asn Leu Lys Ile Glu Asp Ser Asp
65 70 75 80

Thr Tyr Ile Cys Glu Val Glu Asp Gln Lys Glu Glu Val Gln Leu Leu
85 90 95

```
Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Val Tyr Lys Lys Glu Gly Glu
            180                 185                 190

Gln Val Glu Phe Ser Phe Pro Leu Ala Phe Thr Val Glu Lys Leu Thr
        195                 200                 205

Gly Ser Gly Glu Leu Trp Trp Gln Ala Glu Arg Ala Ser Ser Ser Lys
    210                 215                 220

Ser Trp Ile Thr Phe Asp Leu Lys Asn Lys Glu Val Ser Val Lys Arg
225                 230                 235                 240

Val Thr Gln Asp Pro Lys Leu Gln Met Gly Lys Lys Leu Pro Leu His
                245                 250                 255

Leu Thr Leu Pro Gln Ala Leu Pro Gln Tyr Ala Gly Ser Gly Asn Leu
            260                 265                 270

Thr Leu Ala Leu Glu Ala Lys Thr Gly Lys Leu His Gln Glu Val Asn
        275                 280                 285

Leu Val Val Met Arg Ala Thr Gln Leu Gln Lys Asn Leu Thr Cys Glu
    290                 295                 300

Val Trp Gly Pro Thr Ser Pro Lys Leu Met Leu Ser Leu Lys Leu Glu
305                 310                 315                 320

Asn Lys Glu Ala Lys Val Ser Lys Arg Glu Lys Ala Val Trp Val Leu
                325                 330                 335

Asn Pro Glu Ala Gly Met Trp Gln Cys Leu Leu Ser Asp Ser Gly Gln
            340                 345                 350

Val Leu Leu Glu Ser Asn Ile Lys Val Leu Pro Thr Trp Ser Thr Pro
        355                 360                 365

Val Gln Pro Met Ala Leu Ile Val Leu Gly Gly Val Ala Gly Leu Leu
    370                 375                 380

Leu Phe Ile Gly Leu Gly Ile Phe Phe Cys Val Arg Cys Arg His Arg
385                 390                 395                 400

Arg Arg Gln Ala Glu Arg Met Ser Gln Ile Lys Arg Leu Leu Ser Glu
                405                 410                 415

Lys Lys Thr Cys Gln Cys Pro His Arg Phe Gln Lys Thr Cys Ser Pro
            420                 425                 430

Ile


<210> SEQ ID NO 107
<211> LENGTH: 127
<212> TYPE: PRT
<213> ORGANISM: Artificial
<220> FEATURE:
<223> OTHER INFORMATION: synthetic

<400> SEQUENCE: 107

Gln Val Gln Leu Lys Gln Ser Gly Thr Glu Leu Val Arg Pro Gly Thr
1               5                   10                  15

Ser Val Lys Met Ser Cys Lys Ala Ala Gly Tyr Thr Phe Thr Asp Tyr
            20                  25                  30
```

```
Trp Ile Gly Trp Val Lys Gln Arg Pro Gly His Gly Leu Glu Trp Ile
        35                  40                  45

Gly Asp Phe Tyr Pro Gly Gly Asp Tyr Thr Leu Tyr Ser Glu Asn Phe
    50                  55                  60

Met Gly Lys Ala Ser Leu Thr Ala Asp Thr Ser Ser Asn Thr Ala Tyr
65                  70                  75                  80

Met Gln Leu Ser Ser Leu Thr Ser Glu Asp Ser Ala Ile Tyr Tyr Cys
                85                  90                  95

Ala Arg Gly His Tyr Tyr Gly Tyr Ser Tyr Ala Trp Phe Ala Tyr Trp
            100                 105                 110

Gly Gln Gly Thr Leu Val Thr Val Ser Ser Gly Glu Cys Gly Arg
        115                 120                 125


<210> SEQ ID NO 108
<211> LENGTH: 6
<212> TYPE: PRT
<213> ORGANISM: Artificial
<220> FEATURE:
<223> OTHER INFORMATION: synthetic

<400> SEQUENCE: 108

Phe Asn Ser Thr Trp Asn
1               5


<210> SEQ ID NO 109
<211> LENGTH: 6
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 109

Phe Asn Ser Thr Trp Xaa
1               5


<210> SEQ ID NO 110
<211> LENGTH: 6
<212> TYPE: PRT
<213> ORGANISM: Artificial
<220> FEATURE:
<223> OTHER INFORMATION: synthetic

<400> SEQUENCE: 110

Phe Asn Ser Thr Tyr Asn
1               5


<210> SEQ ID NO 111
<211> LENGTH: 6
<212> TYPE: PRT
<213> ORGANISM: Artificial
<220> FEATURE:
<223> OTHER INFORMATION: synthetic

<400> SEQUENCE: 111

Phe Asn Asp Thr Gly Ser
1               5


<210> SEQ ID NO 112
<211> LENGTH: 6
<212> TYPE: PRT
<213> ORGANISM: Artificial
```

<220> FEATURE:
<223> OTHER INFORMATION: synthetic

<400> SEQUENCE: 112

Phe Asn Asn Thr Glu Val
1 5

<210> SEQ ID NO 113
<211> LENGTH: 6
<212> TYPE: PRT
<213> ORGANISM: Artificial
<220> FEATURE:
<223> OTHER INFORMATION: synthetic

<400> SEQUENCE: 113

Phe Asn Asn Ser Ile Leu
1 5

<210> SEQ ID NO 114
<211> LENGTH: 6
<212> TYPE: PRT
<213> ORGANISM: Artificial
<220> FEATURE:
<223> OTHER INFORMATION: synthetic

<400> SEQUENCE: 114

Phe Asn Tyr Thr Phe Ser
1 5

<210> SEQ ID NO 115
<211> LENGTH: 6
<212> TYPE: PRT
<213> ORGANISM: Artificial
<220> FEATURE:
<223> OTHER INFORMATION: synthetic

<400> SEQUENCE: 115

Phe Asn Asn Thr Cys Ile
1 5

<210> SEQ ID NO 116
<211> LENGTH: 6
<212> TYPE: PRT
<213> ORGANISM: Artificial
<220> FEATURE:
<223> OTHER INFORMATION: synthetic

<400> SEQUENCE: 116

Phe Asn Ser Thr Tyr Met
1 5

<210> SEQ ID NO 117
<211> LENGTH: 6
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 117

Phe Asn Xaa Ser Ile Xaa
1 5

<210> SEQ ID NO 118
<211> LENGTH: 6
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 118

Phe Asn Gly Thr Tyr Xaa
1 5

<210> SEQ ID NO 119
<211> LENGTH: 15
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 119

Asp Gly Gly Val Asn Xaa Xaa Xaa Asn Ser Xaa Asn Glu Thr Phe
1 5 10 15

<210> SEQ ID NO 120
<211> LENGTH: 12
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 120

Asp Gly Gly Xaa Asn Xaa Xaa Xaa Asn Glu Thr Phe
1 5 10

<210> SEQ ID NO 121
<211> LENGTH: 20
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (6)..(13)
<223> OTHER INFORMATION: Xaa can be any naturally occurring amino acid

<400> SEQUENCE: 121

Asp Gly Gly Asn Asn Xaa Xaa Xaa Xaa Xaa Xaa Xaa Xaa Thr Asn Thr
1 5 10 15

Thr Glu Ile Phe
20

<210> SEQ ID NO 122
<211> LENGTH: 19
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (6)..(12)
<223> OTHER INFORMATION: Xaa can be any naturally occurring amino acid

<400> SEQUENCE: 122

Asp Gly Gly Asn Asn Xaa Xaa Xaa Xaa Xaa Xaa Xaa Thr Asn Thr Thr
1 5 10 15

Glu Thr Phe

<210> SEQ ID NO 123
<211> LENGTH: 18
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (6)..(11)
<223> OTHER INFORMATION: Xaa can be any naturally occurring amino acid

<400> SEQUENCE: 123

Asp Gly Gly Ala Asn Xaa Xaa Xaa Xaa Xaa Xaa Asn Ser Ser Asn Glu
1 5 10 15

Thr Phe

<210> SEQ ID NO 124
<211> LENGTH: 14
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 124

Asp Gly Gly Gln Xaa Xaa Xaa Xaa Ser Xaa Thr Glu Thr Phe
1 5 10

<210> SEQ ID NO 125
<211> LENGTH: 12
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 125

Asp Gly Gly Lys Asn Xaa Asn Gly Ser Glu Thr Leu
1 5 10

<210> SEQ ID NO 126
<211> LENGTH: 16
<212> TYPE: PRT

<213> ORGANISM: Artificial
<220> FEATURE:
<223> OTHER INFORMATION: synthetic
<220> FEATURE:
<221> NAME/KEY: misc_feature
<222> LOCATION: (6)..(9)
<223> OTHER INFORMATION: Xaa can be any naturally occurring amino acid

<400> SEQUENCE: 126

Asp Gly Gly Asn Asn Xaa Xaa Xaa Xaa Thr Ser Thr Asn Glu Thr Phe
1 5 10 15

<210> SEQ ID NO 127
<211> LENGTH: 16
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 127

Asp Asn Pro Trp Asn Xaa Xaa Xaa Thr Ser Asn Xaa Asn Ala Thr Phe
1 5 10 15

<210> SEQ ID NO 128
<211> LENGTH: 16
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (6)..(9)
<223> OTHER INFORMATION: Xaa can be any naturally occurring amino acid

<400> SEQUENCE: 128

Asp Gly Gly Ala Asn Xaa Xaa Xaa Xaa Asn Thr Thr Asn Glu Thr Phe
1 5 10 15

<210> SEQ ID NO 129
<211> LENGTH: 14
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (6)..(7)
<223> OTHER INFORMATION: Xaa can be any naturally occurring amino acid

<400> SEQUENCE: 129

Asp Gly Gly Asn Asn Xaa Xaa Asn Ser Thr Asn Glu Thr Phe
1 5 10

<210> SEQ ID NO 130
<211> LENGTH: 12
<212> TYPE: PRT
<213> ORGANISM: Artificial
<220> FEATURE:
<223> OTHER INFORMATION: synthetic

<400> SEQUENCE: 130

Asp Gly Gly Asn Gln Ser Asn Val Thr Glu Ile Phe
1 5 10

<210> SEQ ID NO 131
<211> LENGTH: 16
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (4)..(12)
<223> OTHER INFORMATION: Xaa can be any naturally occurring amino acid

<400> SEQUENCE: 131

Asp Gly Gly Xaa Xaa Xaa Xaa Xaa Xaa Xaa Xaa Xaa Asn Glu Thr Phe
1 5 10 15

<210> SEQ ID NO 132
<211> LENGTH: 12
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 132

Asp Gly Asn Asn Xaa Xaa Ser Xaa Ser Glu Thr Phe
1 5 10

<210> SEQ ID NO 133
<211> LENGTH: 14
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 133

Asp Gly Gly Arg Thr Xaa Glu Ser Asn Asp Thr Glu Ile Phe
1 5 10

<210> SEQ ID NO 134
<211> LENGTH: 433
<212> TYPE: PRT
<213> ORGANISM: Artificial
<220> FEATURE:
<223> OTHER INFORMATION: synthetic

<400> SEQUENCE: 134

Lys Phe Asn Ser Thr Trp Phe Lys Gly Asp Thr Val Glu Leu Thr Cys
1 5 10 15

Thr Ala Ser Gln Lys Lys Ser Ile Gln Phe His Trp Lys Asn Ser Asn
20 25 30

Gln Ile Lys Ile Leu Gly Asn Gln Gly Ser Phe Leu Thr Lys Gly Pro
35 40 45

Ser Lys Leu Asn Asp Arg Ala Asp Ser Arg Arg Ser Leu Trp Asp Gln
50 55 60

Gly Asn Phe Pro Leu Ile Ile Lys Asn Leu Lys Ile Glu Ser Glu Ile
65 70 75 80

```
Phe Tyr Ile Cys Glu Val Glu Asp Gln Lys Glu Glu Leu Phe Ile Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Val Tyr Lys Lys Glu Gly Glu
            180                 185                 190

Gln Val Glu Phe Ser Phe Pro Leu Ala Phe Thr Val Glu Lys Leu Thr
        195                 200                 205

Gly Ser Gly Glu Leu Trp Trp Gln Ala Glu Arg Ala Ser Ser Ser Lys
    210                 215                 220

Ser Trp Ile Thr Phe Asp Leu Lys Asn Lys Glu Val Ser Val Lys Arg
225                 230                 235                 240

Val Thr Gln Asp Pro Lys Leu Gln Met Gly Lys Lys Leu Pro Leu His
                245                 250                 255

Leu Thr Leu Pro Gln Ala Leu Pro Gln Tyr Ala Gly Ser Gly Asn Leu
            260                 265                 270

Thr Leu Ala Leu Glu Ala Lys Thr Gly Lys Leu His Gln Glu Val Asn
        275                 280                 285

Leu Val Val Met Arg Ala Thr Gln Leu Gln Lys Asn Leu Thr Cys Glu
    290                 295                 300

Val Trp Gly Pro Thr Ser Pro Lys Leu Met Leu Ser Leu Lys Leu Glu
305                 310                 315                 320

Asn Lys Glu Ala Lys Val Ser Lys Arg Glu Lys Ala Val Trp Val Leu
                325                 330                 335

Asn Pro Glu Ala Gly Met Trp Gln Cys Leu Leu Ser Asp Ser Gly Gln
            340                 345                 350

Val Leu Leu Glu Ser Asn Ile Lys Val Leu Pro Thr Trp Ser Thr Pro
        355                 360                 365

Val Gln Pro Met Ala Leu Ile Val Leu Gly Gly Val Ala Gly Leu Leu
    370                 375                 380

Leu Phe Ile Gly Leu Gly Ile Phe Phe Cys Val Arg Cys Arg His Arg
385                 390                 395                 400

Arg Arg Gln Ala Glu Arg Met Ser Gln Ile Lys Arg Leu Leu Ser Glu
                405                 410                 415

Lys Lys Thr Cys Gln Cys Pro His Arg Phe Gln Lys Thr Cys Ser Pro
            420                 425                 430

Ile


<210> SEQ ID NO 135
<211> LENGTH: 127
<212> TYPE: PRT
<213> ORGANISM: Artificial
<220> FEATURE:
<223> OTHER INFORMATION: synthetic

<400> SEQUENCE: 135

Gln Val Gln Leu Lys Gln Ser Gly Thr Glu Leu Val Arg Pro Gly Thr
```

-continued

```
1               5                   10                  15

Ser Val Phe Asn Ser Thr Trp Phe Ala Gly Tyr Thr Phe Thr Asp Tyr
            20                  25                  30

Trp Ile Gly Trp Val Lys Gln Arg Pro Gly His Gly Leu Glu Trp Ile
        35                  40                  45

Gly Asp Phe Tyr Pro Gly Gly Asp Tyr Thr Leu Tyr Ser Glu Asn Phe
    50                  55                  60

Met Gly Lys Phe Ile Glu Ser Glu Asp Thr Ser Ser Asn Thr Ile Phe
65                  70                  75                  80

Lys Gln Leu Ser Ser Leu Thr Ser Glu Asp Ser Ala Ile Tyr Tyr Cys
                85                  90                  95

Ala Arg Gly His Tyr Tyr Gly Tyr Ser Tyr Ala Trp Phe Ala Tyr Trp
            100                 105                 110

Gly Gln Gly Thr Leu Val Thr Val Ser Ser Gly Glu Cys Gly Arg
        115                 120                 125


<210> SEQ ID NO 136
<211> LENGTH: 19
<212> TYPE: DNA
<213> ORGANISM: Artificial
<220> FEATURE:
<223> OTHER INFORMATION: synthetic

<400> SEQUENCE: 136

ggtcagacga ttggccttg                                                19


<210> SEQ ID NO 137
<211> LENGTH: 80
<212> TYPE: DNA
<213> ORGANISM: Artificial
<220> FEATURE:
<223> OTHER INFORMATION: synthetic

<400> SEQUENCE: 137

gtgtgtaaaa ttaactgcac caggagtagg aaaagcaatg tatggccctg ggattcaaaa     60

attcgaaaag ccatgtgctg                                               80


<210> SEQ ID NO 138
<211> LENGTH: 80
<212> TYPE: DNA
<213> ORGANISM: Artificial
<220> FEATURE:
<223> OTHER INFORMATION: synthetic

<400> SEQUENCE: 138

cagcacatgg cttttcgaat ttttgaatcc cagggccata cattgctttt cctactcctg     60

gtgcagttaa ttttacacac                                               80
```

What is claimed is:

1. A method for improved prediction of the region on the surface of a proteinaceous material representing a binding surface that associates with a predetermined binding molecule, comprising:

(a) screening a peptide library with said predetermined binding molecule to identify a plurality of peptides that bind to said binding molecule;

(b) determining the amino acid sequence of each identified peptide;

(c) assigning a symbol to each class of amino acid residue represented in the library and presenting each said sequence as a string of said symbols;

(d) calculating the frequency of occurrences of each tandem pair of symbols that exist in the strings of symbols presented in step (c);

(e) identifying those tandem pairs of symbols, the number of occurrences of which is statistically significant;

(f) mapping on a three-dimensional model of the proteinaceous material those pairs of amino acids represented by the tandem pairs of symbols identified in step (e), wherein a pair of amino acids is two amino acids, at least one of which is accessible to the surface of the proteinaceous material and whose alpha carbons are separated by no more than a predetermined distance; and (g) determining clusters of amino acid pairs mapped in (f), each amino acid pair in the cluster being topographically related to at least one other pair in the cluster, whereby each said cluster is a predicted region on the surface of the proteinaceous material representing said binding surface.

2. A method of identifying a basic element of a binding surface on a proteinaceous material, which binding surface associates with a predetermined binding molecule, comprising:

(a) identifying a cluster of amino acids predicted to represent a binding surface by means of the process of claim 1;

(b) identifying the outermost amino acids of binding pairs in the cluster so as to define the perimeter of the predicted binding surface;

(c) identifying all other amino acids on the surface of the proteinaceous material situated within the perimeter of the predicted binding surface or within a predetermined distance therefrom; and (d) identifying basic elements of the binding surface, each said element being a linear segment of the proteinaceous material whose first and last residues are amino acids identified in (b) or (c) and none of the intermediate amino acids thereof are amino acids on the surface of the proteinaceous material not identified in (b) or (c), any amino acids identified in (b) or (c) that are not part of a said linear segment being a basic element of a single amino acid.

3. A method of producing a binding surface mimetic, comprising:

(a) identifying the basic elements of the binding surface by means of the process of claim 2;

(b) displaying one or more of the basic elements in such a manner as to substantially maintain the relative spatial orientation of the amino acids of (a), thereby identifying a molecule that is mimetic of said binding surface; and (c) producing the mimetic molecule.

4. A method in accordance with claim 3, wherein said step (b) comprises connecting two or more of the basic elements either directly or by means of linkers or by substitution onto an appropriate scaffold in such a manner as to substantially maintain the relative spatial orientation of the amino acids of (a), thereby identifying a molecule that is mimetic of said binding surface.

5. A method in accordance with claim 1, wherein said proteinaceous material is gp120 and said predetermined binding molecule is a broadly neutralizing antibody against gp120.

6. A method of producing a binding surface mimetic, comprising:

(a) identifying the basic elements of the binding surface by means of the process of claim 5;

(b) displaying one or more of the basic elements in such a manner as to substantially maintain the relative spatial orientation of the amino acids of (a), thereby identifying a molecule that is mimetic of said binding surface; and (c) producing the mimetic molecule.

7. A method in accordance with claim 6, wherein said step (b) comprises connecting two or more of the basic elements either directly or by means of linkers or by substitution onto an appropriate scaffold in such a manner as to substantially maintain the relative spatial orientation of the amino acids of (a), thereby identifying a molecule that is mimetic of said binding surface.

8. A method in accordance with claim 2, wherein said proteinaceous material is gp120 and said predetermined binding molecule is a broadly neutralizing antibody against gp120.

9. A method of producing a binding surface mimetic, comprising:

(a) identifying the basic elements of the binding surface by means of the process of claim 8;

(b) displaying one or more of the basic elements in such a manner as to substantially maintain the relative spatial orientation of the amino acids of (a), thereby identifying a molecule that is mimetic of said binding surface; and (c) producing the mimetic molecule.

10. A method in accordance with claim 9, wherein said step (b) comprises connecting two or more of the basic elements either directly or by means of linkers or by substitution onto an appropriate scaffold in such a manner as to substantially maintain the relative spatial orientation of the amino acids of (a), thereby identifying a molecule that is mimetic of said binding surface.

*11. A method of producing a molecule that is mimetic of a binding surface of gp120 that is a discontinuous epitope recognized by the b12 antibody, which molecule includes one or more of the basic elements of the binding surface, comprising:*

*(a) displaying one or more of the peptides comprising sequences selected from the group consisting of:*

*(i) amino acids 254-257 of gp120 of isolate HXB2 of clade B (SEQ ID NO:1) or the corresponding amino acids of the sequence or consensus sequence of gp120 of another HIV isolate or clade;*

*(ii) amino acids 368-376 of gp120 of isolate HXB2 of clade B (SEQ ID NO:1) or the corresponding amino acids of the sequence or consensus sequence of gp120 of another HIV isolate or clade;*

*(iii) amino acids 382-386 of gp120 of isolate HXB2 of clade B (SEQ ID NO:1) or the corresponding amino acids of the sequence or consensus sequence of gp120 of another HIV isolate or clade; and*

*(iv) amino acids 418-424 of gp120 of isolate HXB2 of clade B (SEQ ID NO:1) or the corresponding amino acids of the sequence or consensus sequence of gp120 of another HIV isolate or clade,*

*in such a manner as to substantially maintain the relative spatial orientation that the amino acids thereof have when they are positioned at their native positions in gp120, thereby obtaining a molecule that has a structure that is mimetic of said binding surface, wherein extra residues from gp120 that linearly extend said peptide sequences may be used to maintain said relative spatial orientation, with the proviso that said extra residues do not consist of the entire native gp120 sequence that is between said peptide sequences in native gp120; and*

*(b) producing the binding surface mimetic obtained in step (a).*

*12. A method in accordance with claim 11, wherein said step (a) comprises connecting two or more of said peptides, each in forward or reverse sequence, either directly or by means of linkers or by substitution onto an appropriate scaffold, in such a manner as to substantially maintain the relative spatial orientation that the amino acids thereof have when they are positioned at their native positions in gp120, thereby obtaining a binding surface mimetic that has a structure that is mimetic of said binding surface, wherein extra residues from gp120 that linearly extend said peptide sequences may be used to maintain said relative spatial orientation, with the proviso that said extra residues do not*

*consist of the entire native gp120 sequence that is between said peptide sequences in native gp120.*

*13. A method in accordance with claim 12, wherein said two or more of said peptides is three or more of said peptides.*

*14. A method in accordance with claim 12, wherein said two or more of said peptides is all four of said peptides.*

*15. A method of producing a molecule that is mimetic of a binding surface of gp120 that is a discontinuous epitope recognized by the 17b antibody, which molecule includes one or more of the basic elements of the binding surface, comprising:*

*(a) displaying one or more of the peptides comprising sequences selected from the group consisting of:*

*(i) amino acids 116-124 of gp120 of isolate HXB2 of clade B (SEQ ID NO:1) or the corresponding amino acids of the sequence or consensus sequence of gp120 of another HIV isolate or clade;*

*(ii) amino acids 200-208 of gp120 of isolate HXB2 of clade B (SEQ ID NO:1) or the corresponding amino acids of the sequence or consensus sequence of gp120 of another HIV isolate or clade;*

*(iii) amino acids 419-423 of gp120 of isolate HXB2 of clade B (SEQ ID NO:1) or the corresponding amino acids of the sequence or consensus sequence of gp120 of another HIV isolate or clade; and*

*(iv) amino acids 432-438 of gp120 of isolate HXB2 of clade B (SEQ ID NO:1) or the corresponding amino acids of the sequence or consensus sequence of gp120 of another HIV isolate or clade,*

*in such a manner as to substantially maintain the relative spatial orientation that the amino acids thereof have when they are positioned at their native positions in gp120, thereby obtaining a molecule that has a structure that is mimetic of said binding surface, wherein extra residues from gp120 that linearly extend said peptide sequences may be used to maintain said relative spatial orientation, with the proviso that said extra residues do not consist of the entire native gp120 sequence that is between said peptide sequences in native gp120; and*

*(b) producing the binding surface mimetic obtained in step (a).*

*16. A method in accordance with claim 15, wherein said step (a) comprises connecting two or more of said peptides, each in forward or reverse sequence, either directly or by means of linkers or by substitution onto an appropriate scaffold, in such a manner as to substantially maintain the relative spatial orientation that the amino acids thereof have when they are positioned at their native positions in gp120, thereby obtaining a binding surface mimetic that has a structure that is mimetic of said binding surface, wherein extra residues from gp120 that linearly extend said peptide sequences may be used to maintain said relative spatial orientation, with the proviso that said extra residues do not consist of the entire native gp120 sequence that is between said peptide sequences in native gp120.*

*17. A method in accordance with claim 16, wherein said two or more of said peptides is three or more of said peptides.*

*18. A method in accordance with claim 16, wherein said two or more of said peptides is all four of said peptides.*

*19. A method of producing a molecule that is mimetic of a binding surface of gp120 that is a discontinuous epitope recognized by the CG10 antibody, which molecule includes one or more of the basic elements of the binding surface, comprising:*

*(a) displaying one or more of the peptides comprising sequences selected from the group consisting of:*

*(i) amino acids 119-123 of gp120 of isolate HXB2 of clade B (SEQ ID NO:1) or the corresponding amino acids of the sequence or consensus sequence of gp120 of another HIV isolate or clade;*

*(ii) amino acids 205-207 of gp120 of isolate HXB2 of clade B (SEQ ID NO:1) or the corresponding amino acids of the sequence or consensus sequence of gp120 of another HIV isolate or clade;*

*(iii) amino acids 381-382 of gp120 of isolate HXB2 of clade B (SEQ ID NO:1) or the corresponding amino acids of the sequence or consensus sequence of gp120 of another HIV isolate or clade;*

*(iv) amino acids 421-423 of gp120 of isolate HXB2 of clade B (SEQ ID NO:1) or the corresponding amino acids of the sequence or consensus sequence of gp120 of another HIV isolate or clade; and*

*(v) amino acids 430-435 of gp120 of isolate HXB2 of clade B (SEQ ID NO:1) or the corresponding amino acids of the sequence or consensus sequence of gp120 of another HIV isolate or clade,*

*in such a manner as to substantially maintain the relative spatial orientation that the amino acids thereof have when they are positioned at their native positions in gp120, thereby obtaining a molecule that has a structure that is mimetic of said binding surface, wherein extra residues from gp120 that linearly extend said peptide sequences may be used to maintain said relative spatial orientation, with the proviso that said extra residues do not consist of the entire native gp120 sequence that is between said peptide sequences in native gp120; and*

*(b) producing the binding surface mimetic obtained in step (a).*

*20. A method in accordance with claim 19, wherein said step (a) comprises connecting two or more of said peptides, each in forward or reverse sequence, either directly or by means of linkers or by substitution onto an appropriate scaffold, in such a manner as to substantially maintain the relative spatial orientation that the amino acids thereof have when they are positioned at their native positions in gp120, thereby obtaining a binding surface mimetic that has a structure that is mimetic of said binding surface, wherein extra residues from gp120 that linearly extend said peptide sequences may be used to maintain said relative spatial orientation, with the proviso that said extra residues do not consist of the entire native gp120 sequence that is between said peptide sequences in native gp120.*

*21. A method in accordance with claim 20, wherein said two or more of said peptides is three or more of said peptides.*

*22. A method in accordance with claim 20, wherein said two or more of said peptides is four or more of said peptides.*

*23. A method in accordance with claim 20, wherein said two or more of said peptides is all five of said peptides.*

* * * * *